(12) United States Patent
Wada et al.

(10) Patent No.: US 8,110,689 B2
(45) Date of Patent: *Feb. 7, 2012

(54) BENZANILIDES WITH INSECTICIDAL ACTIVITY

(75) Inventors: Katsuaki Wada, Tochigi (JP); Tetsuya Murata, Tochigi (JP); Katsuhiko Shibuya, Tochigi (JP); Eiichi Shimojo, Tochigi (JP)

(73) Assignee: Bayer Cropsciene AG, Monheim (DE)

( * ) Notice: Subject to any disclaimer, the term of this patent is extended or adjusted under 35 U.S.C. 154(b) by 403 days.

This patent is subject to a terminal disclaimer.

(21) Appl. No.: 11/917,411

(22) PCT Filed: Jun. 2, 2006

(86) PCT No.: PCT/EP2006/005299
§ 371 (c)(1),
(2), (4) Date: Oct. 21, 2009

(87) PCT Pub. No.: WO2006/133823
PCT Pub. Date: Dec. 21, 2006

(65) Prior Publication Data
US 2010/0062937 A1    Mar. 11, 2010

(51) Int. Cl.
C07D 213/00 (2006.01)
C07C 233/00 (2006.01)
A61K 31/44 (2006.01)
A61K 31/16 (2006.01)

(52) U.S. Cl. ......... 546/309; 564/169; 514/352; 514/621

(58) Field of Classification Search ........................ None
See application file for complete search history.

(56) References Cited

FOREIGN PATENT DOCUMENTS

| EP | 1 006 107 | 6/2000 |
|---|---|---|
| EP | 1 671 941 | 6/2006 |
| JP | 11-240857 | 9/1999 |
| JP | 2001-064258 | 3/2001 |
| JP | 2001-064268 | 3/2001 |
| JP | 2001-131141 | 5/2001 |
| JP | 2003-040864 | 2/2003 |
| WO | WO 96/15118 | 5/1996 |
| WO | WO 97/18208 | 5/1997 |
| WO | WO 99/62506 | 12/1999 |
| WO | WO 01/21576 | 3/2001 |
| WO | WO 2005/030699 | 4/2005 |

OTHER PUBLICATIONS

Silverman, R. "The Organic Chemistry of Drug Design and Drug Action," 2004, Elsevier, pp. 29-32.*
M. Seto et al., "Orally Active CCR5 Antagonists as Anti-HIV-1 Agents 2: Synthesis and Biological Activities of Anilide Derivatives Containing a Pyridine N-Oxide Moiety", Chem. Parm. Bull., No. 52, vol. 7, 2004, pp. 818-829.
E. Ikeda et al., "Preparation of Benzanilide Derivatives as Pesticides", XP-002399360, 2005, 2 pgs.
M. Waksmundzka-Hajnos, "Chromatographic Separation of Nitro-Phenones and Their Reduced Derivatives on Thin Layers of Polar Adsorbents", XP-008069069, pp. 159-171.
Jun-Ichi Inoh et al., "Palladium-Catalyzed Coupling Reaction of 4-Alkylnitrobenzenes with Aryl Bromides at Their Benzylic Position", XP-004130892, Tetrahedron Letters, 1998, pp. 4673-4676.
M. Makosza et al., "Synthesis of (p-Nitroaryl)diarylmethanes via Vicarious Nucleophilic Substitution of Hydrogen", XP-002399354, Synthesis, No. 9, 2000, pp. 1237-1240.
S. Florio et al., "Vicarious Nucleophilic Substitution of (Chloroalkyl)heterocycles with Nitroarenes", XP-002399353, Eur. J. Org. Chem., 2004, pp. 2118-2124.
W. Waiers, "Some Substitution Reactions of 4-Aminodiphenylmethane", XP-008069039, pp. 1060-1064.
G. Esselen, Jr., "The Splitting of Benzhydrols by the Action of Bromine", XP-002399352, pp. 308-324.
M.Z.A. Badr et al., "Molecular Rearrangements. 14. Photolysis and Thermolysis of Phenylpropionanilides", XP-002399351, J. Org. Chem., vol. 44, No. 18, 1979, pp. 3244-3247.
Y. Watanabe et al., "Stilbene Derivative, Its Preparation, and Electrophotographic Photoreceptor Using Same", XP-002399363, 2000, 2 pgs.
Kyowa Hakko Kogyo Co., Ltd., "Benzylpyridine Derivatives", XP-002399362, 1977, 1 pg.
M. Hamana et al., "Rearrangement of Anilinomethylpyridines", XP-002399361, 1963, 1 pg.

\* cited by examiner

*Primary Examiner* — Janet Andres
*Assistant Examiner* — Heidi Reese
(74) *Attorney, Agent, or Firm* — Baker Donelson Bearman, Caldwell & Berkowitz, PC

(57) ABSTRACT

Benzanilides of the formula:

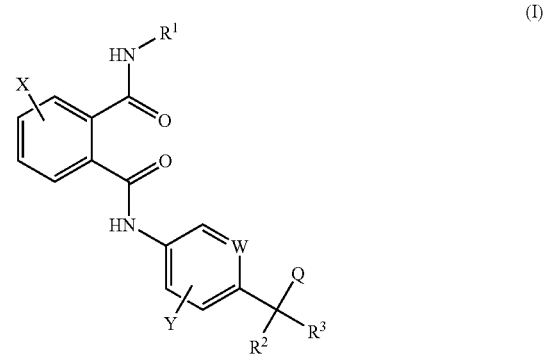

(I)

in which X represents hydrogen, halogen, nitro, $C_{1-6}$ alkylthio, $C_{1-6}$ alkylsulfinyl, $C_{1-6}$ alkylsulfonyl or $C_{1-6}$ alkylsulfonyloxy; Y represents halogen or $C_{1-6}$ alkyl; $R^1$ represents $C_{1-6}$ alkyl, $C_{1-6}$ alkylthio-$C_{1-6}$ alkyl, $C_{1-6}$ alkylsulfinyl-$C_{1-6}$ alkyl or $C_{1-6}$ alkylsulfonyl-$C_{1-6}$ alkyl; $R^2$ represents hydrogen, $C_{1-6}$ alkyl or $C_{1-6}$ haloalkyl; $R^3$ represents hydrogen or hydroxy; W represents CH or N; and Q represents optionally substituted phenyl or optionally substituted pyridyl wherein the substituent is at least one group selected from the group consisting of halogen, $C_{1-6}$ haloalkyl, $C_{1-6}$ haloalkoxy, $C_{1-6}$ haloalkylthio, $C_{1-6}$ haloalkylsulfinyl and $C_{1-6}$ haloalkylsulfoxy; provided that when $R^3$ is hydroxy, $R^2$ is not $C_{1-6}$ alkyl, or when $R^2$ is $C_{1-6}$ haloalkyl, $R^3$ is hydroxy, W is CH, and the substituents of Q are two or more $C_{1-6}$ haloalkyl. Insecticides comprising the benzanilides are herein provided.

16 Claims, No Drawings

BENZANILIDES WITH INSECTICIDAL ACTIVITY

CROSS REFERECE TO RELATED APPLICATIONS

This is a §371 National Stage Application of International Application No. PCT/EP2006/005299 filed Jun. 2, 2006, which claims priority from Japanese Patent Application No. 2005-175036 filed Jun. 15, 2005.

BACKGROUND OF THE INVENTION

1. Field of the Invention

The present invention relates to novel benzanilide compounds and their use as insecticides.

2. Description of Related Art

References D1-D8 disclose that phthalamide derivatives are useful as insecticides. Reference D9 discloses that certain types of phthalamide derivatives act as medical drugs.
D1: JP-A-11-240857
D2: JP-A-2001-64258
D3: JP-A-2001-64268
D4: JP-A-2001-131141
D5: JP-A-2003-40864
D6: WO 01/21576
D7: WO 03/11028
D8: WO 05/030699
D9: JP-A-59-163353

SUMMARY OF THE INVENTION

There have now been found novel benzanilides of the following formula (I):

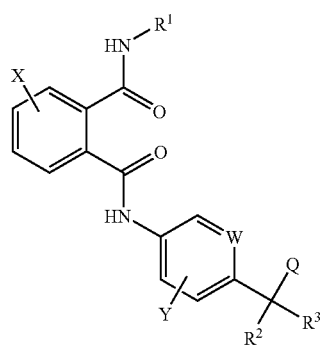

in which X represents hydrogen, halogen, nitro, $C_{1-6}$ alkylthio, $C_{1-6}$ alkylsulfinyl, $C_{1-6}$ alkylsulfonyl or $C_{1-4}$ alkylsulfonyloxy;
Y represents halogen or $C_{1-6}$ alkyl;
$R^1$ represents $C_{1-6}$ alkyl, $C_{1-6}$ alkylthio-$C_{1-6}$ alkyl, $C_{1-6}$ alkylsulfinyl-$C_{1-6}$ alkyl or $C_{1-6}$ alkylsulfonyl-$C_{1-6}$ alkyl;
$R^2$ represents hydrogen, $C_{1-6}$ alkyl or $C_{1-6}$ haloalkyl;
$R^3$ represents hydrogen or hydroxy;
W represents CH or N; and
Q represents optionally substituted phenyl or optionally substituted pyridyl wherein the substituent is at least one group selected from the group consisting of halogen, $C_{1-6}$ haloalkyl, $C_{1-6}$ haloalkoxy and $C_{1-6}$ haloalkylthio,
Q furthermore represents optionally substituted phenyl or optionally substituted pyridyl wherein the substituent is at least one group selected from the group consisting of $C_{1-6}$ haloalkylsulfinyl and $C_{1-6}$ haloalkylsulfonyl.

provided that when $R^3$ is hydroxy, $R^2$ is not $C_{1-6}$ alkyl, or when $R^2$ is $C_{1-6}$ haloalkyl, $R^3$ is hydroxy and W is CH, the substituents of Q are two or more $C_{1-6}$ haloalkyl.

DETAILED DESCRIPTION OF A PREFERRED EMBODIMENT

The compounds of the formula (I) according to the present invention may be obtained for example by any one of Methods (a), (b), (c), (d), (e) and (f) below:

Method (a)

This method comprises reacting compounds of the formula (II):

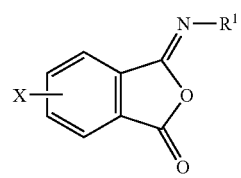

wherein $R^1$ and X are the same as identified above,
with compounds of the formula (III):

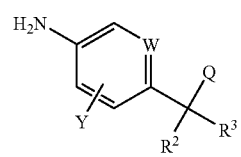

wherein Y, $R^2$, $R^3$, W and Q are the same as identified above,
in the presence of inert solvents, and if appropriate, in the presence of an acid catalyst, Method (b)

This method comprises reacting compounds of the formula (IV):

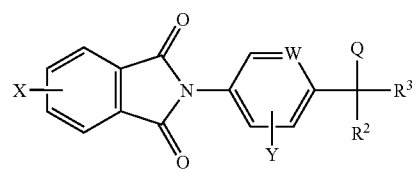

wherein X, Y, $R^2$, $R^3$, W and Q are the same as identified above,
with compounds of the formula (V):

wherein $R^1$ is the same as identified above,
in the presence of inert solvents, and if appropriate, in the presence of an acid catalyst, Method (c)
This method comprises reacting compounds of the formula (VI):

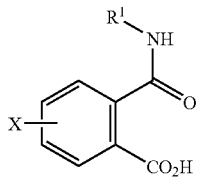

(VI)

wherein X and R¹ are the same as identified above,
with the compounds the above formula (III),
in the presence of inert solvents, and if appropriate, in the presence of an acid catalyst, Method (d)
This method comprises reacting compounds of the formula (VII):

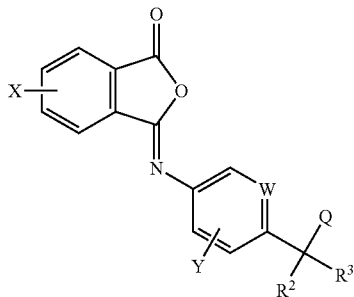

(VII)

wherein X, Y, $R^2$, $R^3$, W and Q are the same as identified above,
with the compounds of the above formula (V),
in the presence of inert solvents, and if appropriate, in the presence of an acid catalyst, Method (e)
This method comprises reacting compounds of the formula (VIII):

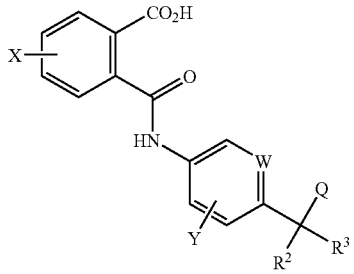

(VIII)

wherein X, Y, $R^2$, $R^3$, W and Q are the same as identified above,
with the compounds of the above formula (V),
in the presence of inert solvents, and if appropriate, in the presence of an acid catalyst, Method (f)
When R¹ is $C_{1-6}$ alkylsulfinyl-$C_{1-6}$ alkyl or $C_{1-6}$ alkylsulfonyl-$C_{1-6}$ alkyl, this method comprises reacting compounds of the formula (If):

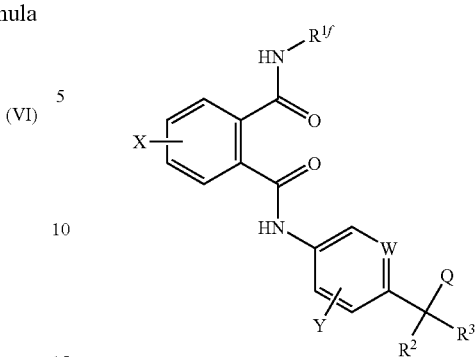

(If)

wherein $R^{1f}$ represents $C_{1-6}$ alkylthio-$C_{1-6}$ alkyl and X, Y, $R^2$, $R^3$, W and Q are the same as identified above,
with an oxidant in the presence of inert solvents.

The benzanilides of the above formula (I) according to the present invention exhibit strong insecticidal activity.

The compounds of formula (I) of the present invention, though encompassed by the general formula described in D1 above, are novel compounds which are not in any way specifically disclosed therein, and surprisingly show noticeably remarkable insecticidal activity as compared with the compounds as particularly recited in D1.

In the present specification, "halogen" denotes fluorine, chlorine, bromine and iodine, preferably fluorine, chlorine and bromine.

"Alkyl" denotes straight-chain or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, etc., preferably $C_{1-6}$ alkyl.

The alkyl part in each of "alkylthio", "alkylsulfinyl", "alkylsulfonyl", "alkylsulfonyloxy", "alkylthioalkyl", "alkylsulfinylalkyl", "alkylsulfonylalkyl", "haloalkyl", "haloalkoxy" and "haloalkylthio" may similarly be exemplified as those examples explained in "alkyl" as above.

Examples explained in the "halogen" above may similarly be the examples of the halogen part in "haloalkyl", "haloalkoxy" and "haloalkylthio".

In the formula (I) of the present invention, preferred compounds are those in which
X is halogen, nitro, $C_{1-4}$ alkylthio, $C_{1-4}$ alkylsulfinyl, $C_{1-4}$ alkylsulfonyl, or $C_{1-4}$ alkylsulfonyloxy;
Y is halogen or $C_{1-4}$ alkyl;
R¹ is $C_{1-4}$ alkyl, $C_{1-4}$ alkylthio-$C_{1-4}$ alkyl, $C_{1-4}$ alkylsulfinyl-$C_{1-4}$ alkyl or $C_{1-4}$ alkylsulfonyl-$C_{1-4}$ alkyl;
$R^2$ is hydrogen, $C_{1-4}$ alkyl or $C_{1-4}$ haloalkyl;
$R^3$ is hydrogen or hydroxy;
W is CH or N; and
Q is optionally substituted phenyl or optionally substituted pyridyl wherein the substituent is at least one group selected from the group consisting of halogen, $C_{1-4}$ haloalkyl, $C_{1-4}$ haloalkoxy and $C_{1-4}$ haloalkylthio,
Q is furthermore optionally substituted phenyl or optionally substituted pyridyl wherein the substituent is at least one group selected from the group consisting of $C_{1-4}$ haloalkylsulfinyl and $C_{1-4}$ haloalkylsulfonyl
provided that when $R^3$ is hydroxy, $R^2$ is not $C_{1-4}$ alkyl, or when $R^2$ is $C_{1-4}$ haloalkyl, $R^3$ is hydroxy and W is CH, the substituents of Q are two or more $C_{1-4}$ haloalkyl.

Among them, in the formula (I) of the present invention, particularly preferred compounds are those in which X is fluorine, chlorine, bromine, iodine, nitro, methylthio, methylsulfinyl, methylsulfonyl or methylsulfonyloxy;

Y is chlorine or methyl;

R$^1$ is isopropyl, C$_{1-2}$ alkylthio-C$_{3-4}$ alkyl, C$_{1-2}$ alkylsulfinyl-C$_{3-4}$ alkyl or C$_{1-2}$ alkylsulfonyl-C$_{3-4}$ alkyl;

R$^2$ is hydrogen, methyl or trifluoromethyl;

R$^3$ is hydrogen or hydroxy;

W is CH or N; and

Q is optionally substituted phenyl or optionally substituted pyridyl wherein the substituent is at least one group selected from the group consisting of chlorine, bromine, C$_{1-4}$ perhaloalkyl, perhaloalkoxy and C$_{1-4}$ perhaloalkylthio;

Q is furthermore optionally substituted phenyl or optionally substituted pyridyl wherein the substituent is at least one group selected from the group consisting of C$_{1-4}$ perhaloalkylsulfinyl and C$_{1-4}$ perhaloalkylsulfonyl;

provided that when R$^3$ is hydroxy, R$^2$ is not methyl, or when R$^2$ is trifluoromethyl, R$^3$ is hydroxy and W is CH, the substituents of Q are two or more C$_{1-4}$ perhaloalkyl.

Among them, in the formula (I) of the present invention, very particularly preferred compounds are those in which X is fluorine, chlorine, bromine, iodine, nitro, methylthio, methylsulfinyl, methylsulfonyl or methylsulfonyloxy;

Y is chlorine or methyl;

R$^1$ is isopropyl, C$_{1-2}$ alkylthio-C$_{3-4}$ alkyl, C$_{1-2}$ alkylsulfinyl-C$_{3-4}$ alkyl or C$_{1-2}$ alkylsulfonyl-C$_{3-4}$ alkyl;

R$^2$ is hydrogen, methyl or trifluoromethyl;

R$^3$ is hydrogen or hydroxy;

W is CH or N; and

Q is optionally substituted phenyl or optionally substituted pyridyl wherein the substituent is at least one group selected from the group consisting of chlorine, bromine, trifluoromethyl, pentafluoroethyl, heptafluoro-n-propyl, heptafluoro-i-propyl, nonafluoro-n-butyl, trifluoromethoxy, trifluoromethylthio, trifluoromethylsulfinyl, trifluoromethylsulfonyl, pentafluoroethylthio, pentafluoroethylsulfonyl and difluorobromomethoxy provided that when R$^3$ is hydroxy, R$^2$ is not methyl, or when R$^2$ is trifluoromethyl, R$^3$ is hydroxy and W is CH, the substituents of Q are two or more of the group consisting of trifluoromethyl, pentafluoroethyl, heptafluoro-n-propyl, heptafluoro-i-propyl and nonafluoro-n-butyl.

The compounds of the formula (I) according to the present invention include stereoisomers (R/S coordinate) when the group R$^1$ has an asymmetric carbon.

Method (a) may be represented by the following reaction formula when, for example, 4-chloro-3-(1,1-dimethyl-2-methylthioethylimino)-3H-isobenzofuran-1-one and 4-(3,5-bis-trifluoromethyl-benzyl)-2-methylaniline are used as the starting materials.

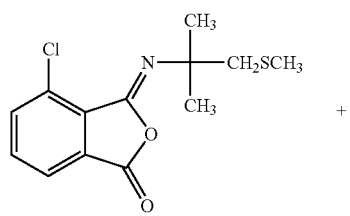

+

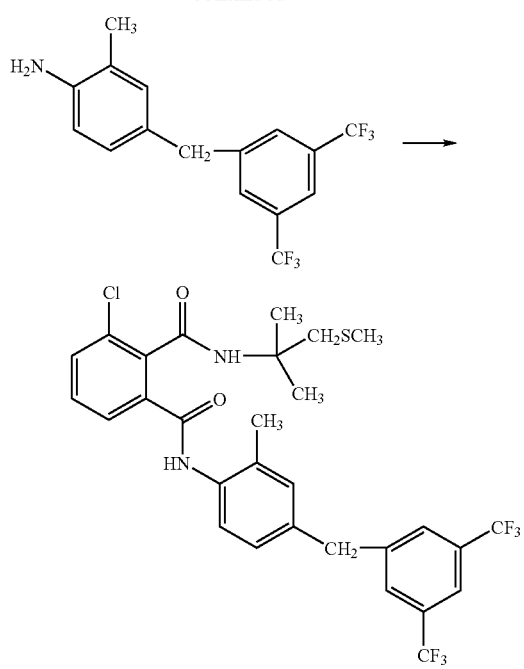

Method (b) may be represented by the following reaction formula when, for example, 2-[4-(3,5-bis-trifluoromethyl-benzyl)-2-methylphenyl]-4-chloroisoindole-1,3-dione and (S)-1-methyl-2-methylthioethylamine are used as the starting materials.

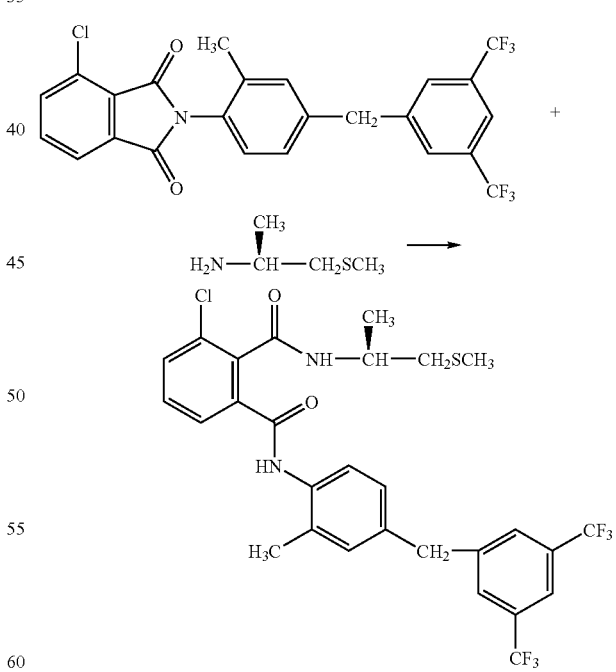

Method (c) may be represented by the following reaction formula when, for example, 3-chloro-N-(1,1-dimethyl-2-methylthioethyl)-phthalamic acid and 4-(3,5-bis-trifluoromethyl-α-methylbenzyl)-2-methylaniline are used as the starting materials.

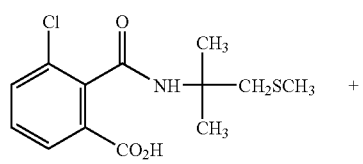

+

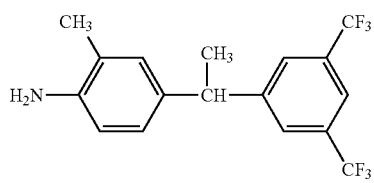

→

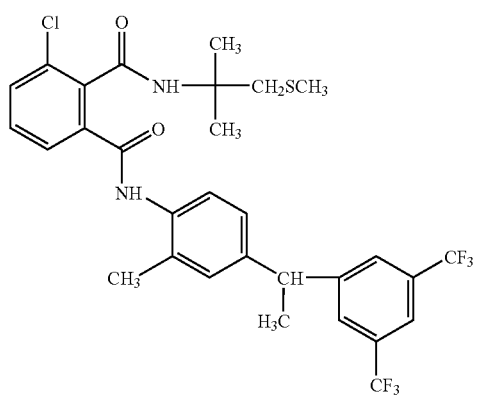

Method (d) may be represented by the following reaction formula when, for example, 1-[4-(4-chloro-3-oxo-3H-isobenzofuran-1-ylideneamino)-3-methyl-benzyl]-3,5-bis-trifluoromethyl-benzene and 1-methyl-2-methylthioethylamine are used as the starting materials.

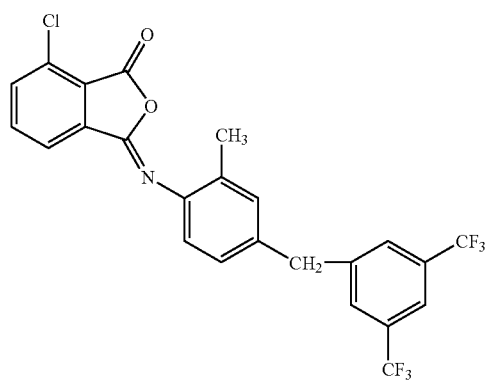

+

→

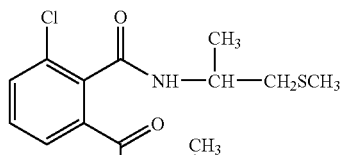

Method (e) may be represented by the following reaction formula when, for example, N-[4-(3,5-bis-trifluoromethyl-benzyl)-2-methyl-phenyl]-6-chloro-phthalamic acid and 1-methyl-2-methylthioethylamine are used as the starting materials.

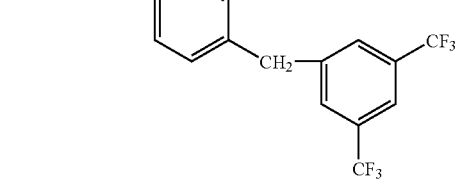

+ acid binder →

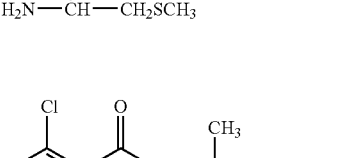

Method (f) may be represented by the following reaction formula when, for example, $N^2$-(1-methyl-2-methylthioethyl)-3-chloro-$N^1$-[2-methyl-4-(3,5-bis-trifluoromethyl-benzyl)phenyl]phthalamide and m-chloroperbenzoic acid are used as the starting materials.

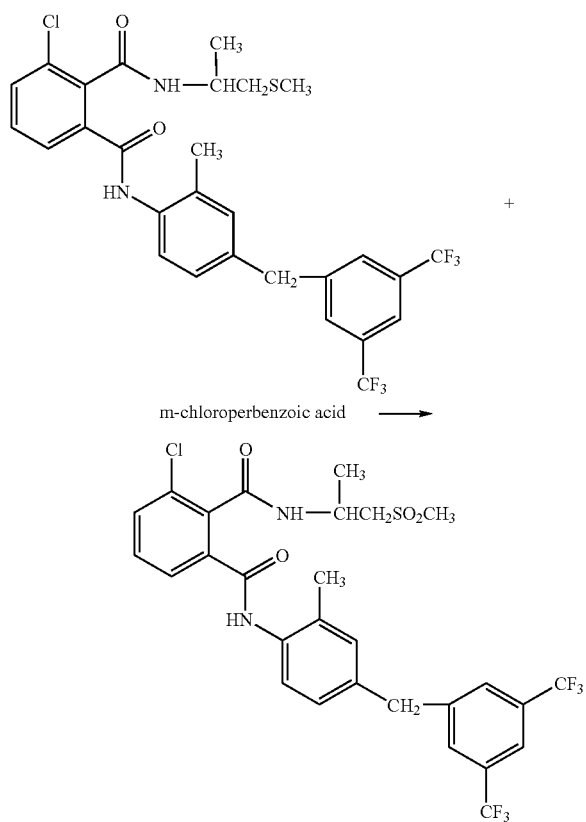

m-chloroperbenzoic acid

The compounds of the formula (II) which are used as the starting material in Method (a) are known compounds and may be readily produced according to, for example, JP-A-11-240857, JP-A-2001-131141 and so on.

Examples of the compound of the formula (II) used as the starting material in Method (a) include
3-isopropylimino-3H-isobenzofuran-1-one,
4-fluoro-3-isopropylimino-3H-isobenzofuran-1-one,
4-chloro-3-isopropylimino-3H-isobenzofuran-1-one,
4-bromo-3-isopropylimino-3H-isobenzofuran-1-one,
4-iodo-3-isopropylimino-3H-isobenzofuran-1-one,
3-(1-methyl-2-methylthioethylimino)-3H-isobenzofuran-1-one,
4-fluoro-3-(1-methyl-2-methylthioethylimino)-3H-isobenzofuran-1-one,
4-chloro-3-(1-methyl-2-methylthioethylimino)-3H-isobenzofuran-1-one,
4-bromo-3-(1-methyl-2-methylthioethylimino)-3H-isobenzofuran-1-one,
4-iodo-3-(1-methyl-2-methylthioethylimino)-3H-isobenzofuran-1-one,
3-(1,1-dimethyl-2-methylthioethylimino)-3H-isobenzofuran-1-one,
3-(1,1-dimethyl-2-methylthioethylimino)-4-fluoro-3H-isobenzofuran-1-one,
4-chloro-3-(1,1-dimethyl-2-methylthioethylimino)-3H-isobenzofuran-1-one,
4-bromo-3-(1,1-dimethyl-2-methylthioethylimino)-3H-isobenzofuran-1-one,
3-(1,1-dimethyl-2-methylthioethylimino)-4-iodo-3H-isobenzofuran-1-one,
methanesulfonic acid 3-isopropylimino-1-oxo-1,3-dihydro-isobenzofuran-4-yl ester,
methanesulfonic acid 3-(1-methyl-2-methylthioethylimino)-1-oxo-1,3-dihydro-isobenzofuran-4-yl ester,
methanesulfonic acid 3-(1,1-dimethyl-2-methylthioethylimino)-1-oxo-1,3-dihydro-isobenzofuran-4-yl ester, and so on.

Some of the compounds of the formula (III) used as the starting material in Method (a) are new compounds not published in the prior art, but they may be obtained by, for example, the catalytic hydrogenation, a well-known method in the art of organic chemistry, from compounds of the formula (IX):

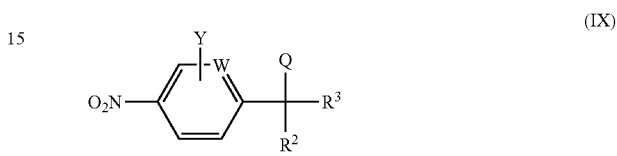

(IX)

in which Y, $R^2$, $R^3$, W and Q are the same as identified above, which are reduced by hydrogen in the presence of a reduction catalyst such as palladium carbon, Raney nickel, platinum oxide, etc.

The catalytic hydrogenation may be carried out in a suitable diluent, examples of such diluent being ethers such as ethyl ether, methylethyl ether, isopropyl ether, butyl ether, dioxane, and tetrahydrofuran (THF); alcohols such as methanol, ethanol, isopropanol, butanol and ethylene glycol. Examples of the reduction catalyst are palladium carbon, Raney nickel, platinum oxide and the like. The reaction may be carried out generally at a temperature of about 0-100° C., preferably at room temperature to about 80° C. and under normal pressure and optionally under increased pressure. For example, the compound of the formula (III) may be obtained by adding hydrogen to the compound of The formula (IX) in the presence of 0.1-10% w/w of palladium carbon in a diluent, for example ethanol.

The compounds of the formula (III) may alternatively be obtained from the compounds of the formula (IX) by a reducing reaction using a metal or the like instead of the catalytic hydrogenation.

As the reduction using the metal or the like, a reaction of iron powder in acetic acid, a reaction of zinc dust under a neutral condition (Organic Syntheses Collective, Vol. II, pp. 447), a reaction of stannic chloride under an acid condition (Organic Syntheses Collective, Vol. II, pp. 254), a reaction of titanium trichloride under a neutral condition and so on may be mentioned.

Novel compounds of the general formula (III) are represented by formula (III-a)

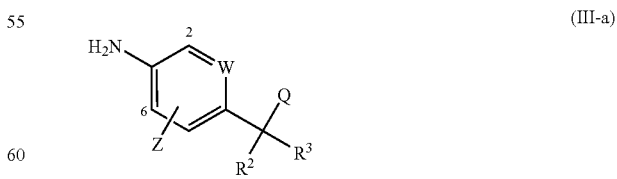

(III-a)

in which
W represents CH or N;
Z represents $C_{1-6}$ alkyl or halogen;
$R^2$ represents hydrogen, $C_{1-6}$ alkyl or $C_{1-6}$ haloalkyl;
$R^3$ represents hydrogen or hydroxy; and Q represents optionally substituted phenyl or optionally substituted pyridyl wherein the substituent is at least one group selected from the group consisting of $C_{1-6}$ haloalkyl, $C_{1-6}$ haloalkoxy and $C_{1-6}$ haloalkylthio, $C_{1-6}$ haloalkylsulfinyl and $C_{1-6}$ haloalkylsulfonyl.

provided that when $R^3$ is hydroxy, $R^2$ is not $C_{1-6}$ alkyl, or when $R^2$ is $C_{1-6}$ haloalkyl, $R^3$ is hydroxy and W is CH, the substituents of Q are two or more $C_{1-6}$ haloalkyl.

Many of the compounds of the formula (IX) are new compounds, and when $R^2$ and $R^3$ are both hydrogen, the compounds of the formula (IX) may be obtained, for example, by reacting compounds of the formula (X):

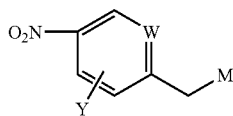
(X)

in which Y and W are the same as identified above and M represents chloro, bromo or methylsulfonyloxy,
with compounds of the formula (XI):

(XI)

in which Q is the same as identified above.

The above reaction may be carried out according to the method described in J. Org. Chem., 1994, Vol. 59, pp. 6501.

Novel compounds of the general formula (IX) are represented by the formula (IX-b)

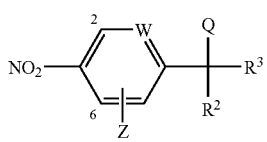
(IX-b)

in which
Z represents $C_{1-6}$ alkyl;
Z furthermore represents halogen in the 2- or 6-position of the ring system;
$R^2$ represents hydrogen, $C_{1-6}$ alkyl or $C_{1-6}$ haloalkyl;
$R^3$ represents hydrogen or hydroxy;
W represents CH or N; and
Q represents optionally substituted phenyl or optionally substituted pyridyl wherein the substituent is at least one group selected from the group consisting of halogen; $C_{1-6}$ haloalkyl, $C_{1-6}$ haloalkoxy and $C_{1-6}$ haloalkylthio, $C_{1-6}$ haloalkylsulfinyl and $C_{1-6}$ haloalkylsulfonyl.

provided that when $R^3$ is hydroxy, $R^2$ is not $C_{1-6}$ alkyl, or when $R^2$ is $C_{1-6}$ haloalkyl, $R^3$ is hydroxy and W is CH, the substituents of Q are two or more $C_{1-6}$ haloalkyl.

The compounds of the formula (X) above are well-known compounds in the art of organic chemistry and may be readily obtained by the methods as described, for example, in J. Chem. Soc., 1967, pp. 1154-1158 and J. Amer. Chem. Soc., Vol. 75, 1953, pp. 3830.

Representative examples of the compounds of the formula (X) are;
3-methyl-4-nitrobenzyl chloride,
3-methyl-4-nitrobenzyl bromide,
methanesulfonic acid 3-methyl-4-nitrobenzyl ester, and
3-chloro-4-nitrobenzyl chloride.

The compounds of the formula (IX), wherein $R^2$ is hydrogen and $R^3$ is hydroxy; may be, obtained by oxidizing compounds of the formula (IX-a):

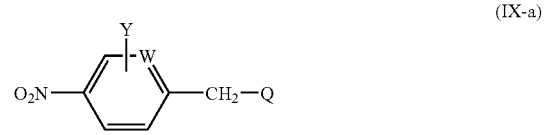
(IX-a)

in which Y, W and Q are the same as identified above,
to obtain compounds of the formula (XII):

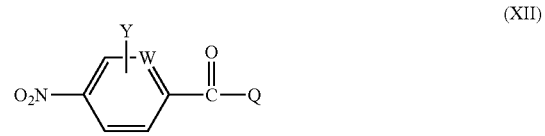
(XII)

in which Y, W and Q are the same as identified above,
followed by reducing the compounds of the formula (XII).

The above reaction may be carried out according to the method described in Chem. Ber., Vol. 18, 1885, pp. 2402.

The compounds of the formula (IX), wherein $R^2$ is $C_{1-6}$ haloalkyl and $R^3$ is hydroxy, for example, $R^2$ is $C_{1-6}$ perhaloalkyl and $R^3$ is hydroxy, may be obtained by reacting the compounds of the formula (XII) with compounds of the formula (XIII):

(XIII)

in which $R^{2a}$ represents $C_{1-6}$ perhaloalkyl.

The above reaction may be carried out according to the method described in J. Org. Chem., Vol. 56, No. 3, 1991, pp. 984. Instead of the trimethylsilyl of The formula (XIII), a triethylsilyl may alternatively be used for the reaction.

The compounds of the formula (IX), wherein $R^2$ is $C_{1-6}$ haloalkyl and $R^3$ is hydrogen, for example $R^2$ is $C_{1-6}$ perhaloalkyl and $R^3$ is hydrogen, may be obtained by reacting the compounds of the formula (IX) in which $R^2$ is $C_{1-6}$ perhaloalkyl and $R^3$ is hydroxy, with methanesulfonyl chloride followed by reacting it with lithium aluminum hydride.

The above reaction may be carried out according to the reaction described in J. Chem. Soc. Perkin Trans., Vol. 1, 1983, pp. 1267.

The compounds of the formula (XI), another starting material for the preparation of the compounds of the formula (IX), includes publicly known compounds, for example, 3-trifluoromethylphenylboronic acid, 3,5-dichlorophenylboronic acid, 3,5-bis-trifluoromethylphenylboronic acid, 2-chloropyridine-4-boronic acid, 2-chloropyridine-5-boronic acid, 4-trifluoromethylpyridine-3-boronic acid, 5-trifluoromethylpyridine-2-boronic acid and so on. The boronic acids of pyridine may be obtained according to the method described in Tetrahedron, 2001, pp. 2991.

Instead of the boronic acid of the formula (XI) above, boronic acid ester may be used for the reaction.

The reaction of the compounds of the formula (X) with the compounds of the formula (XI) may be carried out in a suitable diluent, examples of which include aliphatic, cycloaliphatic and aromatic hydrocarbons (optionally chlorinated), for example, pentane, hexane, cyclohexane, petroleum ether, ligroin, benzene, toluene, xylene, dichloromethane; ethers such as ethylether, methyl-ethylether, isopropylether, butylether, dioxane, dimethoxyethane (DME), tetrahydrofuran (THF) and diethyleneglycoldimethylether (DGM); ketones such as acetone, methylethylketone (MEK), methyl-isopropylketone and methylisobutylketone (MIBK); nitriles such as acetonitrile, propionitrile and acrylonitrile; esters such as ethyl acetate and amyl acetate; acid amides such as dimethylformamide (DMF), dimethylacetoamide (DMA), N-methylpyrrolidone, 1,3-dimethyl-2-imidazolidinone and hexamethylphosphorictriamide (HMPA).

This reaction may be carried out in the presence of an acid binder. Examples of such acid binder include, as inorganic bases, hydrides, hydroxides, carbonates and hydrogen carbonates of alkali metal or alkaline earth metal such as sodium hydride, lithium hydride, sodium hydrogen carbonate, potassium hydrogen carbonate, sodium carbonate, potassium carbonate, lithium hydride, sodium hydroxide, potassium hydroxide and calcium hydroxide; inorganic alkali metal amides such as lithium amide, sodium amide and potassium amide; and as organic bases, alcoholate, tertiary amines, dialkylaminoanilines, and pyridines such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU).

The above reaction may also be carried out by the use of a phase-transfer catalyst in the presence of a diluent. Examples of the diluent are water; aliphatic, cycloaliphatic and aromatic hydrocarbons (optionally chlorinated), for example, pentane, hexane, cyclohexane, petroleum ether, ligroin, benzene, toluene, xylene and the like; ethers such as ethylether, methylethylether, isopropylether, butylether, dioxane, dimethoxyethane (DME), tetrahydrofuran (TI-IF) and diethyleneglycoldimethylether (DGM). Examples of the phase-transfer catalyst are quaternary ions such as tetramethylammonium bromide, tetrapropylammonium bromide, tetrabutylammonium bromide, tetrabutylammonium bissulphate, tetrabutylammonium iodide, trioctylmethylammonium chloride, benzyltriethylammonium bromide, butylpyridinium bromide, heptylpyridinium bromide and benzyltriethylammonium chloride; and crown ethers such as dibenzo-18-crown-6, dicyclohexyle-18-crown-6 and 18-crown-6, cryptands such as [2.2.2]-cryptate, [2.1.1]-cryptate, [2.2.1]-cryptate, [2.2.B]-cryptate and [3.2.2]-cryptate.

The above reaction may be carried out in a substantially wide temperature range, but generally between about 0 and about 200° C., preferably between room temperature and about 150° C. Desirably, the reaction should be carried out under normal pressure but optionally it may be operated under increased or reduced pressure.

As an alternative process for preparation of the compounds of the formula (III) above, the compounds of the formula (III), when both of $R^2$ and $R^3$ are hydrogen, may be readily obtained by reacting under acid condition compounds of the formula (XIV):

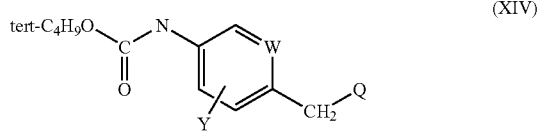

(XIV)

in which Y, W and Q are the same as identified above.

This reaction may be carried out according to the method described in J. Org. Chem., 1969, pp. 395, J. Med. Chem., 1990, pp. 1153 and others.

In the above method, an ester of benzyl, methyl or ethyl may be used for the tert-butyl ester of carbamic acid of the formula (XIV). In the case of benzylester, the target compound of The formula (III) may be obtained by catalytic hydrogen reduction, and in the case of methylester and ethylester, it may be obtained by reaction under alkaline condition (deprotection).

The catalytic hydrogenation may be carried out according to the method described in J. Org. Chem., 1981, pp. 134. The deprotection reaction under the alkaline condition may be carried out according to the method described in J. Am. Chem. Soc., 1952, pp. 1087.

The compounds of the formula (XIV) above may be obtained by, for example, reacting compounds of the formula (XV):

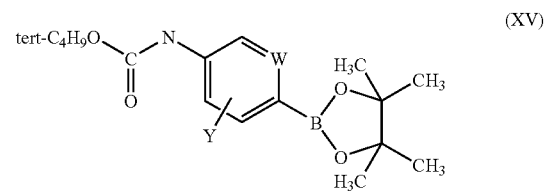

(XV)

in which Y and W are the same as identified above, with compounds of the formula (XVI):

Q-CH$_2$-M (XVI)

in which Q and M are the same as identified above.

The above reaction may be carried out according to the method described in J. Org. Chem., 1994, Vol. 59, pp. 6501.

The compound of the formula (XV) above may be obtained by reacting compounds of the formula (XVII):

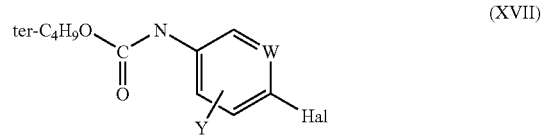

(XVII)

in which Y and W are the same as identified above and Hal represents halogen, with pinacolborane using a palladium catalyst.

This reaction may be carried out according to the method described in J. Org. Chem., 2000, Vol. 65, pp. 168.

(4-Iodo-2-methyphenyl) carbamic acid tert-butyl ester, as a representative example of the compound of the formula (XVII) above, may be easily obtained from the well-known 4-iodo-2-methylaniline.

The compounds of The formula (XVI) in which the substituent of Q is perfluoroalkyl with two or more carbon atoms may be obtained by the method described in Tetrahedron, 2002, Vol. 58, pp. 3999 or Tetrahedron Lett., Vol. 32, No. 1, 1991, pp. 91.

The compounds of the formula (XIV) above may alternatively be obtained by reacting compounds of the formula (XVIII):

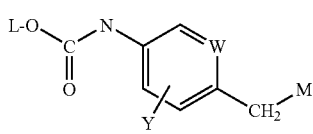

in which Y, W and M are the same as identified above and L represents methyl, ethyl, tert-butyl or benzyl, with the boronic acid of the formula (XI) above or ester thereof.

The compounds of the formula (XVIII) above may be obtained according to the method described in J. Org. Chem., 2002, pp. 741.

Representative examples of the compounds of the formula (III) include;
4-(3,5-bis-trifluoromethylbenzyl)-2-methylaniline,
4-(3,5-bis-pentafluoroethylbenzyl)-2-methylaniline,
4-(3,5-bis-perfluorobutylbenzyl)-2-methylaniline,
4-(3,4-bis-pentafluoroethylbenzyl)-2-methylaniline,
4-(3,5-dichlorobenzyl)-2-methylaniline,
4-(3,5-dibromobenzyl)-2-methylaniline,
4-(4-trifluoromethoxybenzyl)-2-methylaniline,
4-(4-trifluoromethylthiobenzyl)-2-methylaniline,
4-(4-iso-perfluoropropylbenzyl)-2-methylaniline, and
4-(2,6-bis-pentafluoroethyl-pyridin-4-yl)-methylaniline.

The compounds of the formula (IV) used as the starting material in Method (b) above are novel and may be easily obtained, for example, by reacting compounds of the formula (XIX):

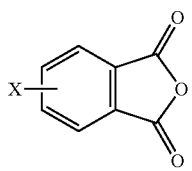

in which X is the same as identified above, with the compounds of the formula (III) above, according to the method described in JP-A-61-246161.

This reaction may be carried out in a suitable diluent. Examples of the diluent are aliphatic, cycloaliphatic and aromatic hydrocarbons (optionally chlorinated), for example, pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as ethylether, methylethylether, isopropylether, butylether, dioxane, dimethoxyethane (DME), tetrahydrofuran (THF) and diethyleneglycoldimethylether (DGM); esters such as ethyl acetate and amyl acetate; acid amides such as dimethylformamide (DMF), dimethylacetoamide (DMA), N-methylpyrrolidone, 1,3-dimethyl-2-imidazolidinone and hexamethylphosphoricamide (HMPA); acids such as acetic acid etc.

The above reaction may be carried out in a substantially wide temperature range, but generally between room temperature and about 200° C., preferably between room temperature and about 150° C. Desirably, the reaction should be carried out under normal pressure but optionally it may be operated under increased or reduced pressure.

Many of the compounds of the formula (XIX) are well known. Examples thereof include phthalic anhydride, 3-fluorophthalic anhydride, 3-chlorophthalic anhydride, 3-bromophthalic anhydride, 3-iodophthalic anhydride, 3-methanesulfonyloxyphthalic anhydride and so on.

Of the compounds exemplified above, 3-methanesulfonyloxyphthalic anhydride may be obtained easily from 3-hydroxyphthalic anhydride and methanesulfonylchloride according to the method described in Tetrahedron Lett., Vol. 29, pp. 5595-8 (1988).

Representative examples of the compounds of the formula (IV) which are used as the starting material in Method (b) are given below;
4-chloro-2-[2-methyl-4-(3,5-bis-trifluoromethylbenzyl)-phenyl]isoindole-1,3-dione,
4-chloro-2-[2-methyl-4-(3,5-bis-pentafluoroethylbenzyl)-phenyl]isoindole-1,3-dione and so on.

The compounds of the formula (V) used as the starting material in Method (b) may either be a well-known compound in the art of organic chemistry or be synthesized according to the method described in German Patent No. 2045905, WO 01/23350 and so on. Examples thereof include ethylamine, diethylamine, n-propylamine, isopropylamine, n-butylamine, sec-butylamine, isobutylamine, t-butylamine, t-amylamine, 2-(methylthio)-ethylamine, 2-(ethylthio)-ethylamine, 1-methyl-2-(methylthio)-ethylamine, 1,1-dimethyl-2-(methylthio)-ethylamine and so on.

The compounds of the formula (VI) which are used as the starting material in Method (c) encompasses publicly known compounds and may be readily produced according to the method described in JP-A-11-240857, JP-A-2001-131141 and so on. The following are the examples thereof:
N-isopropyl-phthalamic acid,
3-fluoro-N-isopropyl-phthalamic acid,
3-chloro-N-isopropyl-phthalamic acid,
3-bromo-N-isopropyl-phthalamic acid,
3-iodo-N-isopropyl-phthalamic acid,
N-(1-methyl-2-methylthioethyl)-phthalamic acid,
3-fluoro-N-(1-methyl-2-methylthioethyl)-phthalamic acid,
3-chloro-N-(1-methyl-2-methylthioethyl)-phthalamic acid,
3-bromo-N-(1-methyl-2-methylthioethyl)-phthalamic acid,
3-iodo-N-(1-methyl-2-methylthioethyl)-phthalamic acid,
N-(1,1-dimethyl-2-methylthioethyl)-phthalamic acid,
N-(1,1-dimethyl-2-methylthioethyl)-3-fluoro-phthalamic acid,
3-chloro-N-(1,1-dimethyl-2-methylthioethyl)-phthalamic acid,
3-bromo-N-(1,1-dimethyl-2-methylthioethyl)-phthalamic acid,
N-(1,1-dimethyl-2-methylthioethyl)-3-iodo-phthalamic acid,
N-isopropyl-3-methanesulfonyloxy-phthalamic acid,
N-(1-methyl-2-methylthioethyl)-3-methanesulfonyloxy-phthalamic acid,
N-(1-methyl-2-methylthioethyl)-3-nitro-phthalamic acid,
3-chloro-N-(2-ethylthio-1-methyl-ethyl)-phthalamic acid,
3-bromo-N-(2-ethylthio-1-methyl-ethyl)-phthalamic acid,
N-(2-ethylthio-1-methyl-ethyl)-3-iode-phthalamic acid,
N-(2-ethylthiol-methyl-ethyl)-3-nitro-phthalamic acid,
N-(2-ethyl-1-methyl-ethyl)-3-methanesulfonyloxy-phthalamic acid,
N-(1,1-dimethyl-2-methyl-ethyl)-3-methanesulfonyloxy-phthalamic acid and so on.

The compounds of the formula (VI) exemplified above may be readily obtained generally by reacting the phthalamic anhydrides of the formula (XIX) above with amines of the formula (XX):

$$R^1-NH_2 \qquad (XX)$$

in which $R^1$ is the same as identified above.

The compounds of the formula (XX) above are well known in the art of organic chemistry. Examples thereof include ethylamine, n-propylamine, isopropylamine, n-butylamine, sec-butylamine, isobutylamine, t-butylamine, t-amylamine, 2-(methylthio)ethylamine, 2-(ethylthio) ethylamine, 1-methyl-2-(methylthio)ethylamine, 1,1-dimethyl-2-(methylthio) ethylamine and the like.

These amines may be easily obtained by the method described in German Patent No. 2045905, WO 01/23350 as well.

The reaction of the compounds of the formula (XIX) above with the amines of the formula (XX) may be carried out for example by the method described in J. Org. Chem., Vol. 46, pp. 175, 1981 and others, and it may be worked in a suitable diluent. The diluent used therein may be for example aliphatic, cycloaliphatic and aromatic hydrocarbons (optionally chlorinated), for example pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as ethylether, methylethylether; isopropylether, butylether, dioxane, dimethoxyethane (DME), tetrahydrofuran (THF) and diethyleneglycoldimethylether (DGM); ketones such as acetone, methylethylketone (MEK), methylisopropylketon and methylisobutylketon (MIBK); nitriles such as acetonitrile, propionitrile and acrylonitrile; esters such as ethyl acetate and amyl acetate.

The above reaction may be conducted in the presence of a base, examples of such base being tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ene (DBU) and so on.

The above reaction may be carried out in a substantially wide temperature range, but generally between about −70 and about 100° C., preferably between about −50 and about 80° C. Desirably, the reaction should be carried out under normal pressure but optionally it may be operated under increased or reduced pressure.

The compounds of the formula (VII) used as the starting material in Method (d) are a new compounds, and may be easily obtained for example by reacting the compounds of the formula (VIII) which is the starting material in Method (e) in the presence of a condensing agent according to the method described in J. Med. Chem., Vol. 10, pp. 982, 1967.

The following are the representative examples of the compounds of the formula (VII):
1-[4-(4-iodo-3-oxo-3H-isobenzofuran-1-ylideneamino)-3-methyl-benzyl]-3,5-bis-trifluoromethyl-benzene,
1-[4-(4-chloro-3-oxo-3H-isobenzofuran-1-ylideneamino)-3-methyl-benzyl]-3,5-bis-trifluoromethyl-benzene,
1-[4-(4-chloro-3-oxo-3H-isobenzofuran-1-ylideneamino)-3-methyl-benzyl]-3,4-bis-pentafluoroethyl-benzene,
1-[4-(4-iodo-3-oxo-3,1-isobenzofuran-1-ylideneamino)-3-methyl-benzyl]-3,5-bis-pentafluoroethyl-benzene,
1-[4-(4-chloro-3-oxo-3H-isobenzofuran-1-ylideneamino)-3-methyl-benzyl]-3,4-bis-heptafluoropropyl-benzene and so on.

The compounds of the formula (V) used as the starting material in Method (d) are as explained in Method (b).

The compounds of the formula (VIII) used as the starting material in Method (e) are novel compounds and may be easily obtained for example by reacting the phthalic anhydrides of the formula (XII) above with the compounds of the formula (III) above.

The reaction between the above compounds may be conducted in a suitable diluent. The diluent used therein may be, for example, aliphatic, cycloaliphatic and aromatic hydrocarbons (optionally chlorinated) such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as ethylether, methylethylether, isopropylether, butylether, dioxane, dimethoxyethane (DME), tetrahydrofuran (THF), diethyleneglycoldimethylether (DGM) and so on; ketones such as acetone, methylethylketone (MEK), methylisopropylketone, methylisobutylketone (MIBK) and so on; nitriles such as acetonitrile, propionitrile, acrylonitrile and so on; esters such as ethyl acetate, amyl acetate and so on.

The above reaction may be conducted in the presence of a base, examples of such base being tertiary amines, dialkylaminoanilines and pyridines such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ene (DBU) and so on.

The above reaction may be carried out in a substantially wide temperature range, but generally between about −70 and about 100° C., preferably between about −50 and about 80° C. Desirably, the reaction should be carried out under normal pressure but optionally it may be operated under increased or reduced pressure.

The following may be given as representative examples of the compound of the formula (VIII) above:
N-[4-(3,5-bis-trifluoromethyl-benzyl)-2-methyl-phenyl]-6-iodo-phthalamic acid,
6-chloro-N-[4-(3,5-bis-trifluoromethyl-benzyl)-2-methyl-phenyl]-phthalamic acid and so on.

The compounds of the formula (V) used as the starting material in Method (e) may be the same as that used in Methods (b) and (d) above.

The compounds of the formula (If) which are used as the starting material in Method (f) are compounds encompassed by the formula (I) of the present invention. The compounds of the formula (I), wherein $R^{1f}$ corresponds to $C_{1-6}$ alkylsulfinyl-$C_{1-6}$ alkyl or $C_{1-6}$ alkylsulfonyl-$C_{1-6}$ alkyl, may be obtained by oxidizing $C_{1-6}$ alkylthio-$C_{1-6}$ alkyl which are $R^{1f}$ of formula (If).

The compounds of the formula (If) may be prepared according to the methods as described in Method (a), (b), (c), (d) and/or (e).

The representative examples of the compounds of the formula (If) are:
3-iodo-$N^2$-(1-methyl-2-methylthioethyl)-$N^1$-[2-methyl-4-(3,5-bis-trifluoromethylbenzyl)-phenyl]-phthalamide,
$N^2$-(1,1-dimethyl-2-methylthioethyl)-3-iodo-$N^1$-[2-methyl-4-(3,5-bis-trifluoromethylbenzyl)-phenyl]-phthalamide,
3-iodo-$N^2$-(1-methyl-2-methylthioethyl)-$N^1$-[2-methyl-4-(3,5-bis-trifluoromethylbenzyl)-phenyl]-phthalamide,
3-chloro-$N^2$-(1-methyl-2-methylthioethyl)-$N^1$-[2-methyl-4-(3,5-bis-trifluoromethylbenzyl)-phenyl]-phthalamide,
3-chloro-$N^2$-(1-methyl-2-methylthioethyl)-$N^1$-[2-methyl-4-(3,4-bis-pentafluoroethylbenzyl)-phenyl]-phthalamide,
3-chloro-$N^2$-(1-methyl-2-methylthioethyl)-$N^{1[}$2-methyl-4-(3,5-bis-pentafluoroethylbenzyl)-phenyl]-phthalamide,
3-chloro-$N^2$-(1-methyl-2-methylthioethyl)-$N^1$-[2-methyl-4-(4-iso-perfluoropropylbenzyl)-phenyl]-phthalamide,
3-chloro-$N^2$-(1-methyl-2-methylthioethyl)-$N^1$-[2-methyl-4-(3,5-dichlorobenzyl)-phenyl]-phthalamide, 3-chloro-N²-(1-methyl-2-methylthioethyl)-N¹-[2-methyl-4-(2,6-bis-pentafluoroethyl-pyridin-4-ylmethyl)-phenyl]-phthalamide and so on.

The reaction of Method (a) above may be conducted in a suitable diluent singly or in mixture. Examples of the diluent are water; aliphatic, cycloaliphatic and aromatic hydrocarbons (optionally chlorinated) such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as ethylether, methylethylether, isopropylether, butylether, dioxane, dimethoxyethane (DME), tetrahydrofuran diethyleneglycoldimethylether (DGM) and the like; nitriles such as acetonitrile, propionitrile, acrylonitrile and so on; esters such as ethyl acetate, amyl acetate and so on.

Method (a) may be carried out in the presence of an acid catalyst, examples of such acid catalyst being inorganic acids such as hydrochloric acid and sulfuric acid; organic acids such as acetic acid, trifluoro acetic acid, propionic acid, methanesulfonic acid, benzensulfonic acid, p-toluenesulfonic acid and the like.

Method (a) may be carried out in a substantially wide temperature range, but generally between about −20 and about 100° C., preferably between about 0 and about 100° C. Desirably, the reaction should be carried out under normal pressure but optionally it may be operated under increased or reduced pressure.

In conducting Method (a), the target compounds of the formula (I) may be obtained by, for example, reacting one mol of the compounds of the formula (II) with one mol or a few excess mols of the compounds of the formula (III) in the presence of 0.01-0.1 mol of p-toluenesulfonic acid in a diluent such as 1,2-dichloroethane.

The reaction of Method (b) above may be carried out in a suitable diluent, examples of such diluent being aliphatic, cycloaliphatic and aromatic hydrocarbons (optionally chlorinated) such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and so on; ethers such as ethylether, methylethylether, isopropylether, butylether, dioxane, dimethoxyethane (DME), tetrahydrofuran (THF), diethyleneglycoldimethylether (DGM) and so on; esters such as ethyl acetate, amyl acetate and so on; acid amides such as dimethylformamide (DMF), dimethylacetoamide (DMA), N-methylpyrrolidone, 1,3-dimethyl-2-imidazolidinone, hexamethylphosphorictriamide (HMPA) and so on.

Method (b) may be carried out in the presence of an acid catalyst, examples of such acid catalyst including inorganic acids such as hydrochloric acid and sulfuric acid; organic acids such as acetic acid, trifluoro acetic acid, propionic acid, methanesulfonic acid, p-toluenesulfonic acid and the like.

Method (b) may be conducted in a substantially wide temperature range, but generally between about −20 and about 150° C., preferably between room temperature and about 100° C. Desirably, the reaction should be carried out under normal pressure but optionally it may be operated under increased or reduced pressure.

In carrying out Method (b), the target compounds of the formula (I) may be obtained for example by reacting one mol of the compounds of the formula (IV) with 1-25 mol of the compounds of the formula (V) in the presence of 0.01-0.5 mol of acetic acid in a diluent such as dioxane.

Methods (c), (d) and (e) may be conducted under the same conditions as Method (a) above.

The reaction of Method (f) above may be carried out in a suitable diluent. Examples of such diluent may include aliphatic, cycloaliphatic and aromatic hydrocarbons (optionally chlorinated) such as benzene, toluene, xylene, dichloromethane, chloroform, carbon tetrachloride, 1,2-dichloroethane, chlorobenzene, dichlorobenzene etc.; alcohols such as methanol, ethanol, isopropanol, butanol etc.; acids such as formic acid, acetic acid and so on.

The oxidant used in Method (f) above may be, for example, metachloroperbenzoic acid, peracetic acid, potassium metaperiodate, potassium hydrogen persulfate (oxon), hydrogen peroxide and so on.

Method (f) may be conducted in a substantially wide temperature range, but generally between about −50 and about 150° C., preferably between −10 and about 100° C. Desirably, the reaction should be carried out under normal pressure but optionally it may be operated under increased or reduced pressure.

In carrying out Method (f), the target compounds of the formula (I) may be obtained by reacting one mol of the compounds of the formula (If) with 1-5 mol of oxidant in a diluent such as dichloromethane.

The reaction of Method (f) may be conducted according to the method described in Jikken Kagaku Koza (Experimental Chemistry), Japan Chemical Society 4th Edition, Vol. 24, pp. 350, 1992 published by Maruzen or pp. 365 of the same.

The active compounds according to the invention are well tolerated by plants, have favourable toxicity to warm-blooded species, show good environmental compatibility and are suitable for protecting plants and plant organs, for increasing yields, improving the quality of the yield and for controlling animal pests, in particular insects, arachnids, helminths, nematodes and molluscs, which are found in agriculture, horticulture, in animal breeding, in forests, in gardens and leisure facilities, in the protection of stored products and materials and in the hygiene sector. They can preferably be employed as plant protection agents. They are active against normally sensitive and resistant species and against all or individual developmental stages. The abovementioned pests include:

From the order of the Anoplura (Phthiraptera), for example *Damalinia* spp., *Haematopinus* spp., *Linognathus* spp., *Pediculus* spp., *trichodectes* spp.

From the class of the Arachnida, for example *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example *Dreissena* spp.

From the order of the Chilopoda, for example *Geophilus* spp., *Scutigera* spp.

From the order of the Coleoptera, for example *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna con-* sanguinea, Leptinotarsa decemlineata, Lissorhoptrus oryzophilus, Lixus spp., Lyctus spp., Meligethes aeneus, Melolontha melolontha, Migdolus spp., Monochamus spp., Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga spp., Popillia japonica, Premnotrypes spp., Psylliodes chrysocephala, Ptinus spp., Rhizobius ventralis, Rhizopertha dominica, Sitophilus spp., Sphenophorus spp., Sternechus spp., Symphyletes spp., Tenebrio molitor, Tribolium spp., Trogoderma spp., Tychius spp., Xylotrechus spp., Zabrus spp.

From the order of the Collembola, for example *Onychiurus armatus*.

From the order of the *Dermaptera*, for example *Forficula auricularia*.

From the order of the Diplopoda, for example *Blaniulus guttulatus*.

From the order of the Diptera, for example *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*.

From the class of the Gastropoda, for example *Anion* spp., *Biomphalaria* spp., *Bulinus* spp., *Deroceras* spp., *Galba* spp., *Lymnaea* spp., *Oncomelania* spp., *Succinea* spp.

From the class of the Helminths, for example *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

Protozoans such as *Eimeria* can also be controlled.

From the order of the Heteroptera, for example *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *triatoma* spp.

From the order of the Homoptera, for example *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *trialeurodes vaporariorum*, *trioza* spp., *Typhlocyba* spp., *Unaspis* spp., *Viteus vitifolii*.

From the order of the *Hymenoptera*, for example *Diprion* spp., *Hoplocampa* spp., *Lasius* spp., *Monomorium pharaonis*, *Vespa* spp.

From the order of the Isopoda, for example *Armadillidium vulgare*, *Oniscus asellus*, *Porcellio scaber*.

From the order of the *Isoptera*, for example *Reticulitermes* spp.

From the order of the *Lepidoptera*, for example *Acronicta major*, *Aedia leucomelas*, *Agrotis* spp., Alabama *argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *trichoplusia* spp.

From the order of the Orthoptera, for example *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example *Ceratophyllus* spp., *Xenopsylla cheopis*.

From the order of the Symphyla, for example *Scutigerella immaculate*.

From the order of the Thysanoptera, for example *Baliothrips biformis*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Thysanura, for example *Lepisma saccharina*.

The plant-parasitic nematodes include, for example, *Aphelenchoides* spp., *Bursaphelenchus* spp., *Ditylenchus dipsaci*, *Globodera* spp., *Heterodera* spp., *Longidorus* spp., *Meloidogyne* spp., *Pratylenchus* spp., *Radopholus similis*, trichodorus spp., *Tylenchulus semipenetrans, Xiphinema* spp.

In certain concentrations or application rates, the compounds according to the invention can, if appropriate, also be used as herbicides, safeners, growth regulators or agents for improving the plant characteristics, or as microbicides, for example as fungicides, antimycotics, bactericides, virucides (including as agents against viroids) or as agents against MLOs (Mycoplasma-like organisms) and RLOs (Rickettsia-like organisms). They can also be employed as intermediates or precursors for the synthesis of further active compounds if appropriate.

All plants and plant parts can be treated in accordance with the invention. In this context, plants are understood as meaning all plants and plant populations, such as desired and undesired wild plant or crop plants (including naturally occurring crop plants). Crop plants may be plants which can be obtained by conventional breeding and optimization methods or by biotechnological and genetic-engineering methods or by combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

The treatment according to the invention of the plants and plant parts with the active compounds is carried out directly or by acting on their environment, habitat or store, using customary treatment methods, for example by immersion, spraying, vaporizing, fogging, broadcasting, painting on, injecting and, in the case of propagation material, in particular in the case of seeds, furthermore by coating with one or more coats.

The active compounds can be converted into the customary formulations, such as solutions, emulsions, wettable powders, water- and oil-based suspensions, powders, dusts, pastes, soluble powders, soluble granules, granules, for broadcasting, suspoemulsion concentrates, natural materials impregnated with active compounds, synthetic materials impregnated with active compounds, fertilisers and microencapsulations in polymeric materials.

These formulations are produced in a known manner, for example by mixing the active compounds with extenders, that is, liquid solvents and/or solid carriers, optionally with the use of surface-active agents, that is, emulsifiers and/or dispersants and/or foam formers.

If water is used as extender, auxiliary solvents which can also be used are, for example, organic solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters, ketones, such as acetone, methyl ethyl ketone, methyl isobutyl ketone or cyclohexanone, strongly polar solvents, such as dimethyl sulphoxide, and water.

As solid carriers there are suitable:
for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; as emulsifiers and/or foam formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; as dispersants there are suitable: for example lignosulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The active compounds according to the invention, in commercially available formulations and in the use forms prepared from these formulations, can be present in a mixture with other known active compounds such as insecticides, attractants, sterilants, bactericides, acaricides, nematicides, fungicides, growth regulators or herbicides, safeners, fertilizers or semiochemicals.

Examples of especially advantageous components in the mixtures are the following:
Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chloro-thalonil; chlozolinate; clozylacon; cyazofamid; cyflufenamid; cymoxanil; cyproconazole; cyprodinil; cyprofuram; Dagger G; debacarb; dichiofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-m; dinocap; diphenylamine; dipyrithione; ditalimfos; dithianon; dodine; drazoxolon; edifenphos; epoxiconazole; ethaboxam; ethirimol; etridiazole; fam-oxadone; fenamidone; fenapanil; fenarimol; fenbuconazole; fenfuram; fenhexamid; fenitropan; fenoxanil; fenpiclonil; fenpropidin; fenpropimorph; ferbam;

fluazinam; flubenzimine; fludioxonil; flumetover; flumorph; fluoromide; fluoxastrobin; fluquinconazole; flurprimidol; flusilazole; flusulphamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpo-conazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; tri-flumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridincarboxamide; 3,4,5-trichloro-2,6-pyridinedicarbonitrile; actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro-[4.5]decan-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations:

Insecticides/Acaricides/Nematicides:
Acetylcholin Esterase (AChE) Inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chloropyrifos(-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-dependent Sodium Channel Blockers
pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, trans-fluthrin, ZXI 8901, pyrethrins (pyrethrum)
DDT
oxadiazines,
for example indoxacarb Acetylcholin Receptor Agonists/Antagonists
Chloronicotinyls,
for example acetamiprid, clothianidin, dinotefuran, imidacloprid, nitenpyram, nithiazine, thiacloprid, thiamethoxam
nicotine, bensultap, cartap Acetylcholin Receptor Modulators
spinosyns,
for example spinosad GABA-controlled Chloride Channel Antagonists
organochlorins,
for example camphechlor, chlordane, endosulphan, gamma-HCH, HCH, heptachlor, lindane, methoxychlor
fiprols,
for example acetoprole, ethiprole, fipronil, pyrafluprole, pyriprole, vaniliprole Chloride Channel Activators
mectins,
for example lepimectin, abamectin, avermectin, emamectin, emamectin-benzoate, ivermectin, milbemycin Juvenile Hormone Mimetics,
for example diofenolan, epofenonane, fenoxycarb, hydroprene, kinoprene, methoprene, pyriproxifen, triprene Ecdysone Agonists/Disruptors
diacylhydrazines,
for example chromafenozide, halofenozide, methoxyfenozide, tebufenozide
Chitin Biosynthesis Inhibitors
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine
Inhibitors of Oxidative Phosphorylation, ATP Disruptors
diafenthiuron
organotin compounds
for example azocyclotin, cyhexatin, fenbutatin-oxide
Uncouplers of Oxidative Phoshorylation by Interrupting the H Proton Gradient
pyrroles,
for example chlorfenapyr
dinitrophenols,
for example binapacyrl, dinobuton, dinocap, DNOC
Site-I Electron Transport Inhibitors
METI's,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Fat Biosynthesis Inhibitors
tetronic acids,
for example spirodiclofen, spiromesifen
tetramic acids,
for example spirotetramat (CAS-Reg.-No.: 203313-25-1) and 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS-Reg.-No.: 382608-10-8), cis-3-(2,5-dimethylphenyl)-4-hydroxy-8-methoxy-1-aspiro[4.5]dec-3-en-2-one
carboxamide,
for example flonicamid
octopaminergic agonists,
for example amitraz
Inhibitors of Magnesium-stimulated ATPase,
propargite
benzoic acid dicarboxamides,
for example flubendiamide
anthranilic acid amides,
for example Rynaxypyr
nereistoxin analogues,
for example thiocyclam hydrogen oxalate, thiosultap-sodium
Biologicals, Hormones or Pheromones
azadirachtin, *Bacillus* spec., *Beauveria* spec., codlemone, *Metarrhizium* spec., *Paecilomyces* spec., Thuringiensin, *Verticillium* spec.
Active Compounds with Unknown or Unspecific Mechanisms of Action
fumigants,
for example aluminium phosphide, methyl bromide, sulphuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chino-methionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds such as herbicides, fertilizers, growth regulators, safeners, semiochemicals or else with agents which improve the plant characteristics, is also possible.

When used as insecticides, the active compounds according to the invention can furthermore be present, in their commercially available formulations and in the use forms prepared from these formulations as mixtures with synergists. Synergists are compounds by which the activity of the active compound is enhanced without it being necessary for the synergist added to be active itself.

When used as insecticides, the active compounds according to the invention can furthermore be present, in their commercially available formulations and in the use forms prepared from these formulations, as mixtures with inhibitors which reduce degradation of the active compound post-application in the environment of the plant, on the surface of plant parts or in plant tissues.

The active compound content of the use forms prepared from the commercially available formulations can vary within wide limits. The active compound concentration of the use forms can be from 0.00000001 up to 95% by weight of active compound, preferably between 0.00001 and 1% by weight.

Application is effected in a customary manner which is adapted to suit the use forms.

As already mentioned above, all plants and their parts can be treated in accordance with the invention. In a preferred use form, plant species and plant varieties, and their parts, which are found in the wild or which are obtained by conventional biological breeding methods, such as hybridization or protoplast fusion, are treated. In a further preferred embodiment, transgenic plants and plant varieties, and their parts, which have been obtained by genetic engineering methods, if appropriate in combination with traditional methods (genetically modified organisms) are treated. The terms "parts", "parts of plants" or "plant parts" have been detailed above.

It is especially preferred to treat, in accordance with the invention, plants of the plant varieties which are in each case commercially available or in use. Plant cultivars are understood as meaning plants with new properties ("traits") which have been obtained by conventional cultivation, by mutagenesis or else by recombinant DNA techniques. These may be cultivars, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or widenings of the activity spectrum and/or an increase in the activity of the substances and compositions that can be used according to the invention, better plant growth, increased tolerance to high or low temperatures, increased tolerance of the crop plants to drought or to water or soil salinity, increased flowering performance, easier harvesting, accelerated maturation, higher yields, better quality and/or a higher nutritional value of the harvested products, better storage stability and/or processability of the harvested products which exceed the effects which were actually to be expected are possible.

The preferred transgenic plants or plant cultivars (i.e. those obtained by genetic engineering) which are to be treated according to the invention include all plants which, by genetic modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetables, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defense of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defense of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosates or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example corn), StarLink® (for example corn), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya beans), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant varieties having these genetic traits or genetic traits, which will be developed in the future, which varieties will be developed and/or marketed in the future.

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention are not only active against plant pests, hygiene pests and stored-product pests, but also, in the sector of veterinary medicine, against animal parasites (ecto- and endoparasites) such as hard ticks, soft ticks, scab mites, harvest mites, flies (stinging and licking), parasitic fly larvae, lice, hair lice, bird lice and flees. These parasites include:

From the order of the Anoplurida, for example *Haematopinus* spp., *Linognathus* spp., *Pediculus* spp., *Phtirus* spp., *Solenopotes* spp.

From the order of the Mallophagida and the suborders Amblycerina and Ischnocerina, for example *trimenopon* spp., *Menopon* spp., *trinoton* spp., *Bovicola* spp., *Werneckiella* spp., *Lepikentron* spp., *Damalina* spp., *trichodectes* spp., *Felicola* spp.

From the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example *Pulex* spp., *Ctenocephalides* spp., *Xenopsylla* spp., *Ceratophyllus* spp.

From the order of the Heteropterida, for example *Cimex* spp., *triatoma* spp., *Rhodnius* spp., *Panstrongylus* spp.

From the order of the Blattarida, for example *Blatta orientalis, Periplaneta americana, Blattela germanica, Supella* spp.

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula I according to the invention are also suitable for controlling arthropods which attack agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods, it is intended to reduce deaths and reduce performance (in the case of meat, milk, wool, hides, eggs, honey and the like), so that more economical and simpler animal keeping is made possible by the use of the active compounds according to the invention.

In the veterinary sector and in animal keeping, they are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When used for livestock; poultry, domestic animals and the like, the active compounds of the formula I can be applied as formulations (for example powders, emulsions, flowables) which comprise the active compounds in an amount of from 1 to 80% by weight, either directly or after 100- to 10000-fold dilution, or else as a chemical bath.

Furthermore, it has been found that the active compounds according to the invention have a potent insecticidal activity against insects which destroy industrial materials.

The following insects may be mentioned by way of example and by preference, but not by limitation:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Heminoptera such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccharina.*

Industrial materials are understood as meaning, in the present context, non-live materials such as, preferably, polymers, adhesives, glues, paper and board, leather, wood, derived timber products and paints.

If appropriate, the ready-to-use compositions may additionally comprise further insecticides and, if appropriate, additionally one or more fungicides.

As regards potential additional components in mixtures, reference may be made to the abovementioned insecticides and fungicides.

The compounds according to the invention can also be employed for protecting growths on objects, in particular ships' hulls, sieves, nets, buildings, moorings and signal systems which come into contact with salt water or brackish water.

Furthermore, the compounds according to the invention, alone or in combinations with other active compounds, may be employed as antifouling agents.

The active compounds are also suitable for controlling animal pests in the protection of domestic premises, in the field of hygiene and of stored products, in particular insects, arachnids and mites which are found in enclosed spaces such as for example, dwellings, factory halls, offices, drivers' cabins and the like. To control these pests they can be used in insecticidal products for domestic premises, either alone or in combination with other active compounds and auxiliaries. They are active against sensitive and resistant species and against all developmental stages. These pests include:

From the order of the Scorpionidea, for example *Buthus occitanus.*

From the order of the Acarina, for example *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example *Aviculariidae, Araneidae.*

From the order of the Opiliones, for example *Pseudoscorpiones chelifer, Pseudoscorpiones cheiridium, Opiliones phalangium.*

From the order of the Isopoda, for example *Oniscus asellus, Porcellio scaber.*

From the order of the Diplopoda, for example *Blaniulus guttulatus, Polydesmus* spp.

From the order of the Chilopoda, for example *Geophilus* spp.

From the order of the Zygentoma, for example *Ctenolepisma* spp., *Lepisma saccharina, Lepismodes inquilinus.*

From the order of the Blattaria, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example *Acheta domesticus.*

From the order of the *Dermaptera,* for example *Forficula auricularia.*

From the order of the *Isoptera*, for example *Kalotermes* spp., *Reticulitermes* spp.

From the order of the Psocoptera, for example *Lepinatus* spp., *Liposcelis* spp.

From the order of the Coleoptera, for example *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the *Lepidoptera*, for example *Achroia grisella*, *Galleria mellonella*, *Plodia interpunctella*, *Tinea cloacella*, *Tinea pellionella*, *Tineola bisselliella*.

From the order of the *Siphonaptera*, for example *Ctenocephalides canis*, *Ctenocephalides fells*, *Pulex irritans*, *Tunga penetrans*, *Xenopsylla cheopis*.

From the order of the *Hymenoptera*, for example *Camponotus herculeanus*, *Lasius fuliginosus*, *Lasius niger*, *Lasius umbratus*, *Monomorium pharaonis*, *Paravespula* spp., *Tetramorium caespitum*.

From the order of the *Anoplura*, for example *Pediculus humanus capitis*, *Pediculus humanus corporis*, *Phthirus pubis*.

From the order of the *Heteroptera*, for example *Cimex hemipterus*, *Cimex lectularius*, *Rhodinus prolixus*, *Triatoma infestans*.

The application in the field of the domestic insecticides may also be carried out alone or in combination with other suitable active compounds such as phosphoric esters, carbamates, pyrethroids, neo-nicotinoids, growth regulators or active compounds from other known classes of insecticides.

The application is carried out in aerosols, unpressurized sprays, for example pump sprays and atomizer sprays, automatic misting devices, foggers, foams, gels, vaporizer products with vaporizer platelets made of cellulose or polymer, liquid vaporizers, gel and membrane vaporizers, propeller-driven vaporizers, vaporization systems which do not consume energy (passive vaporization systems), moth papers, moth sachets and moth gels in the form of granules or dusts, in baits for scattering or bait stations.

The preparation and the use of the substances according to the invention can be seen from the examples which follow.

EXAMPLES

The present invention is more specifically explained using the following examples. The examples are not intended to limit the present invention.

Synthesis Example 1

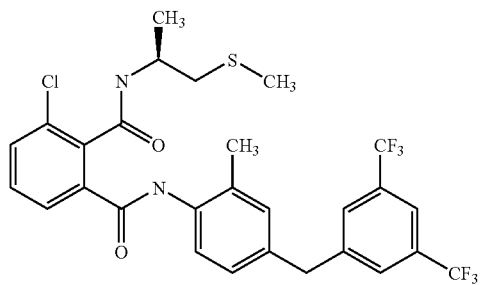

4-Chloro-3-[(S)-1-methyl-2-methylthioethylimino]-3-H-isobenzofuran-1-one (0.2 g) and 4-(3,5-bis-trifluoromethyl-benzyl)-2-methylaniline (0.22 g) were dissolved in acetonitrile (10 ml), to which p-toluenesulfonic acid hydrate (0.01 g) was added, and then stirred at room temperature for three hours. After the reaction, the solvent was distilled off under reduced pressure and the resultant residue was purified by silica gel column chromatography to obtain $N^1$-[4-(3,5-bis-trifluoromethyl-benzyl)-2-methylphenyl]-3-chloro-$N^2$-(S)-1-methyl-2-methylthioethyl)phthalamide (0.10 g).

Melting point: 57-62° C.

Synthesis Eample 2

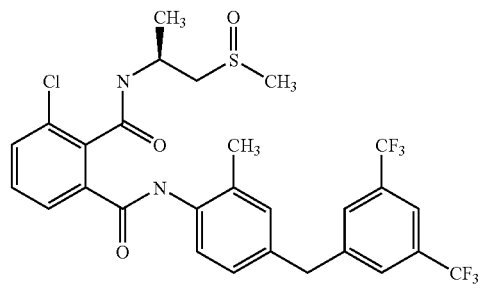

$N^1$[4-(3,5-bis-trifluoromethyl-benzyl)-2-methylphenyl]-3-chloro-$N^2$-((S)-1-methyl-2-methylsulfanyl-ethyl)phthalamide (0.19 g) was dissolved in methylene chloride, to which m-chloroperbenzoic acid (0.08 g) was added, and stirred at room temperature for 3 hours. After the reaction, it was washed with a sodium thiosulfate solution, a saturated sodium bicarbonate solution and a saturated salt solution, and the organic layer was dried over anhydrous magnesium sulfate.

The solvent was distilled off under reduced pressure and the resultant residue was purified by silica gel column chromatography to obtain $N^1$-[4-(3,5-bis-trifluoromethyl-benzyl)-2-methylphenyl]-3-chloro-$N^2$-(2-methanesulfinyl-(S)-1-methyl-ethyl)phthalamide (0.12 g).

Melting point: 162-165° C.

Synthesis Example 3

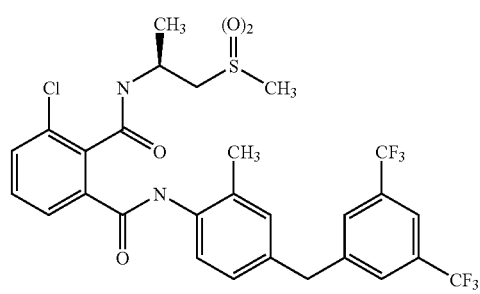

$N^1$-[4-(3,5-bis-trifluoromethyl-benzyl)-2-methylphenyl]-3-chloro-$N^2$-(S)-1-methyl-2-methylsulfanyl-ethyl)phthalamide (0.22 g) was dissolved in methylene chloride, to which m-chloroperbenzoic acid (0.20 g) was added, and stirred at room temperature for 3 hours. After the reaction was finished, it was washed with a sodium thiosulfate solution, a saturated sodium bicarbonate solution and a saturated salt solution, and the organic layer was dried over anhydrous magnesium sulfate. The solvent was distilled off under reduced pressure and the resultant residue was purified by silica gel column chromatography to obtain $N^1$-[4-(3,5-bis-trifluoromethyl-benzyl)-2-methylphenyl]-3-chloro-$N^2$-(2-methanesulfonyl-(S)-1-methyl-ethyl)phthalamide (0.10 g)

Melting point: 155-158° C. .

Synthesis Example 4

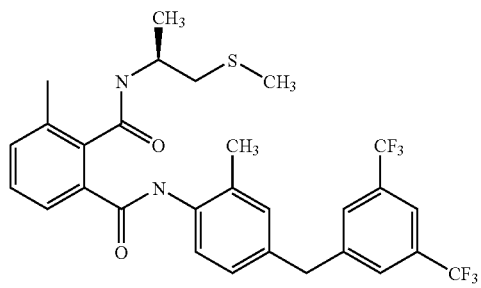

3-Iodo-N-((S)-1-methyl-2-methylthioethyl)-phthalamic acid (0.38 g) and N-(3-dimethylaminopropyl)-N'-ethylcarbonyldimidazole hydrochloride (0.2 g) were stirred in methylene chloride (10 ml) at room temperature for 30 minutes. 4-(3,5-Bis-trifluoromethyl-benzyl)-2-methylaniline (0.3 g) and p-toluenesulfonic acid hydrate (0.02 g) were added thereto and stirred at room temperature for 3 hours. After the reaction, the solvent was distilled off under reduced pressure and the resultant residue was purified by silica gel column chromatography to obtain $N^1$-[4-(3,5-bis-trifluoromethyl-benzyl)-2-methylphenyl]-3-iodo-$N^2$-((S)-1-methyl-2-methylthioethyl) phthalamide (0.15 g).

Melting point: 85-94° C.

Synthesis Example 5

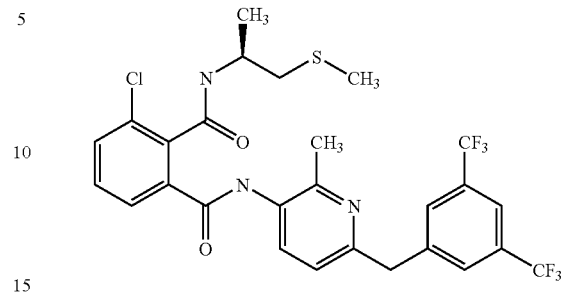

4-Chloro-3-[(S)-1-methyl-2-methylthioethylimino]-3-H-isobenzofuran-1-one (0.2 g) and 6-(3,5-bis-trifluoromethyl-benzyl)-2-methyl-pyridin-3-ylamine (0.22 g) were dissolved in acetonitrile (10 ml), to which p-toluenesulfonic acid hydrate (0.01 g) was added, and stirred at 60° C. for 20 hours. After the reaction, the solvent was distilled off under reduced pressure and the resultant residue was purified by silica gel column chromatography to obtain $N^1$-[6-3,5-bis-trifluoromethyl-benzyl)-2-methyl-pyridin-3-yl]-3-chloro-$N^2$-(S)-1-methyl-2-methylhioethyl)phthalamide (0.21 g).

Melting point: 73-79° C.

The compounds of the formula (I) of the present invention that may be obtained by the methods similar to the above synthesis examples are indicated in Tables 1 to 8 below, together with the compounds obtained in the above synthesis examples.

TABLE 1

| | R1 | R2 | R3 | X | Y | Z1 | Z2 | Z3 | Z4 | Z5 | mp |
|---|---|---|---|---|---|---|---|---|---|---|---|
| 1 | CH(CH3)CH2SCH3(S) | H | H | 3-Cl | 2-CH3 | H | CF3 | H | H | H | 160-162 |
| 2 | CH(CH3)CH2SOCH3(S) | H | H | 3-Cl | 2-CH3 | H | CF3 | H | H | H | |
| 3 | CH(CH3)CH2SO2CH3(S) | H | H | 3-Cl | 2-CH3 | H | CF3 | H | H | H | |
| 4 | C(CH3)2CH2SCH3 | H | H | 3-Cl | 2-CH3 | H | CF3 | H | H | H | |
| 5 | C(CH3)2CH2SOCH3 | H | H | 3-Cl | 2-CH3 | H | CF3 | H | H | H | |
| 6 | C(CH3)2CH2SO2CH3 | H | H | 3-Cl | 2-CH3 | H | CF3 | H | H | H | |
| 7 | CH(CH3)CH2SCH3 | H | H | 3-Cl | 2-CH3 | H | H | CF3 | H | H | |
| 8 | CH(CH3)CH2SCH3(S) | H | H | 3-Cl | 2-CH3 | H | H | CF3 | H | H | 66-70 |
| 9 | CH(CH3)CH2SOCH3(S) | H | H | 3-Cl | 2-CH3 | H | H | CF3 | H | H | |
| 10 | CH(CH3)CH2SO2CH3(S) | H | H | 3-Cl | 2-CH3 | H | H | CF3 | H | H | |
| 11 | CH(CH3)CH2SC2H5(S) | H | H | 3-Cl | 2-CH3 | H | H | CF3 | H | H | |
| 12 | C(CH3)2CH2SCH3 | H | H | 3-Cl | 2-CH3 | H | H | CF3 | H | H | |
| 13 | C(CH3)2CH2SOCH3 | H | H | 3-Cl | 2-CH3 | H | H | CF3 | H | H | |
| 14 | C(CH3)2CH2SO2CH3 | H | H | 3-Cl | 2-CH3 | H | H | CF3 | H | H | |
| 15 | iso-Pr | H | H | 3-Cl | 2-CH3 | H | CF3 | H | CF3 | H | |
| 16 | CH(CH3)CH2SCH3 | H | H | 3-Cl | 2-CH3 | H | CF3 | H | CF3 | H | |
| 17 | CH(CH3)CH2SOCH3 | H | H | 3-Cl | 2-CH3 | H | CF3 | H | CF3 | H | |
| 18 | CH(CH3)CH2SO2CH3 | H | H | 3-Cl | 2-CH3 | H | CF3 | H | CF3 | H | |
| 19 | CH(CH3)CH2SCH3(S) | H | H | 3-Cl | 2-CH3 | H | CF3 | H | CF3 | H | 57-62 |
| 20 | CH(CH3)CH2SOCH3(S) | H | H | 3-Cl | 2-CH3 | H | CF3 | H | CF3 | H | 162-165 |
| 21 | CH(CH3)CH2SO2CH3(S) | H | H | 3-Cl | 2-CH3 | H | CF3 | H | CF3 | H | 155-158 |
| 22 | CH(CH3)CH2SCH3(R) | H | H | 3-Cl | 2-CH3 | H | CF3 | H | CF3 | H | |
| 23 | CH(CH3)CH2SOCH3(R) | H | H | 3-Cl | 2-CH3 | H | CF3 | H | CF3 | H | |

TABLE 1-continued

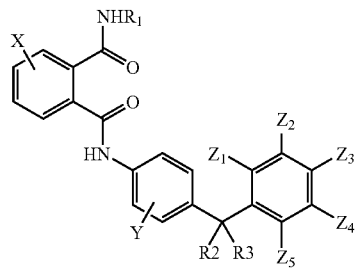

| | R1 | R2 | R3 | X | Y | Z1 | Z2 | Z3 | Z4 | Z5 | mp |
|---|---|---|---|---|---|---|---|---|---|---|---|
| 24 | CH(CH3)CH2SO2CH3(R) | H | H | 3-Cl | 2-CH3 | H | CF3 | H | CF3 | H | |
| 25 | CH(CH3)CH2SC2H5(S) | H | H | 3-Cl | 2-CH3 | H | CF3 | H | CF3 | H | |
| 26 | CH(CH3)CH2SOC2H5(S) | H | H | 3-Cl | 2-CH3 | H | CF3 | H | CF3 | H | |
| 27 | CH(CH3)CH2SO2C2H5(S) | H | H | 3-Cl | 2-CH3 | H | CF3 | H | CF3 | H | |
| 28 | C(CH3)2CH2SCH3 | H | H | 3-Cl | 2-CH3 | H | CF3 | H | CF3 | H | |
| 29 | C(CH3)2CH2SOCH3 | H | H | 3-Cl | 2-CH3 | H | CF3 | H | CF3 | H | |
| 30 | C(CH3)2CH2SO2CH3 | H | H | 3-Cl | 2-CH3 | H | CF3 | H | CF3 | H | |
| 31 | CH(CH3)CH2SCH3 | H | H | 3-Cl | 2-CH3 | H | CF3 | H | CF3 | H | |
| 32 | CH(CH3)CH2SCH3(S) | H | H | 3-Cl | 2-CH3 | H | CF3 | H | CF3 | H | |
| 33 | CH(CH3)CH2SOCH3(S) | H | H | 3-Cl | 2-CH3 | H | CF3 | H | CF3 | H | |
| 34 | CH(CH3)CH2SO2CH3(S) | H | H | 3-Cl | 2-CH3 | H | CF3 | H | CF3 | H | |
| 35 | CH(CH3)CH2SC2H5(S) | H | H | 3-Cl | 2-CH3 | H | CF3 | H | CF3 | H | |
| 36 | C(CH3)2CH2SCH3 | H | H | 3-Cl | 2-CH3 | H | CF3 | H | CF3 | H | |
| 37 | C(CH3)2CH2SOCH3 | H | H | 3-Cl | 2-CH3 | H | CF3 | H | CF3 | H | |
| 38 | C(CH3)2CH2SO2CH3 | H | H | 3-Cl | 2-CH3 | H | CF3 | H | CF3 | H | |
| 39 | CH(CH3)CH2SCH3(S) | H | H | 3-Cl | 2-CH3 | CF3 | H | CF3 | H | H | 80-85 |
| 40 | CH(CH3)CH2SOCH3(S) | H | H | 3-Cl | 2-CH3 | CF3 | H | CF3 | H | H | |
| 41 | CH(CH3)CH2SO2CH3(S) | H | H | 3-Cl | 2-CH3 | CF3 | H | CF3 | H | H | |
| 42 | CH(CH3)CH2SCH3(S) | H | H | 3-Cl | 2-CH3 | H | C2F5 | H | H | H | |
| 43 | CH(CH3)CH2SOCH3(S) | H | H | 3-Cl | 2-CH3 | H | C2F5 | H | H | H | |
| 44 | CH(CH3)CH2SO2CH3(S) | H | H | 3-Cl | 2-CH3 | H | C2F5 | H | H | H | |
| 45 | CH(CH3)CH2SCH3(S) | H | H | 3-Cl | 2-CH3 | H | H | C2F5 | H | H | |
| 46 | CH(CH3)CH2SOCH3(S) | H | H | 3-Cl | 2-CH3 | H | H | C2F5 | H | H | |
| 47 | CH(CH3)CH2SO2CH3(S) | H | H | 3-Cl | 2-CH3 | H | H | C2F5 | H | H | |
| 48 | CH(CH3)CH2SC2H5(S) | H | H | 3-Cl | 2-CH3 | H | H | C2F5 | H | H | |
| 49 | C(CH3)2CH2SCH3 | H | H | 3-Cl | 2-CH3 | H | H | C2F5 | H | H | |
| 50 | C(CH3)2CH2SOCH3 | H | H | 3-Cl | 2-CH3 | H | H | C2F5 | H | H | |
| 51 | C(CH3)2CH2SO2CH3 | H | H | 3-Cl | 2-CH3 | H | C2F5 | H | C2F5 | H | |
| 52 | iso-Pr | H | H | 3-Cl | 2-CH3 | H | C2F5 | H | C2F5 | H | |
| 53 | CH(CH3)CH2SCH3 | H | H | 3-Cl | 2-CH3 | H | C2F5 | H | C2F5 | H | |
| 54 | CH(CH3)CH2SOCH3 | H | H | 3-Cl | 2-CH3 | H | C2F5 | H | C2F5 | H | |
| 55 | CH(CH3)CH2SO2CH3 | H | H | 3-Cl | 2-CH3 | H | C2F5 | H | C2F5 | H | |
| 56 | CH(CH3)CH2SCH3(S) | H | H | 3-Cl | 2-CH3 | H | C2F5 | H | C2F5 | H | 82-87 |
| 57 | CH(CH3)CH2SOCH3(S) | H | H | 3-Cl | 2-CH3 | H | C2F5 | H | C2F5 | H | 82-87 |
| 58 | CH(CH3)CH2SO2CH3(S) | H | H | 3-Cl | 2-CH3 | H | C2F5 | H | C2F5 | H | 90-96 |
| 59 | CH(CH3)CH2SC2H5(S) | H | H | 3-Cl | 2-CH3 | H | C2F5 | H | C2F5 | H | |
| 60 | CH(CH3)CH2SOC2H5(S) | H | H | 3-Cl | 2-CH3 | H | C2F5 | H | C2F5 | H | |
| 61 | CH(CH3)CH2SO2C2H5(S) | H | H | 3-Cl | 2-CH3 | H | C2F5 | H | C2F5 | H | |
| 62 | C(CH3)2CH2SCH3 | H | H | 3-Cl | 2-CH3 | H | C2F5 | H | C2F5 | H | |
| 63 | C(CH3)2CH2SOCH3 | H | H | 3-Cl | 2-CH3 | H | C2F5 | H | C2F5 | H | |
| 64 | C(CH3)2CH2SO2CH3 | H | H | 3-Cl | 2-CH3 | H | C2F5 | H | C2F5 | H | |
| 65 | CH(CH3)CH2SCH3(S) | H | H | 3-Cl | 2-CH3 | H | C2F5 | C2F5 | H | H | 88-91 |
| 66 | CH(CH3)CH2SOCH3(S) | H | H | 3-Cl | 2-CH3 | H | C2F5 | C2F5 | H | H | 86-89 |
| 67 | CH(CH3)CH2SO2CH3(S) | H | H | 3-Cl | 2-CH3 | H | C2F5 | C2F5 | H | H | 82-85 |
| 68 | CH(CH3)CH2SC2H5(S) | H | H | 3-Cl | 2-CH3 | H | C2F5 | C2F5 | H | H | |
| 69 | C(CH3)2CH2SCH3 | H | H | 3-Cl | 2-CH3 | H | C2F5 | C2F5 | H | H | |
| 70 | CH(CH3)CH2SCH3(S) | H | H | 3-Cl | 2-CH3 | H | C3F7-n | H | H | H | |
| 71 | CH(CH3)CH2SOCH3(S) | H | H | 3-Cl | 2-CH3 | H | C3F7-n | H | H | H | |
| 72 | CH(CH3)CH2SO2CH3(S) | H | H | 3-Cl | 2-CH3 | H | C3F7-n | H | H | H | |
| 73 | CH(CH3)CH2SCH3 | H | H | 3-Cl | 2-CH3 | H | H | C3F7-n | H | H | |
| 74 | CH(CH3)CH2SCH3(S) | H | H | 3-Cl | 2-CH3 | H | H | C3F7-n | H | H | |
| 75 | CH(CH3)CH2SOCH3(S) | H | H | 3-Cl | 2-CH3 | H | H | C3F7-n | H | H | |
| 76 | CH(CH3)CH2SO2CH3(S) | H | H | 3-Cl | 2-CH3 | H | H | C3F7-n | H | H | |
| 77 | CH(CH3)CH2SC2H5(S) | H | H | 3-Cl | 2-CH3 | H | H | C3F7-n | H | H | |
| 78 | C(CH3)2CH2SCH3 | H | H | 3-Cl | 2-CH3 | H | H | C3F7-n | H | H | |
| 79 | CH(CH3)CH2SCH3 | H | H | 3-Cl | 2-CH3 | H | C3F7-n | H | C3F7-n | H | |
| 80 | CH(CH3)CH2SCH3(S) | H | H | 3-Cl | 2-CH3 | H | C3F7-n | H | C3F7-n | H | |
| 81 | CH(CH3)CH2SOCH3(S) | H | H | 3-Cl | 2-CH3 | H | C3F7-n | H | C3F7-n | H | |
| 82 | CH(CH3)CH2SO2CH3(S) | H | H | 3-Cl | 2-CH3 | H | C3F7-n | H | C3F7-n | H | |
| 83 | CH(CH3)CH2SC2H5(S) | H | H | 3-Cl | 2-CH3 | H | C3F7-n | H | C3F7-n | H | |
| 84 | C(CH3)2CH2SCH3 | H | H | 3-Cl | 2-CH3 | H | C3F7-n | H | C3F7-n | H | |
| 85 | CH(CH3)CH2SCH3(S) | H | H | 3-Cl | 2-CH3 | H | C3F7-i | H | H | H | |
| 86 | CH(CH3)CH2SOCH3(S) | H | H | 3-Cl | 2-CH3 | H | C3F7-i | H | H | H | |
| 87 | CH(CH3)CH2SO2CH3(S) | H | H | 3-Cl | 2-CH3 | H | C3F7-i | H | H | H | |
| 88 | CH(CH3)CH2SCH3(S) | H | H | 3-Cl | 2-CH3 | H | H | C3F7-i | H | H | 89-94 |

TABLE 1-continued

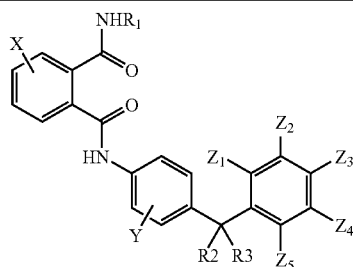

| | R1 | R2 | R3 | X | Y | Z1 | Z2 | Z3 | Z4 | Z5 | mp |
|---|---|---|---|---|---|---|---|---|---|---|---|
| 89 | CH(CH3)CH2SOCH3(S) | H | H | 3-Cl | 2-CH3 | H | H | C3F7-i | H | H | 85-91 |
| 90 | CH(CH3)CH2SO2CH3(S) | H | H | 3-Cl | 2-CH3 | H | H | C3F7-i | H | H | 101-104 |
| 91 | CH(CH3)CH2SC2H5(S) | H | H | 3-Cl | 2-CH3 | H | H | C3F7-i | H | H | |
| 92 | C(CH3)2CH2SCH3 | H | H | 3-Cl | 2-CH3 | H | H | C3F7-i | H | H | |
| 93 | CH(CH3)CH2SCH3(S) | H | H | 3-Cl | 2-CH3 | H | C4F9-n | H | H | H | |
| 94 | CH(CH3)CH2SOCH3(S) | H | H | 3-Cl | 2-CH3 | H | C4F9-n | H | H | H | |
| 95 | CH(CH3)CH2SO2CH3(S) | H | H | 3-Cl | 2-CH3 | H | C4F9-n | H | H | H | |
| 96 | CH(CH3)CH2SC2H5(S) | H | H | 3-Cl | 2-CH3 | H | C4F9-n | H | H | H | |
| 97 | C(CH3)2CH2SCH3 | H | H | 3-Cl | 2-CH3 | H | C4F9-n | H | H | H | |
| 98 | CH(CH3)CH2SCH3(S) | H | H | 3-Cl | 2-CH3 | H | H | C4F9-n | H | H | 81-85 |
| 99 | CH(CH3)CH2SOCH3(S) | H | H | 3-Cl | 2-CH3 | H | H | C4F9-n | H | H | |
| 100 | CH(CH3)CH2SO2CH3(S) | H | H | 3-Cl | 2-CH3 | H | H | C4F9-n | H | H | |
| 101 | CH(CH3)CH2SC2H5(S) | H | H | 3-Cl | 2-CH3 | H | H | C4F9-n | H | H | |
| 102 | C(CH3)2CH2SCH3 | H | H | 3-Cl | 2-CH3 | H | H | C4F9-n | H | H | |
| 103 | CH(CH3)CH2SCH3(S) | H | H | 3-Cl | 2-CH3 | H | C4F9-n | H | C4F9-n | H | 94-99 |
| 104 | CH(CH3)CH2SOCH3(S) | H | H | 3-Cl | 2-CH3 | H | C4F9-n | H | C4F9-n | H | |
| 105 | CH(CH3)CH2SO2CH3(S) | H | H | 3-Cl | 2-CH3 | H | C4F9-n | H | C4F9-n | H | |
| 106 | CH(CH3)CH2SC2H5(S) | H | H | 3-Cl | 2-CH3 | H | C4F9-n | H | C4F9-n | H | |
| 107 | CH(CH3)CH2SCH3(S) | H | H | 3-Cl | 2-CH3 | H | H | OCF3 | H | H | |
| 108 | CH(CH3)CH2SOCH3(S) | H | H | 3-Cl | 2-CH3 | H | H | OCF3 | H | H | |
| 109 | CH(CH3)CH2SO2CH3(S) | H | H | 3-Cl | 2-CH3 | H | H | OCF3 | H | H | |
| 110 | CH(CH3)CH2SC2H5(S) | H | H | 3-Cl | 2-CH3 | H | H | OCF3 | H | H | |
| 111 | C(CH3)2CH2SCH3 | H | H | 3-Cl | 2-CH3 | H | H | OCF3 | H | H | |
| 112 | CH(CH3)CH2SCH3(S) | H | H | 3-Cl | 2-CH3 | H | H | SCF3 | H | H | 73-81 |
| 113 | CH(CH3)CH2SOCH3(S) | H | H | 3-Cl | 2-CH3 | H | H | SCF3 | H | H | |
| 114 | CH(CH3)CH2SO2CH3(S) | H | H | 3-Cl | 2-CH3 | H | H | SCF3 | H | H | |
| 115 | CH(CH3)CH2SC2H5(S) | H | H | 3-Cl | 2-CH3 | H | H | SCF3 | H | H | |
| 116 | C(CH3)2CH2SCH3 | H | H | 3-Cl | 2-CH3 | H | H | SCF3 | H | H | |
| 117 | CH(CH3)CH2SCH3(S) | H | H | 3-Cl | 2-CH3 | H | SCF3 | H | SCF3 | H | |
| 118 | CH(CH3)CH2SOCH3(S) | H | H | 3-Cl | 2-CH3 | H | SCF3 | H | SCF3 | H | |
| 119 | CH(CH3)CH2SO2CH3(S) | H | H | 3-Cl | 2-CH3 | H | SCF3 | H | SCF3 | H | |
| 120 | CH(CH3)CH2SCH3(S) | H | H | 3-Cl | 2-CH3 | H | H | SOCF3 | H | H | |
| 121 | CH(CH3)CH2SOCH3(S) | H | H | 3-Cl | 2-CH3 | H | H | SOCF3 | H | H | |
| 122 | CH(CH3)CH2SO2CH3(S) | H | H | 3-Cl | 2-CH3 | H | H | SOCF3 | H | H | |
| 123 | CH(CH3)CH2SCH3(S) | H | H | 3-Cl | 2-CH3 | H | H | SO2CF3 | H | H | |
| 124 | CH(CH3)CH2SOCH3(S) | H | H | 3-Cl | 2-CH3 | H | H | SO2CF3 | H | H | |
| 125 | CH(CH3)CH2SO2CH3(S) | H | H | 3-Cl | 2-CH3 | H | H | SO2CF3 | H | H | |
| 126 | CH(CH3)CH2SCH3(S) | H | H | 3-Cl | 2-CH3 | H | H | SC2F5 | H | H | |
| 127 | CH(CH3)CH2SOCH3(S) | H | H | 3-Cl | 2-CH3 | H | H | SC2F5 | H | H | |
| 128 | CH(CH3)CH2SO2CH3(S) | H | H | 3-Cl | 2-CH3 | H | H | SC2F5 | H | H | |
| 129 | CH(CH3)CH2SC2H5(S) | H | H | 3-Cl | 2-CH3 | H | H | SC2F5 | H | H | |
| 130 | C(CH3)2CH2SCH3 | H | H | 3-Cl | 2-CH3 | H | H | SC2F5 | H | H | |
| 131 | CH(CH3)CH2SCH3(S) | H | H | 3-Cl | 2-CH3 | H | H | SOC2F5 | H | H | |
| 132 | CH(CH3)CH2SOCH3(S) | H | H | 3-Cl | 2-CH3 | H | H | SOC2F5 | H | H | |
| 133 | CH(CH3)CH2SO2CH3(S) | H | H | 3-Cl | 2-CH3 | H | H | SOC2F5 | H | H | |
| 134 | CH(CH3)CH2SCH3(S) | H | H | 3-Cl | 2-CH3 | H | OCF2Br | H | OCF2Br | H | |
| 135 | CH(CH3)CH2SOCH3(S) | H | H | 3-Cl | 2-CH3 | H | OCF2Br | H | OCF2Br | H | |
| 136 | CH(CH3)CH2SO2CH3(S) | H | H | 3-Cl | 2-CH3 | H | OCF2Br | H | OCF2Br | H | |
| 137 | CH(CH3)CH2SCH3(S) | H | H | 3-Cl | 2-CH3 | H | C2F5 | Cl | C2F5 | H | |
| 138 | CH(CH3)CH2SOCH3(S) | H | H | 3-Cl | 2-CH3 | H | C2F5 | Cl | C2F5 | H | |
| 139 | CH(CH3)CH2SO2CH3(S) | H | H | 3-Cl | 2-CH3 | H | C2F5 | Cl | C2F5 | H | |
| 140 | CH(CH3)CH2SC2H5(S) | H | H | 3-Cl | 2-CH3 | H | C2F5 | Cl | C2F5 | H | |
| 141 | C(CH3)2CH2SCH3 | H | H | 3-Cl | 2-CH3 | H | C2F5 | Cl | C2F5 | H | |
| 142 | CH(CH3)CH2SCH3(S) | H | H | 3-Cl | 2-CH3 | H | C2F5 | Br | C2F5 | H | |
| 143 | CH(CH3)CH2SCH3 | H | H | 3-Cl | 2-CH3 | H | Cl | C2F5 | Cl | H | |
| 144 | CH(CH3)CH2SCH3 | H | H | 3-Cl | 2-CH3 | H | Br | C2F5 | Br | H | |
| 145 | CH(CH3)CH2SCH3 | H | H | 3-Cl | 2-CH3 | H | Cl | C3F7-n | Cl | H | |
| 146 | CH(CH3)CH2SCH3 | H | H | 3-Cl | 2-CH3 | H | Br | C3F7-n | Br | H | |
| 147 | CH(CH3)CH2SCH3 | H | H | 3-Cl | 2-CH3 | H | C2F5 | Cl | H | H | |
| 148 | CH(CH3)CH2SCH3 | H | H | 3-Cl | 2-CH3 | H | C3F7-n | Cl | H | H | |
| 149 | CH(CH3)CH2SCH3(S) | H | H | 3-Cl | 2-CH3 | H | Cl | H | Cl | H | 176-181 |
| 150 | CH(CH3)CH2SOCH3(S) | H | H | 3-Cl | 2-CH3 | H | Cl | H | Cl | H | |
| 151 | CH(CH3)CH2SO2CH3(S) | H | H | 3-Cl | 2-CH3 | H | Cl | H | Cl | H | |
| 152 | CH(CH3)CH2SCH3(S) | H | H | 3-Cl | 2-CH3 | H | Br | H | Br | H | 90-94 |
| 153 | CH(CH3)CH2SOCH3(S) | H | H | 3-Cl | 2-CH3 | H | Br | H | Br | H | |

TABLE 1-continued

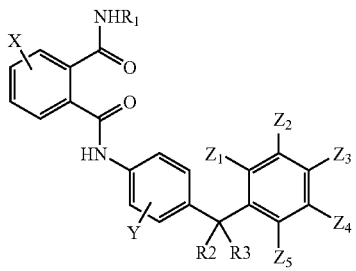

| | R1 | R2 | R3 | X | Y | Z1 | Z2 | Z3 | Z4 | Z5 | mp |
|---|---|---|---|---|---|---|---|---|---|---|---|
| 154 | CH(CH3)CH2SO2CH3(S) | H | H | 3-Cl | 2-CH3 | H | Br | H | Br | H | |
| 155 | CH(CH3)CH2SCH3(S) | H | H | 3-Cl | 2-CH3 | H | Cl | Cl | Cl | H | |
| 156 | CH(CH3)CH2SOCH3(S) | H | H | 3-Cl | 2-CH3 | H | Cl | Cl | Cl | H | |
| 157 | CH(CH3)CH2SO2CH3(S) | H | H | 3-Cl | 2-CH3 | H | Cl | Cl | Cl | H | |
| 158 | CH(CH3)CH2SCH3(S) | H | H | 3-Cl | 2-CH3 | H | Cl | Br | Cl | H | |
| 159 | CH(CH3)CH2SCH3(S) | H | H | 3-Cl | 2-CH3 | H | Br | Br | Br | H | |
| 160 | CH(CH3)CH2SOCH3(S) | H | H | 3-Cl | 2-CH3 | H | Br | Br | Br | H | |
| 161 | CH(CH3)CH2SO2CH3(S) | H | H | 3-Cl | 2-CH3 | H | Br | Br | Br | H | |
| 162 | CH(CH3)CH2SCH3(S) | H | H | 3-Cl | 2-CH3 | H | Br | Cl | Br | H | |
| 163 | CH(CH3)CH2SCH3(S) | H | H | 3-Br | 2-CH3 | H | CF3 | H | H | H | |
| 164 | CH(CH3)CH2SCH3(S) | H | H | 3-Br | 2-CH3 | H | H | CF3 | H | H | |
| 165 | CH(CH3)CH2SCH3(S) | H | H | 3-Br | 2-CH3 | H | CF3 | H | CF3 | H | |
| 166 | CH(CH3)CH2SOCH3(S) | H | H | 3-Br | 2-CH3 | H | CF3 | H | CF3 | H | |
| 167 | CH(CH3)CH2SO2CH3(S) | H | H | 3-Br | 2-CH3 | H | CF3 | H | CF3 | H | |
| 168 | C(CH3)2CH2SCH3 | H | H | 3-Br | 2-CH3 | H | CF3 | H | CF3 | H | |
| 169 | CH(CH3)CH2SCH3(S) | H | H | 3-Br | 2-CH3 | CF3 | H | CF3 | H | H | |
| 170 | CH(CH3)CH2SCH3(S) | H | H | 3-Br | 2-CH3 | H | C2F5 | H | H | H | |
| 171 | CH(CH3)CH2SCH3(S) | H | H | 3-Br | 2-CH3 | H | H | C2F5 | H | H | |
| 172 | iso-Pr | H | H | 3-Br | 2-CH3 | H | CF3 | H | CF3 | H | |
| 173 | CH(CH3)CH2SCH3(S) | H | H | 3-Br | 2-CH3 | H | CF3 | H | CF3 | H | |
| 174 | CH(CH3)CH2SC2H5(S) | H | H | 3-Br | 2-CH3 | H | CF3 | H | CF3 | H | |
| 175 | CH(CH3)CH2SOC2H5(S) | H | H | 3-Br | 2-CH3 | H | CF3 | H | CF3 | H | |
| 176 | CH(CH3)CH2SO2C2H5(S) | H | H | 3-Br | 2-CH3 | H | CF3 | H | CF3 | H | |
| 177 | C(CH3)2CH2SCH3 | H | H | 3-Br | 2-CH3 | H | CF3 | H | CF3 | H | |
| 178 | iso-Pr | H | H | 3-Br | 2-CH3 | H | C2F5 | H | C2F5 | H | |
| 179 | CH(CH3)CH2SCH3(S) | H | H | 3-Br | 2-CH3 | H | C2F5 | H | C2F5 | H | |
| 180 | CH(CH3)CH2SC2H5(S) | H | H | 3-Br | 2-CH3 | H | C2F5 | H | C2F5 | H | |
| 181 | CH(CH3)CH2SOC2H5(S) | H | H | 3-Br | 2-CH3 | H | C2F5 | H | C2F5 | H | |
| 182 | CH(CH3)CH2SO2C2H5(S) | H | H | 3-Br | 2-CH3 | H | C2F5 | H | C2F5 | H | |
| 183 | C(CH3)2CH2SCH3 | H | H | 3-Br | 2-CH3 | H | C2F5 | H | C2F5 | H | |
| 184 | CH(CH3)CH2SCH3(S) | H | H | 3-Br | 2-CH3 | H | C2F5 | C2F5 | H | H | |
| 185 | CH(CH3)CH2SOCH3(S) | H | H | 3-Br | 2-CH3 | H | C2F5 | C2F5 | H | H | |
| 186 | CH(CH3)CH2SO2CH3(S) | H | H | 3-Br | 2-CH3 | H | C2F5 | C2F5 | H | H | |
| 187 | CH(CH3)CH2SCH3 | H | H | 3-Br | 2-CH3 | H | C3F7-n | H | H | H | |
| 188 | CH(CH3)CH2SCH3 | H | H | 3-Br | 2-CH2 | H | H | C3F7-n | H | H | |
| 189 | CH(CH3)CH2SCH3 | H | H | 3-Br | 2-CH3 | H | C3F7-n | H | C3F7-n | H | |
| 190 | CH(CH3)CH2SCH3 | H | H | 3-Br | 2-CH3 | H | C3F7-i | H | H | H | |
| 191 | CH(CH3)CH2SCH3(S) | H | H | 3-Br | 2-CH3 | H | H | C3F7-i | H | H | |
| 192 | CH(CH3)CH2SOCH3(S) | H | H | 3-Br | 2-CH3 | H | H | C3F7-i | H | H | |
| 193 | CH(CH3)CH2SO2CH3(S) | H | H | 3-Br | 2-CH3 | H | H | C3F7-i | H | H | |
| 194 | CH(CH3)CH2SCH3 | H | H | 3-Br | 2-CH3 | H | C4F9-n | H | H | H | |
| 195 | CH(CH3)CH2SCH3 | H | H | 3-Br | 2-CH3 | H | H | C4F9-n | H | H | |
| 196 | CH(CH3)CH2SCH3 | H | H | 3-Br | 2-CH3 | H | C4F9-n | H | C4F9-n | H | |
| 197 | CH(CH3)CH2SCH3 | H | H | 3-Br | 2-CH3 | H | H | OCF3 | H | H | |
| 198 | CH(CH3)CH2SCH3 | H | H | 3-Br | 2-CH3 | H | H | SCF3 | H | H | |
| 199 | CH(CH3)CH2SCH3 | H | H | 3-Br | 2-CH3 | H | H | SC2F5 | H | H | |
| 200 | CH(CH3)CH2SC2H5(S) | H | H | 3-Br | 2-CH3 | H | C2F5 | Cl | C2F5 | H | |
| 201 | CH(CH3)CH2SCH3(S) | H | H | 3-Br | 2-CH3 | H | C2F5 | Br | C2F5 | H | |
| 202 | CH(CH3)CH2SCH3(S) | H | H | 3-Br | 2-CH3 | H | Cl | C2F5 | Cl | H | |
| 203 | CH(CH3)CH2SCH3(S) | H | H | 3-Br | 2-CH3 | H | Br | C2F5 | Br | H | |
| 204 | CH(CH3)CH2SCH3(S) | H | H | 3-Br | 2-CH3 | H | Cl | C3F7-n | Cl | H | |
| 205 | CH(CH3)CH2SCH3(S) | H | H | 3-Br | 2-CH3 | H | Br | C3F7-n | Br | H | |
| 206 | CH(CH3)CH2SCH3(S) | H | H | 3-Br | 2-CH3 | H | C2F5 | Cl | H | H | |
| 207 | CH(CH3)CH2SCH3(S) | H | H | 3-Br | 2-CH3 | H | C3F7-n | Cl | H | H | |
| 208 | CH(CH3)CH2SCH3(S) | H | H | 3-Br | 2-CH3 | H | Cl | H | Cl | H | |
| 209 | CH(CH3)CH2SCH3(S) | H | H | 3-Br | 2-CH3 | H | Br | H | Br | H | |
| 210 | CH(CH3)CH2SCH3(S) | H | H | 3-Br | 2-CH3 | H | Cl | Cl | Cl | H | |
| 211 | CH(CH3)CH2SCH3(S) | H | H | 3-Br | 2-CH3 | H | Br | Br | Br | H | 85-94 |
| 212 | CH(CH3)CH2SCH3(S) | H | H | 3-I | 2-CH3 | H | CF3 | H | CF3 | H | |
| 213 | CH(CH3)CH2SOCH3(S) | H | H | 3-I | 2-CH3 | H | CF3 | H | CF3 | H | |
| 214 | CH(CH3)CH2SO2CH3(S) | H | H | 3-I | 2-CH3 | H | CF3 | H | CF3 | H | |
| 215 | CH(CH3)CH2SC2H5(S) | H | H | 3-I | 2-CH3 | H | CF3 | H | CF3 | H | |
| 216 | C(CH3)2CH2SCH3 | H | H | 3-I | 2-CH3 | H | CF3 | H | CF3 | H | |
| 217 | CH(CH3)CH2SCH3(S) | H | H | 3-I | 2-CH3 | H | C2F5 | H | C2F5 | H | |
| 218 | CH(CH3)CH2SOCH3(S) | H | H | 3-I | 2-CH3 | H | C2F5 | H | C2F5 | H | |

TABLE 1-continued

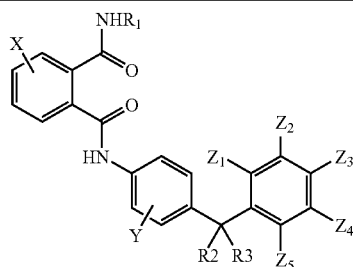

table 1

| | R1 | R2 | R3 | X | Y | Z1 | Z2 | Z3 | Z4 | Z5 | mp |
|---|---|---|---|---|---|---|---|---|---|---|---|
| 219 | CH(CH3)CH2SO2CH3(S) | H | H | 3-I | 2-CH3 | H | C2F5 | H | C2F5 | H | |
| 220 | CH(CH3)CH2SC2H5(S) | H | H | 3-I | 2-CH3 | H | C2F5 | H | C2F5 | H | |
| 221 | C(CH3)2CH2SCH3 | H | H | 3-I | 2-CH3 | H | C2F5 | H | C2F5 | H | |
| 222 | CH(CH3)CH2SCH3(S) | H | H | 3-I | 2-CH3 | H | C2F5 | C2F5 | H | H | |
| 223 | CH(CH3)CH2SCH3(S) | H | H | 3-I | 2-CH3 | H | C3F7-n | H | H | H | |
| 224 | CH(CH3)CH2SCH3(S) | H | H | 3-I | 2-CH3 | H | H | C3F7-n | H | H | |
| 225 | CH(CH3)CH2SCH3(S) | H | H | 3-I | 2-CH3 | H | C3F7-n | H | C3F7-n | H | |
| 226 | CH(CH3)CH2SCH3(S) | H | H | 3-I | 2-CH3 | H | C3F7-i | H | H | H | |
| 227 | CH(CH3)CH2SCH3(S) | H | H | 3-I | 2-CH3 | H | H | C3F7-i | H | H | |
| 228 | CH(CH3)CH2SCH3(S) | H | H | 3-I | 2-CH3 | H | C4F9-n | H | H | H | |
| 229 | CH(CH3)CH2SCH3(S) | H | H | 3-I | 2-CH3 | H | H | C4F9-n | H | H | |
| 230 | CH(CH3)CH2SCH3(S) | H | H | 3-I | 2-CH3 | H | C4F9-n | H | C4F9-n | H | |
| 231 | CH(CH3)CH2SCH3(S) | H | H | 3-I | 2-CH3 | H | H | OCF3 | H | H | |
| 232 | CH(CH3)CH2SCH3(S) | H | H | 3-I | 2-CH3 | H | H | SCF3 | H | H | |
| 233 | CH(CH3)CH2SCH3(S) | H | H | 3-I | 2-CH3 | H | H | SC2F5 | H | H | |
| 234 | CH(CH3)CH2SCH3 | H | H | 3-I | 2-CH3 | H | C2F5 | Cl | C2F5 | H | |
| 235 | CH(CH3)CH2SCH3 | H | H | 3-I | 2-CH3 | H | C2F5 | Br | C2F5 | H | |
| 236 | CH(CH3)CH2SCH3 | H | H | 3-I | 2-CH3 | H | Cl | C2F5 | Cl | H | |
| 237 | CH(CH3)CH2SCH3 | H | H | 3-I | 2-CH3 | H | Br | C2F5 | Br | H | |
| 238 | CH(CH3)CH2SCH3 | H | H | 3-I | 2-CH3 | H | Cl | C3F7-n | Cl | H | |
| 239 | CH(CH3)CH2SCH3 | H | H | 3-I | 2-CH3 | H | Br | C3F7-n | Br | H | |
| 240 | CH(CH3)CH2SCH3 | H | H | 3-I | 2-CH3 | H | C2F5 | Cl | H | H | |
| 241 | CH(CH3)CH2SCH3 | H | H | 3-I | 2-CH3 | H | C3F7-n | Cl | H | H | |
| 242 | CH(CH3)CH2SCH3(S) | H | H | 3-I | 2-CH3 | H | Cl | H | Cl | H | |
| 243 | CH(CH3)CH2SCH3(S) | H | H | 3-I | 2-CH3 | H | Br | H | Br | H | |
| 244 | CH(CH3)CH2SCH3(S) | H | H | 3-I | 2-CH3 | H | Cl | Cl | Cl | H | |
| 245 | CH(CH3)CH2SCH3(S) | H | H | 3-I | 2-CH3 | H | Br | Br | Br | H | |
| 246 | CH(CH3)CH2SCH3(S) | H | H | 3-F | 2-CH3 | H | CF3 | H | CF3 | H | |
| 247 | CH(CH3)CH2SCH3(S) | H | H | 3-F | 2-CH3 | H | C2F5 | H | C2F5 | H | |
| 248 | CH(CH3)CH2SOCH3(S) | H | H | 3-F | 2-CH3 | H | CF3 | H | CF3 | H | |
| 249 | CH(CH3)CH2SOCH3(S) | H | H | 3-F | 2-CH3 | H | C2F5 | H | C2F5 | H | |
| 250 | CH(CH3)CH2SO2CH3(S) | H | H | 3-F | 2-CH3 | H | CF3 | H | CF3 | H | |
| 251 | CH(CH3)CH2SO2CH3(S) | H | H | 3-F | 2-CH3 | H | C2F5 | H | C2F5 | H | |
| 252 | CH(CH3)CH2SCH3 | H | H | 3-NO2 | 2-CH3 | H | CF3 | H | CF3 | H | |
| 253 | CH(CH3)CH2SCH3 | H | H | 3-NO2 | 2-CH3 | H | C2F5 | H | C2F5 | H | |
| 254 | CH(CH3)CH2SCH3 | H | H | 3-MeSO2O | 2-CH3 | H | CF3 | H | CF3 | H | |
| 255 | CH(CH3)CH2SCH3 | H | H | 3-MeSO2O | 2-CH3 | H | C2F5 | H | C2F5 | H | |
| 256 | CH(CH3)CH2SCH3 | H | H | 3-MeS | 2-CH3 | H | CF3 | H | CF3 | H | |
| 257 | CH(CH3)CH2SCH3 | H | H | 3-MeS | 2-CH3 | H | C2F5 | H | C2F5 | H | |
| 258 | CH(CH3)CH2SCH3 | H | H | 3-MeSO | 2-CH3 | H | CF3 | H | CF3 | H | |
| 259 | CH(CH3)CH2SCH3 | H | H | 3-MeSO | 2-CH3 | H | C2F5 | H | C2F5 | H | |
| 260 | CH(CH3)CH2SCH3 | H | H | 3-MeSO2 | 2-CH3 | H | CF3 | H | CF3 | H | |
| 261 | CH(CH3)CH2SCH3 | H | H | 3-MeSO2 | 2-CH3 | H | C2F5 | H | C2F5 | H | |
| 262 | C(CH3)2CH2SCH3(S) | CH3 | H | 3-Cl | 2-CH3 | H | CF3 | H | CF3 | H | |
| 263 | C(CH3)2CH2SOCH3(S) | CH3 | H | 3-Cl | 2-CH3 | H | CF3 | H | CF3 | H | |
| 264 | C(CH3)2CH2SO2CH3(S) | CH3 | H | 3-Cl | 2-CH3 | H | CF3 | H | CF3 | H | |
| 265 | C(CH3)2CH2SCH3 | CH3 | H | 3-Cl | 2-CH3 | H | CF3 | H | CF3 | H | |
| 266 | CH(CH3)CH2SCH3(S) | CH3 | H | 3-Cl | 2-CH3 | H | CF3 | CF3 | H | H | |
| 267 | CH(CH3)CH2SCH3(S) | CH3 | H | 3-Cl | 2-CH3 | H | C2F5 | H | H | H | |
| 268 | CH(CH3)CH2SCH3(S) | CH3 | H | 3-Cl | 2-CH3 | H | H | C2F5 | H | H | |
| 269 | iso-Pr | CH3 | H | 3-Cl | 2-CH3 | H | C2F5 | H | C2F5 | H | |
| 270 | CH(CH3)CH2SCH3(S) | CH3 | H | 3-Cl | 2-CH3 | H | C2F5 | H | C2F5 | H | |
| 271 | CH(CH3)CH2SOCH3(S) | CH3 | H | 3-Cl | 2-CH3 | H | C2F5 | H | C2F5 | H | |
| 272 | CH(CH3)CH2SO2CH3(S) | CH3 | H | 3-Cl | 2-CH3 | H | C2F5 | H | C2F5 | H | |
| 273 | CH(CH3)CH2SC2H5(S) | CH3 | H | 3-Cl | 2-CH3 | H | C2F5 | H | C2F5 | H | |
| 274 | C(CH3)2CH2SCH3 | CH3 | H | 3-Cl | 2-CH3 | H | C2F5 | H | C2F5 | H | |
| 275 | CH(CH3)CH2SCH3(S) | CH3 | H | 3-Cl | 2-CH3 | H | C2F5 | C2F5 | H | H | |
| 276 | CH(CH3)CH2SCH3(S) | CH3 | H | 3-Cl | 2-CH3 | H | C3F7-n | H | H | H | |
| 277 | CH(CH3)CH2SCH3(S) | CH3 | H | 3-Cl | 2-CH3 | H | H | C3F7-n | H | H | |
| 278 | CH(CH3)CH2SCH3(S) | CH3 | H | 3-Cl | 2-CH3 | H | C3F7-n | H | C3F7-n | H | |
| 279 | CH(CH3)CH2SCH3(S) | CH3 | H | 3-Cl | 2-CH3 | H | C3F7-i | H | H | H | |
| 280 | CH(CH3)CH2SCH3(S) | CH3 | H | 3-Cl | 2-CH3 | H | H | C3F7-i | H | H | |
| 281 | CH(CH3)CH2SCH3(S) | CH3 | H | 3-Cl | 2-CH3 | H | H | C4F9-n | H | H | |
| 282 | CH(CH3)CH2SCH3(S) | CH3 | H | 3-Cl | 2-CH3 | H | C4F9-n | H | C4F9-n | H | |
| 283 | CH(CH3)CH2SCH3(S) | CH3 | H | 3-Cl | 2-CH3 | H | H | OCF3 | H | H | |

TABLE 1-continued

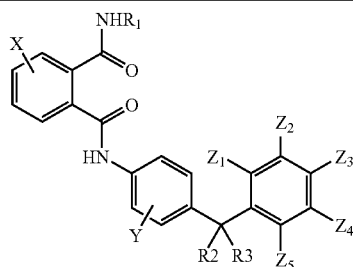

| | R1 | R2 | R3 | X | Y | Z1 | Z2 | Z3 | Z4 | Z5 | mp |
|---|---|---|---|---|---|---|---|---|---|---|---|
| 284 | CH(CH3)CH2SCH3(S) | CH3 | H | 3-Cl | 2-CH3 | H | H | SCF3 | H | H | |
| 285 | CH(CH3)CH2SCH3(S) | CH3 | H | 3-Cl | 2-CH3 | H | H | SC2F5 | H | H | |
| 286 | CH(CH3)CH2SCH3(S) | CH3 | H | 3-Cl | 2-CH3 | H | C2F5 | Cl | C2F5 | H | |
| 287 | CH(CH3)CH2SCH3(S) | CH3 | H | 3-Cl | 2-CH3 | H | C2F5 | Br | C2F5 | H | |
| 288 | CH(CH3)CH2SCH3(S) | CH3 | H | 3-Cl | 2-CH3 | H | Cl | C2F5 | Cl | H | |
| 289 | CH(CH3)CH2SCH3(S) | CH3 | H | 3-Cl | 2-CH3 | H | Br | C2F5 | Br | H | |
| 290 | CH(CH3)CH2SCH3(S) | CH3 | H | 3-Cl | 2-CH3 | H | Cl | C3F7-n | Cl | H | |
| 291 | CH(CH3)CH2SCH3(S) | CH3 | H | 3-Cl | 2-CH3 | H | Br | C3F7-n | Br | H | |
| 292 | CH(CH3)CH2SCH3(S) | CH3 | H | 3-Cl | 2-CH3 | H | C2F5 | Cl | H | H | |
| 293 | CH(CH3)CH2SCH3(S) | CH3 | H | 3-Cl | 2-CH3 | H | C3F7-n | Cl | H | H | |
| 294 | CH(CH3)CH2SCH3(S) | CH3 | H | 3-Cl | 2-CH3 | H | Cl | H | Cl | H | |
| 295 | CH(CH3)CH2SCH3(S) | CH3 | H | 3-Cl | 2-CH3 | H | Br | H | Br | H | |
| 296 | CH(CH3)CH2SCH3(S) | CH3 | H | 3-Cl | 2-CH3 | H | Cl | Cl | Cl | H | |
| 297 | CH(CH3)CH2SCH3(S) | CH3 | H | 3-Cl | 2-CH3 | H | Br | Br | Br | H | |
| 298 | C(CH3)2CH2SCH3 | CH3 | H | 3-Br | 2-CH3 | H | C2F5 | H | H | H | |
| 299 | CH(CH3)CH2SCH3(S) | CH3 | H | 3-Br | 2-CH3 | H | H | CF3 | H | H | |
| 300 | CH(CH3)CH2SCH3(S) | CH3 | H | 3-Br | 2-CH3 | H | CF3 | H | CF3 | H | |
| 301 | CH(CH3)CH2SCH3(S) | CH3 | H | 3-Br | 2-CH3 | H | C2F5 | H | C2F5 | H | |
| 302 | CH(CH3)CH2SCH3(S) | CH3 | H | 3-Br | 2-CH3 | H | C2F5 | C2F5 | H | H | |
| 303 | CH(CH3)CH2SCH3(S) | CH3 | H | 3-Br | 2-CH3 | H | H | C3F7-n | H | H | |
| 304 | CH(CH3)CH2SCH3(S) | CH3 | H | 3-Br | 2-CH3 | H | C3F7-n | H | C3F7-n | H | |
| 305 | CH(CH3)CH2SCH3(S) | CH3 | H | 3-Br | 2-CH3 | H | H | C3F7-i | H | H | |
| 306 | CH(CH3)CH2SCH3(S) | CH3 | H | 3-Br | 2-CH3 | H | H | C4F9-n | H | H | |
| 307 | CH(CH3)CH2SCH3(S) | CH3 | H | 3-Br | 2-CH3 | H | H | OCF3 | H | H | |
| 308 | CH(CH3)CH2SCH3(S) | CH3 | H | 3-Br | 2-CH3 | H | H | SCF3 | H | H | |
| 309 | CH(CH3)CH2SCH3(S) | CH3 | H | 3-Br | 2-CH3 | H | C2F5 | Cl | C2F5 | H | |
| 310 | CH(CH3)CH2SCH3(S) | CH3 | H | 3-Br | 2-CH3 | H | C2F5 | Br | C2F5 | H | |
| 311 | CH(CH3)CH2SCH3 | CH3 | H | 3-Br | 2-CH3 | H | Cl | C2F5 | Cl | H | |
| 312 | CH(CH3)CH2SCH3 | CH3 | H | 3-Br | 2-CH3 | H | Br | C2F5 | Br | H | |
| 313 | CH(CH3)CH2SCH3 | CH3 | H | 3-Br | 2-CH3 | H | Cl | C3F7-n | Cl | H | |
| 314 | CH(CH3)CH2SCH3 | CH3 | H | 3-Br | 2-CH3 | H | Br | C3F7-n | Br | H | |
| 315 | CH(CH3)CH2SCH3 | CH3 | H | 3-Br | 2-CH3 | H | C2F5 | Cl | H | H | |
| 316 | CH(CH3)CH2SCH3 | CH3 | H | 3-Br | 2-CH3 | H | C3F7-n | Cl | H | H | |
| 317 | CH(CH3)CH2SCH3 | CH3 | H | 3-Br | 2-CH3 | H | Cl | H | Cl | H | |
| 318 | CH(CH3)CH2SCH3 | CH3 | H | 3-Br | 2-CH2 | H | Br | H | Br | H | |
| 319 | CH(CH3)CH2SCH3 | CH3 | H | 3-Br | 2-CH3 | H | Cl | Cl | Cl | H | |
| 320 | CH(CH3)CH2SCH3 | CH3 | H | 3-Br | 2-CH3 | H | Br | Br | Br | H | |
| 321 | CH(CH3)CH2SOCH3(S) | CH3 | H | 3-I | 2-CH3 | H | CF3 | H | CF3 | H | |
| 322 | CH(CH3)CH2SOCH3(S) | CH3 | H | 3-I | 2-CH3 | H | C2F5 | H | C2F5 | H | |
| 323 | CH(CH3)CH2SCH3 | CH3 | H | 3-I | 2-CH3 | H | C2F5 | C2F5 | H | H | |
| 324 | CH(CH3)CH2SCH3(S) | CH3 | H | 3-I | 2-CH3 | H | H | C3F7-n | H | H | |
| 325 | CH(CH3)CH2SCH3(S) | CH3 | H | 3-I | 2-CH3 | H | C3F7-n | H | C3F7-n | H | |
| 326 | CH(CH3)CH2SCH3(S) | CH3 | H | 3-I | 2-CH3 | H | H | C3F7-i | H | H | |
| 327 | CH(CH3)CH2SCH3(S) | CH3 | H | 3-I | 2-CH3 | H | H | C4F9-n | H | H | |
| 328 | CH(CH3)CH2SCH3(S) | CH3 | H | 3-I | 2-CH3 | H | H | OCF3 | H | H | |
| 329 | CH(CH3)CH2SCH3(S) | CH3 | H | 3-I | 2-CH3 | H | H | SCF3 | H | H | |
| 330 | CH(CH3)CH2SCH3(S) | CH3 | H | 3-I | 2-CH3 | H | C2F5 | Cl | C2F5 | H | |
| 331 | CH(CH3)CH2SCH3(S) | CH3 | H | 3-I | 2-CH3 | H | C2F5 | Br | C2F5 | H | |
| 332 | CH(CH3)CH2SCH3(S) | CH3 | H | 3-I | 2-CH3 | H | Cl | C2F5 | Cl | H | |
| 333 | CH(CH3)CH2SCH3(S) | CH3 | H | 3-I | 2-CH3 | H | Br | C2F5 | Br | H | |
| 334 | CH(CH3)CH2SCH3(S) | CH3 | H | 3-I | 2-CH3 | H | Cl | C3F7-n | Cl | H | |
| 335 | CH(CH3)CH2SCH3(S) | CH3 | H | 3-I | 2-CH3 | H | Br | C3F7-n | Br | H | |
| 336 | CH(CH3)CH2SCH3(S) | CH3 | H | 3-I | 2-CH3 | H | C2F5 | Cl | H | H | |
| 337 | CH(CH3)CH2SCH3(S) | CH3 | H | 3-I | 2-CH3 | H | C3F7-n | Cl | H | H | |
| 338 | CH(CH3)CH2SCH3(S) | CH3 | H | 3-I | 2-CH3 | H | Cl | H | Cl | H | |
| 339 | CH(CH3)CH2SCH3(S) | CH3 | H | 3-I | 2-CH3 | H | Br | H | Br | H | |
| 340 | CH(CH3)CH2SCH3(S) | CH3 | H | 3-I | 2-CH3 | H | Cl | Cl | Cl | H | |
| 341 | CH(CH3)CH2SCH3(S) | CH3 | H | 3-I | 2-CH3 | H | Br | Br | Br | H | |
| 342 | CH(CH3)CH2SCH3(S) | CH3 | H | 3-F | 2-CH3 | H | C2F5 | H | C2F5 | H | |
| 343 | CH(CH3)CH2SCH3(S) | CH3 | H | 3-NO2 | 2-CH3 | H | C2F5 | H | C2F5 | H | |
| 344 | CH(CH3)CH2SCH3(S) | CF3 | H | 3-Cl | 2-CH3 | H | H | CF3 | H | H | |
| 345 | CH(CH3)CH2SCH3(S) | CF3 | H | 3-Cl | 2-CH3 | H | CF3 | H | CF3 | H | 85-88 |
| 346 | CH(CH3)CH2SOCH3(S) | CF3 | H | 3-Cl | 2-CH3 | H | CF3 | H | CF3 | H | |
| 347 | CH(CH3)CH2SO2CH3(S) | CF3 | H | 3-Cl | 2-CH3 | H | CF3 | H | CF3 | H | |
| 348 | CH(CH3)CH2SCH3(S) | CF3 | H | 3-Cl | 2-CH3 | H | CF3 | CF3 | H | H | |

TABLE 1-continued

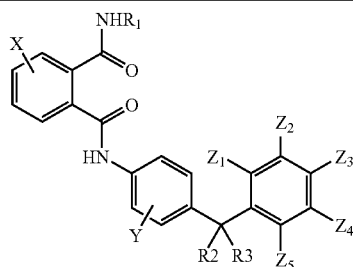

| | R1 | R2 | R3 | X | Y | Z1 | Z2 | Z3 | Z4 | Z5 | mp |
|---|---|---|---|---|---|---|---|---|---|---|---|
| 349 | CH(CH3)CH2SCH3(S) | CF3 | H | 3-Cl | 2-CH3 | H | H | C2F5 | H | H | |
| 350 | CH(CH3)CH2SCH3 | CF3 | H | 3-Cl | 2-CH3 | H | C2F5 | H | C2F5 | H | |
| 351 | CH(CH3)CH2SCH3(S) | CF3 | H | 3-Cl | 2-CH3 | H | C2F5 | H | C2F5 | H | |
| 352 | CH(CH3)CH2SOCH3(S) | CF3 | H | 3-Cl | 2-CH3 | H | C2F5 | H | C2F5 | H | |
| 353 | CH(CH3)CH2SCH3(S) | CF3 | H | 3-Cl | 2-CH3 | H | C2F5 | C2F5 | H | H | |
| 354 | CH(CH3)CH2SCH3(S) | CF3 | H | 3-Cl | 2-CH3 | H | H | C3F7-n | H | H | |
| 355 | CH(CH3)CH2SCH3(S) | CF3 | H | 3-Cl | 2-CH3 | H | C3F7-n | H | C3F7-n | H | |
| 356 | CH(CH3)CH2SCH3(S) | CF3 | H | 3-Cl | 2-CH3 | H | H | C3F7-i | H | H | |
| 357 | CH(CH3)CH2SCH3(S) | CF3 | H | 3-Cl | 2-CH3 | H | H | C4F9-n | H | H | |
| 358 | CH(CH3)CH2SCH3(S) | CF3 | H | 3-Cl | 2-CH3 | H | H | OCF3 | H | H | |
| 359 | CH(CH3)CH2SCH3(S) | CF3 | H | 3-Cl | 2-CH3 | H | H | SCF3 | H | H | |
| 360 | CH(CH3)CH2SCH3(S) | CF3 | H | 3-Cl | 2-CH3 | H | C2F5 | Cl | C2F5 | H | |
| 361 | CH(CH3)CH2SCH3(S) | CF3 | H | 3-Cl | 2-CH3 | H | C2F5 | Br | C2F5 | H | |
| 362 | CH(CH3)CH2SCH3(S) | CF3 | H | 3-Cl | 2-CH3 | H | Cl | C2F5 | Cl | H | |
| 363 | CH(CH3)CH2SCH3(S) | CF3 | H | 3-Cl | 2-CH3 | H | Br | C2F5 | Br | H | |
| 364 | C(CH3)2CH2SCH3 | CF3 | H | 3-Cl | 2-CH3 | H | Br | C2F5 | Br | H | |
| 365 | CH(CH3)CH2SCH3(S) | CF3 | H | 3-Cl | 2-CH3 | H | Cl | C3F7-n | Cl | H | |
| 366 | CH(CH3)CH2SCH3(S) | CF3 | H | 3-Cl | 2-CH3 | H | Br | C3F7-n | Br | H | |
| 367 | CH(CH3)CH2SCH3(S) | CF3 | H | 3-Cl | 2-CH3 | H | C2F5 | Cl | H | H | |
| 368 | CH(CH3)CH2SCH3(S) | CF3 | H | 3-Cl | 2-CH3 | H | C3F7-n | Cl | H | H | |
| 369 | CH(CH3)CH2SCH3(S) | CF3 | H | 3-Cl | 2-CH3 | H | Cl | H | Cl | H | |
| 370 | CH(CH3)CH2SCH3(S) | CF3 | H | 3-Cl | 2-CH3 | H | Br | H | Br | H | |
| 371 | CH(CH3)CH2SCH3(S) | CF3 | H | 3-Cl | 2-CH3 | H | Cl | Cl | Cl | H | |
| 372 | CH(CH3)CH2SCH3(S) | CF3 | H | 3-Cl | 2-CH3 | H | Br | Br | Br | H | |
| 373 | CH(CH3)CH2SO2CH3(S) | CF3 | H | 3-Br | 2-CH3 | H | CF3 | H | CF3 | H | |
| 374 | CH(CH3)CH2SO2CH3(S) | CF3 | H | 3-Br | 2-CH3 | H | C2F5 | H | C2F5 | H | |
| 375 | CH(CH3)CH2SCH3(S) | CF3 | H | 3-Br | 2-CH3 | H | C2F5 | C2F5 | H | H | |
| 376 | CH(CH3)CH2SCH3(S) | CF3 | H | 3-Br | 2-CH3 | H | H | C3F7-n | H | H | |
| 377 | CH(CH3)CH2SCH3(S) | CF3 | H | 3-Br | 2-CH3 | H | C3F7-n | H | C3F7-n | H | |
| 378 | CH(CH3)CH2SCH3(S) | CF3 | H | 3-Br | 2-CH3 | H | H | C3F7-i | H | H | |
| 379 | CH(CH3)CH2SCH3(S) | CF3 | H | 3-Br | 2-CH3 | H | H | C4F9-n | H | H | |
| 380 | CH(CH3)CH2SCH3 | CF3 | H | 3-Br | 2-CH3 | H | H | OCF3 | H | H | |
| 381 | CH(CH3)CH2SCH3 | CF3 | H | 3-Br | 2-CH3 | H | H | SCF3 | H | H | |
| 382 | CH(CH3)CH2SCH3 | CF3 | H | 3-Br | 2-CH3 | H | C2F5 | Cl | C2F5 | H | |
| 383 | CH(CH3)CH2SCH3 | CF3 | H | 3-Br | 2-CH3 | H | C2F5 | Br | C2F5 | H | |
| 384 | CH(CH3)CH2SCH3 | CF3 | H | 3-Br | 2-CH3 | H | Cl | C2F5 | Cl | H | |
| 385 | CH(CH3)CH2SCH3 | CF3 | H | 3-Br | 2-CH3 | H | Br | C2F5 | Br | H | |
| 386 | CH(CH3)CH2SCH3 | CF3 | H | 3-Br | 2-CH3 | H | Cl | C3F7-n | Cl | H | |
| 387 | CH(CH3)CH2SCH3 | CF3 | H | 3-Br | 2-CH3 | H | Br | C3F7-n | Br | H | |
| 388 | CH(CH3)CH2SCH3 | CF3 | H | 3-Br | 2-CH3 | H | C2F5 | Cl | H | H | |
| 389 | CH(CH3)CH2SCH3 | CF3 | H | 3-Br | 2-CH3 | H | C3F7-n | Cl | H | H | |
| 390 | CH(CH3)CH2SCH3 | CF3 | H | 3-Br | 2-CH3 | H | Cl | H | Cl | H | |
| 391 | CH(CH3)CH2SCH3 | CF3 | H | 3-Br | 2-CH3 | H | Br | H | Br | H | |
| 392 | CH(CH3)CH2SCH3 | CF3 | H | 3-Br | 2-CH3 | H | Cl | Cl | Cl | H | |
| 393 | CH(CH3)CH2SCH3 | CF3 | H | 3-Br | 2-CH3 | H | Br | Br | Br | H | |
| 394 | CH(CH3)CH2SCH3(S) | CF3 | H | 3-I | 2-CH3 | H | H | CF3 | H | H | |
| 395 | CH(CH3)CH2SCH3(S) | CF3 | H | 3-I | 2-CH3 | H | CF3 | H | CF3 | H | |
| 396 | CH(CH3)CH2SCH3(S) | CF3 | H | 3-I | 2-CH3 | H | H | C2F5 | H | H | |
| 397 | CH(CH3)CH2SCH3 | CF3 | H | 3-I | 2-CH3 | H | C2F5 | H | C2F5 | H | |
| 398 | CH(CH3)CH2SCH3(S) | CF3 | H | 3-I | 2-CH3 | H | C2F5 | C2F5 | H | H | |
| 399 | CH(CH3)CH2SCH3(S) | CF3 | H | 3-I | 2-CH3 | H | H | C3F7-n | H | H | |
| 400 | CH(CH3)CH2SCH3(S) | CF3 | H | 3-I | 2-CH3 | H | C3F7-n | H | C3F7-n | H | |
| 401 | CH(CH3)CH2SCH3(S) | CF3 | H | 3-I | 2-CH3 | H | H | C3F7-i | H | H | |
| 402 | CH(CH3)CH2SCH3(S) | CF3 | H | 3-I | 2-CH3 | H | H | C4F9-n | H | H | |
| 403 | CH(CH3)CH2SCH3(S) | CF3 | H | 3-I | 2-CH3 | H | H | OCF3 | H | H | |
| 404 | CH(CH3)CH2SCH3(S) | CF3 | H | 3-I | 2-CH3 | H | H | SCF3 | H | H | |
| 405 | CH(CH3)CH2SCH3(S) | CF3 | H | 3-I | 2-CH3 | H | C2F5 | Cl | C2F5 | H | |
| 406 | CH(CH3)CH2SCH3(S) | CF3 | H | 3-I | 2-CH3 | H | C2F5 | Br | C2F5 | H | |
| 407 | CH(CH3)CH2SCH3(S) | CF3 | H | 3-I | 2-CH3 | H | Cl | C2F5 | Cl | H | |
| 408 | CH(CH3)CH2SCH3(S) | CF3 | H | 3-I | 2-CH3 | H | Br | C2F5 | Br | H | |
| 409 | CH(CH3)CH2SCH3(S) | CF3 | H | 3-I | 2-CH3 | H | Cl | C3F7-n | Cl | H | |
| 410 | CH(CH3)CH2SCH3(S) | CF3 | H | 3-I | 2-CH3 | H | Br | C3F7-n | Br | H | |
| 411 | CH(CH3)CH2SCH3(S) | CF3 | H | 3-I | 2-CH3 | H | Cl | H | Cl | H | |
| 412 | CH(CH3)CH2SCH3(S) | CF3 | H | 3-I | 2-CH3 | H | Br | H | Br | H | |
| 413 | CH(CH3)CH2SCH3(S) | CF3 | H | 3-I | 2-CH3 | H | Cl | Cl | Cl | H | |

TABLE 1-continued

| | R1 | R2 | R3 | X | Y | Z1 | Z2 | Z3 | Z4 | Z5 | mp |
|---|---|---|---|---|---|---|---|---|---|---|---|
| 414 | CH(CH3)CH2SCH3(S) | CF3 | H | 3-I | 2-CH3 | H | Br | Br | Br | H | |
| 415 | CH(CH3)CH2SCH3(S) | CF3 | H | 3-F | 2-CH3 | H | CF3 | H | CF3 | H | |
| 416 | CH(CH3)CH2SCH3(S) | CF3 | H | 3-F | 2-CH3 | H | C2F5 | H | C2F5 | H | |
| 417 | CH(CH3)CH2SCH3(S) | CF3 | H | 3-MeSO2 | 2-CH3 | H | CF3 | H | CF3 | H | |
| 418 | CH(CH3)CH2SCH3(S) | CF3 | H | 3-MeSO2 | 2-CH3 | H | C2F5 | H | C2F5 | H | |
| 419 | CH(CH3)CH2SCH3(S) | H | OH | 3-Cl | 2-CH3 | H | CF3 | H | CF3 | H | |
| 420 | CH(CH3)CH2SCH3(S) | H | OH | 3-Cl | 2-CH3 | H | C2F5 | H | C2F5 | H | |
| 421 | CH(CH3)CH2SCH3(S) | H | OH | 3-Cl | 2-CH3 | H | Cl | H | Cl | H | |
| 422 | CH(CH3)CH2SCH3(S) | H | OH | 3-Cl | 2-CH3 | H | Br | H | Br | H | |
| 423 | CH(CH3)CH2SCH3(S) | CF3 | OH | 3-Cl | 2-CH3 | H | CF3 | H | CF3 | H | |
| 424 | CH(CH3)CH2SCH3(S) | CF3 | OH | 3-Cl | 2-CH3 | H | C2F5 | H | C2F5 | H | |
| 425 | CH(CH3)CH2SCH3(S) | CF3 | OH | 3-Cl | 2-CH3 | H | C2F5 | C2F5 | H | H | |
| 426 | CH(CH3)CH2SCH3(S) | CF3 | OH | 3-I | 2-CH3 | H | CF3 | H | CF3 | H | |
| 427 | CH(CH3)CH2SCH3(S) | CF3 | OH | 3-I | 2-CH3 | H | C2F5 | H | C2F5 | H | |
| 428 | CH(CH3)CH2SCH3(S) | CF3 | OH | 3-F | 2-CH3 | H | CF3 | H | CF3 | H | |
| 429 | CH(CH3)CH2SCH3(S) | CF3 | OH | 3-F | 2-CH3 | H | C2F5 | H | C2F5 | H | |
| 430 | CH(CH3)CH2SCH3(S) | CF3 | OH | 3-NO2 | 2-CH3 | H | CF3 | H | CF3 | H | |
| 431 | CH(CH3)CH2SCH3(S) | CF3 | OH | 3-NO2 | 2-CH3 | H | C2F5 | H | C2F5 | H | |
| 432 | CH(CH3)CH2SCH3(S) | CF3 | OH | 3-MeSO2O | 2-CH3 | H | CF3 | H | CF3 | H | |
| 433 | CH(CH3)CH2SCH3(S) | CF3 | OH | 3-MeSO2O | 2-CH3 | H | C2F5 | H | C2F5 | H | |
| 434 | CH(CH3)CH2SCH3(S) | CF3 | OH | 3-MeS | 2-CH3 | H | CF3 | H | CF3 | H | |
| 435 | CH(CH3)CH2SCH3(S) | CF3 | OH | 3-MeS | 2-CH3 | H | C2F5 | H | C2F5 | H | |
| 436 | CH(CH3)CH2SCH3(S) | CF3 | OH | 3-MeSO | 2-CH3 | H | CF3 | H | CF3 | H | |
| 437 | CH(CH3)CH2SCH3(S) | CF3 | OH | 3-MeSO | 2-CH3 | H | C2F5 | H | C2F5 | H | |
| 438 | CH(CH3)CH2SCH3(S) | CF3 | OH | 3-MeSO2 | 2-CH3 | H | CF3 | H | CF3 | H | |
| 439 | CH(CH3)CH2SCH3(S) | CF3 | OH | 3-MeSO2 | 2-CH3 | H | C2F5 | H | C2F5 | H | |
| 440 | CH(CH3)CH2SCH3(S) | H | H | 3-Cl | 2-Cl | H | CF3 | H | CF3 | H | |
| 441 | CH(CH3)CH2SCH3(S) | H | H | 3-Cl | 2-Cl | H | C2F5 | H | C2F5 | H | |
| 442 | CH(CH3)CH2SCH3(S) | H | H | 3-Br | 2-Cl | H | CF3 | H | CF3 | H | |
| 443 | CH(CH3)CH2SCH3(S) | H | H | 3-Br | 2-Cl | H | C2F5 | H | C2F5 | H | |
| 444 | CH(CH3)CH2SCH3(S) | H | H | 3-I | 2-Cl | H | CF3 | H | CF3 | H | |
| 445 | CH(CH3)CH2SCH3(S) | H | H | 3-I | 2-Cl | H | C2F5 | H | C2F5 | H | |
| 446 | CH(CH3)CH2SCH3(S) | H | H | 3-F | 2-Cl | H | CF3 | H | CF3 | H | |
| 447 | CH(CH3)CH2SCH3(S) | H | H | 3-F | 2-Cl | H | C2F5 | H | C2F5 | H | |
| 448 | CH(CH3)CH2SCH3(S) | H | H | 3-NO2 | 2-Cl | H | CF3 | H | CF3 | H | |
| 449 | CH(CH3)CH2SCH3(S) | H | H | 3-NO2 | 2-Cl | H | C2F5 | H | C2F5 | H | |
| 450 | CH(CH3)CH2SCH3(S) | H | H | 3-MeSO2O | 2-Cl | H | CF3 | H | CF3 | H | |
| 451 | CH(CH3)CH2SCH3(S) | H | H | 3-MeSO2O | 2-Cl | H | C2F5 | H | C2F5 | H | |
| 452 | CH(CH3)CH2SCH3(S) | H | H | 3-MeSO2 | 2-Cl | H | CF3 | H | CF3 | H | |
| 453 | CH(CH3)CH2SCH3(S) | H | H | 3-MeSO2 | 2-Cl | H | C2F5 | H | C2F5 | H | |
| 454 | CH(CH3)CH2SCH3(S) | CH3 | H | 3-Cl | 2-Cl | H | CF3 | H | CF3 | H | |
| 455 | CH(CH3)CH2SCH3(S) | CH3 | H | 3-Cl | 2-Cl | H | C2F5 | H | C2F5 | H | |
| 456 | CH(CH3)CH2SCH3(S) | CF3 | H | 3-Cl | 2-Cl | H | CF3 | H | CF3 | H | |
| 457 | CH(CH3)CH2SCH3(S) | CF3 | H | 3-Cl | 2-Cl | H | C2F5 | H | C2F5 | H | |
| 458 | CH(CH3)CH2SCH3(S) | CF3 | OH | 3-Cl | 2-Cl | H | CF3 | H | CF3 | H | |
| 459 | CH(CH3)CH2SCH3(S) | CF3 | OH | 3-Cl | 2-Cl | H | C2F5 | H | C2F5 | H | |

TABLE 2

| | R1 | R2 | R3 | X | Y | Z1 | Z2 | Z3 | Z4 | Z5 | mp |
|---|---|---|---|---|---|---|---|---|---|---|---|
| 460 | CH(CH3)CH2SCH3(S) | H | H | 3-Cl | 2-CH3 | H | H | CF3 | H | H | |
| 461 | CH(CH3)CH2SOCH3(S) | H | H | 3-Cl | 2-CH3 | H | H | CF3 | H | H | |
| 462 | CH(CH3)CH2SO2CH3(S) | H | H | 3-Cl | 2-CH3 | H | H | CF3 | H | H | |
| 463 | CH(CH3)CH2SCH3(S) | H | H | 3-Cl | 2-CH3 | H | CF3 | H | CF3 | H | 73-79 |
| 464 | CH(CH3)CH2SOCH3(S) | H | H | 3-Cl | 2-CH3 | H | CF3 | H | CF3 | H | 58-64 |
| 465 | CH(CH3)CH2SO2CH3(S) | H | H | 3-Cl | 2-CH3 | H | CF3 | H | CF3 | H | |
| 466 | CH(CH3)CH2SC2H5(S) | H | H | 3-Cl | 2-CH3 | H | CF3 | H | CF3 | H | |
| 467 | C(CH3)2CH2SCH3 | H | H | 3-Cl | 2-CH3 | H | CF3 | H | CF3 | H | |
| 468 | C(CH3)2CH2SOCH3 | H | H | 3-Cl | 2-CH3 | H | CF3 | H | CF3 | H | |
| 469 | C(CH3)2CH2SO2CH3 | H | H | 3-Cl | 2-CH3 | H | CF3 | H | CF3 | H | |
| 470 | CH(CH3)CH2SCH3(S) | H | H | 3-Cl | 2-CH3 | H | CF3 | CF3 | H | H | |
| 471 | CH(CH3)CH2SCH3(S) | H | H | 3-Cl | 2-CH3 | H | C2F5 | H | H | H | |
| 472 | CH(CH3)CH2SCH3(S) | H | H | 3-Cl | 2-CH3 | H | H | C2F5 | H | H | |
| 473 | iso-Pr | H | H | 3-Cl | 2-CH3 | H | C2F5 | H | C2F5 | H | |
| 474 | CH(CH3)CH2SCH3(S) | H | H | 3-Cl | 2-CH3 | H | C2F5 | H | C2F5 | H | |
| 475 | CH(CH3)CH2SOCH3(S) | H | H | 3-Cl | 2-CH3 | H | C2F5 | H | C2F5 | H | |
| 476 | CH(CH3)CH2SO2CH3(S) | H | H | 3-Cl | 2-CH3 | H | C2F5 | H | C2F5 | H | |
| 477 | C(CH3)2CH2SCH3 | H | H | 3-Cl | 2-CH3 | H | C2F5 | H | C2F5 | H | |
| 478 | C(CH3)2CH2SOCH3 | H | H | 3-Cl | 2-CH3 | H | C2F5 | H | C2F5 | H | |
| 479 | C(CH3)2CH2SO2CH3 | H | H | 3-Cl | 2-CH3 | H | C2F5 | H | C2F5 | H | |
| 480 | C(CH3)2CH2SCH3 | H | H | 3-Cl | 2-CH3 | H | C2F5 | C2F5 | H | H | |
| 481 | CH(CH3)CH2SCH3(S) | H | H | 3-Cl | 2-CH3 | H | C3F7-n | H | H | H | |
| 482 | C(CH3)2CH2SCH3 | H | H | 3-Cl | 2-CH3 | H | H | C3F7-n | H | H | |
| 483 | C(CH3)2CH2SCH3 | H | H | 3-Cl | 2-CH3 | H | C3F7-n | H | C3F7-n | H | |
| 484 | C(CH3)2CH2SCH3 | H | H | 3-Cl | 2-CH3 | H | C3F7-i | H | H | H | |
| 485 | C(CH3)2CH2SCH3 | H | H | 3-Cl | 2-CH3 | H | H | C3F7-i | H | H | |
| 486 | C(CH3)2CH2SCH3 | H | H | 3-Cl | 2-CH3 | H | C4F9-n | H | H | H | |
| 487 | C(CH3)2CH2SCH3 | H | H | 3-Cl | 2-CH3 | H | H | C4F9-n | H | H | |
| 488 | C(CH3)2CH2SCH3 | H | H | 3-Cl | 2-CH3 | H | C4F9-n | H | C4F9-n | H | |
| 489 | C(CH3)2CH2SCH3 | H | H | 3-Cl | 2-CH3 | H | H | OCF3 | H | H | |
| 490 | C(CH3)2CH2SCH3 | H | H | 3-Cl | 2-CH3 | H | H | SCF3 | H | H | |
| 491 | C(CH3)2CH2SCH3 | H | H | 3-Cl | 2-CH3 | H | H | SC2F5 | H | H | |
| 492 | C(CH3)2CH2SCH3 | H | H | 3-Cl | 2-CH3 | H | C2F5 | Cl | C2F5 | H | |
| 493 | CH(CH3)CH2SCH3 | H | H | 3-Cl | 2-CH3 | H | C2F5 | Br | C2F5 | H | |
| 494 | CH(CH3)CH2SCH3 | H | H | 3-Cl | 2-CH3 | H | Cl | C2F5 | Cl | H | |
| 495 | CH(CH3)CH2SCH3 | H | H | 3-Cl | 2-CH3 | H | Cl | C3F7-n | Cl | H | |
| 496 | CH(CH3)CH2SCH3 | H | H | 3-Cl | 2-CH3 | H | Cl | H | Cl | H | |
| 497 | CH(CH3)CH2SCH3 | H | H | 3-Cl | 2-CH3 | H | Br | H | Br | H | |
| 498 | CH(CH3)CH2SCH3 | H | H | 3-Cl | 2-CH3 | H | Cl | Cl | Cl | H | |
| 499 | CH(CH3)CH2SCH3 | H | H | 3-Cl | 2-CH3 | H | Br | Br | Br | H | |
| 500 | C(CH3)2CH2SCH3 | H | H | 3-Br | 2-CH3 | H | CF3 | H | CF3 | H | |
| 501 | CH(CH3)CH2SOCH3(S) | H | H | 3-Br | 2-CH3 | H | CF3 | H | CF3 | H | |
| 502 | CH(CH3)CH2SO2CH3(S) | H | H | 3-Br | 2-CH3 | H | CF3 | H | CF3 | H | |
| 503 | CH(CH3)CH2SCH3(S) | H | H | 3-Br | 2-CH3 | H | C2F5 | H | C2F5 | H | |
| 504 | CH(CH3)CH2SOCH3(S) | H | H | 3-Br | 2-CH3 | H | C2F5 | H | C2F5 | H | |
| 505 | CH(CH3)CH2SO2CH3(S) | H | H | 3-Br | 2-CH3 | H | C2F5 | H | C2F5 | H | |
| 506 | C(CH3)2CH2SCH3 | H | H | 3-Br | 2-CH3 | H | C2F5 | H | C2F5 | H | |
| 507 | CH(CH3)CH2SCH3(S) | H | H | 3-Br | 2-CH3 | H | H | C3F7-n | H | H | |
| 508 | CH(CH3)CH2SCH3(S) | H | H | 3-I | 2-CH3 | H | C2F5 | H | C2F5 | H | |
| 509 | C(CH3)2CH2SCH3 | H | H | 3-I | 2-CH3 | H | C2F5 | H | C2F5 | H | |
| 510 | CH(CH3)CH2SCH3(S) | H | H | 3-I | 2-CH3 | H | C2F5 | C2F5 | H | H | |
| 511 | CH(CH3)CH2SCH3(S) | H | H | 3-I | 2-CH3 | H | H | C3F7-n | H | H | |
| 512 | CH(CH3)CH2SCH3(S) | H | H | 3-I | 2-CH3 | H | C3F7-n | H | C3F7-n | H | |
| 513 | CH(CH3)CH2SCH3(S) | H | H | 3-I | 2-CH3 | H | H | C3F7-i | H | H | |
| 514 | CH(CH3)CH2SCH3(S) | H | H | 3-F | 2-CH3 | H | CF3 | H | CF3 | H | |
| 515 | CH(CH3)CH2SOCH3(S) | H | H | 3-F | 2-CH3 | H | CF3 | H | CF3 | H | |
| 516 | CH(CH3)CH2SO2CH3(S) | H | H | 3-F | 2-CH3 | H | CF3 | H | CF3 | H | |
| 517 | CH(CH3)CH2SCH3(S) | H | H | 3-F | 2-CH3 | H | C2F5 | H | C2F5 | H | |
| 518 | CH(CH3)CH2SOCH3(S) | H | H | 3-F | 2-CH3 | H | C2F5 | H | C2F5 | H | |
| 519 | CH(CH3)CH2SO2CH3(S) | H | H | 3-F | 2-CH3 | H | C2F5 | H | C2F5 | H | |
| 520 | CH(CH3)CH2SCH3(S) | H | H | 3-NO2 | 2-CH3 | H | CF3 | H | CF3 | H | |
| 521 | CH(CH3)CH2SCH3(S) | H | H | 3-NO2 | 2-CH3 | H | C2F5 | H | C2F5 | H | |

TABLE 2-continued

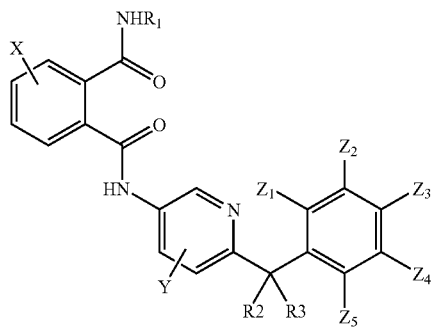

| | R1 | R2 | R3 | X | Y | Z1 | Z2 | Z3 | Z4 | Z5 | mp |
|---|---|---|---|---|---|---|---|---|---|---|---|
| 522 | CH(CH3)CH2SCH3 | H | H | 3-MeSO2O | 2-CH3 | H | CF3 | H | CF3 | H | |
| 523 | CH(CH3)CH2SCH3 | H | H | 3-MeSO2O | 2-CH3 | H | C2F5 | H | C2F5 | H | |
| 524 | CH(CH3)CH2SCH3 | H | H | 3-MeS | 2-CH3 | H | CF3 | H | CF3 | H | |
| 525 | CH(CH3)CH2SCH3 | H | H | 3-MeS | 2-CH3 | H | C2F5 | H | C2F5 | H | |
| 526 | CH(CH3)CH2SCH3 | H | H | 3-MeSO | 2-CH3 | H | CF3 | H | CF3 | H | |
| 527 | CH(CH3)CH2SCH3 | H | H | 3-MeSO | 2-CH3 | H | C2F5 | H | C2F5 | H | |
| 528 | CH(CH3)CH2SCH3 | H | H | 3-MeSO2 | 2-CH3 | H | CF3 | H | CF3 | H | |
| 529 | CH(CH3)CH2SCH3 | H | H | 3-MeSO2 | 2-CH3 | H | C2F5 | H | C2F5 | H | |
| 530 | C(CH3)CH2SCH3(S) | CH3 | H | 3-Cl | 2-CH3 | H | CF3 | H | CF3 | H | |
| 531 | CH(CH3)CH2SOCH3(S) | CH3 | H | 3-Cl | 2-CH3 | H | CF3 | H | CF3 | H | |
| 532 | CH(CH3)CH2SO2CH3(S) | CH3 | H | 3-Cl | 2-CH3 | H | CF3 | H | CF3 | H | |
| 533 | C(CH3)2CH2SCH3 | CH3 | H | 3-Cl | 2-CH3 | H | CF3 | H | CF3 | H | |
| 534 | C(CH3)2CH2SOCH3 | CH3 | H | 3-Cl | 2-CH3 | H | CF3 | H | CF3 | H | |
| 535 | C(CH3)2CH2SO2CH3 | CH3 | H | 3-Cl | 2-CH3 | H | CF3 | H | CF3 | H | |
| 536 | CH(CH3)CH2SCH3(S) | CH3 | H | 3-Cl | 2-CH3 | H | C2F5 | H | C2F5 | H | |
| 537 | CH(CH3)CH2SOCH3(S) | CH3 | H | 3-Cl | 2-CH3 | H | C2F5 | H | C2F5 | H | |
| 538 | CH(CH3)CH2SO2CH3(S) | CH3 | H | 3-Cl | 2-CH3 | H | C2F5 | H | C2F5 | H | |
| 539 | C(CH3)2CH2SCH3 | CH3 | H | 3-Cl | 2-CH3 | H | C2F5 | H | C2F5 | H | |
| 540 | C(CH3)2CH2SOCH3 | CH3 | H | 3-Cl | 2-CH3 | H | C2F5 | H | C2F5 | H | |
| 541 | C(CH3)2CH2SO2CH3 | CH3 | H | 3-Cl | 2-CH3 | H | C2F5 | H | C2F5 | H | |
| 542 | CH(CH3)CH2SCH3(S) | CH3 | H | 3-Cl | 2-CH3 | H | C2F5 | C2F5 | H | H | |
| 543 | CH(CH3)CH2SCH3(S) | CH3 | H | 3-Br | 2-CH3 | H | CF3 | H | CF3 | H | |
| 544 | CH(CH3)CH2SOCH3(S) | CH3 | H | 3-Br | 2-CH3 | H | CF3 | H | CF3 | H | |
| 545 | CH(CH3)CH2SO2CH3(S) | CH3 | H | 3-Br | 2-CH3 | H | CF3 | H | CF3 | H | |
| 546 | CH(CH3)CH2SCH3(S) | CH3 | H | 3-Br | 2-CH3 | H | C2F5 | H | C2F5 | H | |
| 547 | CH(CH3)CH2SOCH3(S) | CH3 | H | 3-Br | 2-CH3 | H | C2F5 | H | C2F5 | H | |
| 548 | CH(CH3)CH2SO2CH3(S) | CH3 | H | 3-Br | 2-CH3 | H | C2F5 | H | C2F5 | H | |
| 549 | C(CH3)2CH2SCH3 | CH3 | H | 3-I | 2-CH3 | H | CF3 | H | CF3 | H | |
| 550 | C(CH3)2CH2SOCH3 | CH3 | H | 3-I | 2-CH3 | H | CF3 | H | CF3 | H | |
| 551 | C(CH3)2CH2SO2CH3 | CH3 | H | 3-I | 2-CH3 | H | CF3 | H | CF3 | H | |
| 552 | C(CH3)2CH2SCH3 | CH3 | H | 3-I | 2-CH3 | H | C2F5 | H | C2F5 | H | |
| 553 | C(CH3)2CH2SOCH3 | CH3 | H | 3-I | 2-CH3 | H | C2F5 | H | C2F5 | H | |
| 554 | C(CH3)2CH2SO2CH3 | CH3 | H | 3-I | 2-CH3 | H | C2F5 | H | C2F5 | H | |
| 555 | CH(CH3)CH2SCH3 | CH3 | H | 3-F | 2-CH3 | H | CF3 | H | CF3 | H | |
| 556 | CH(CH3)CH2SCH3 | CH3 | H | 3-F | 2-CH3 | H | C2F5 | H | C2F5 | H | |
| 557 | CH(CH3)CH2SCH3 | CH3 | H | 3-NO2 | 2-CH3 | H | CF3 | H | CF3 | H | |
| 558 | CH(CH3)CH2SCH3 | CH3 | H | 3-NO2 | 2-CH3 | H | C2F5 | H | C2F5 | H | |
| 559 | CH(CH3)CH2SCH3 | CF3 | H | 3-Cl | 2-CH3 | H | CF3 | H | CF3 | H | |
| 560 | CH(CH3)CH2SCH3 | CF3 | H | 3-Cl | 2-CH3 | H | C2F5 | H | C2F5 | H | |
| 561 | C(CH3)2CH2SCH3 | CF3 | H | 3-Br | 2-CH3 | H | CF3 | H | CF3 | H | |
| 562 | C(CH3)2CH2SCH3 | CF3 | H | 3-Br | 2-CH3 | H | C2F5 | H | C2F5 | H | |
| 563 | C(CH3)2CH2SCH3 | CF3 | H | 3-I | 2-CH3 | H | CF3 | H | CF3 | H | |
| 564 | C(CH3)2CH2SCH3 | CF3 | H | 3-I | 2-CH3 | H | C2F5 | H | C2F5 | H | |
| 565 | C(CH3)2CH2SCH3 | H | OH | 3-Cl | 2-CH3 | H | CF3 | H | CF3 | H | |
| 566 | C(CH3)2CH2SCH3 | H | OH | 3-Cl | 2-CH3 | H | C2F5 | H | C2F5 | H | |
| 567 | C(CH3)2CH2SCH3 | CF3 | OH | 3-Cl | 2-CH3 | H | CF3 | H | CF3 | H | |
| 568 | C(CH3)2CH2SCH3 | CF3 | OH | 3-Cl | 2-CH3 | H | C2F5 | H | C2F5 | H | |
| 569 | C(CH3)2CH2SCH3 | CF3 | OH | 3-I | 2-CH3 | H | CF3 | H | CF3 | H | |
| 570 | C(CH3)2CH2SCH3 | CF3 | OH | 3-I | 2-CH3 | H | C2F5 | H | C2F5 | H | |
| 571 | C(CH3)2CH2SCH3 | CH3 | H | 3-Cl | 2-Cl | H | CF3 | H | CF3 | H | |
| 572 | C(CH3)2CH2SCH3 | CH3 | H | 3-Cl | 2-Cl | H | C2F5 | H | C2F5 | H | |

TABLE 3

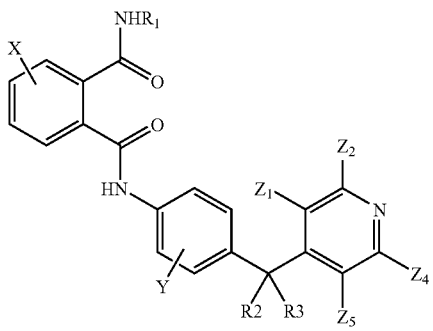

| | R1 | R2 | R3 | X | Y | Z1 | Z2 | Z4 | Z5 | mp |
|---|---|---|---|---|---|---|---|---|---|---|
| 573 | CH(CH3)CH2SCH3(S) | H | H | 3-Cl | 2-CH3 | H | C2F5 | H | H | |
| 574 | CH(CH3)CH2SOCH3(S) | H | H | 3-Cl | 2-CH3 | H | C2F5 | H | H | |
| 575 | CH(CH3)CH2SO2CH3(S) | H | H | 3-Cl | 2-CH3 | H | C2F5 | H | H | |
| 576 | CH(CH3)CH2SCH3 | H | H | 3-Cl | 2-CH3 | H | CF3 | CF3 | H | |
| 577 | CH(CH3)CH2SOCH3 | H | H | 3-Cl | 2-CH3 | H | CF3 | CF3 | H | |
| 578 | CH(CH3)CH2SO2CH3 | H | H | 3-Cl | 2-CH3 | H | CF3 | CF3 | H | |
| 579 | C(CH3)2CH2SCH3 | H | H | 3-Cl | 2-CH3 | H | CF3 | CF3 | H | |
| 580 | C(CH3)2CH2SOCH3 | H | H | 3-Cl | 2-CH3 | H | CF3 | CF3 | H | |
| 581 | C(CH3)2CH2SO2CH3 | H | H | 3-Cl | 2-CH3 | H | CF3 | CF3 | H | |
| 582 | iso-Pr | H | H | 3-Cl | 2-CH3 | H | C2F5 | C2F5 | H | |
| 583 | CH(CH3)CH2SCH3(S) | H | H | 3-Cl | 2-CH3 | H | C2F5 | C2F5 | H | 64-70 |
| 584 | CH(CH3)CH2SOCH3(S) | H | H | 3-Cl | 2-CH3 | H | C2F5 | C2F5 | H | 91-95 |
| 585 | CH(CH3)CH2SO2CH3(S) | H | H | 3-Cl | 2-CH3 | H | C2F5 | C2F5 | H | 85-89 |
| 586 | C(CH3)2CH2SCH3 | H | H | 3-Cl | 2-CH3 | H | C2F5 | C2F5 | H | |
| 587 | C(CH3)2CH2SOCH3 | H | H | 3-Cl | 2-CH3 | H | C2F5 | C2F5 | H | |
| 588 | C(CH3)2CH2SO2CH3 | H | H | 3-Cl | 2-CH3 | H | C2F5 | C2F5 | H | |
| 589 | CH(CH3)CH2SCH3(S) | H | H | 3-Cl | 2-CH3 | H | C3F7-n | H | H | |
| 590 | C(CH3)2CH2SCH3 | H | H | 3-Cl | 2-CH3 | H | C3F7-n | H | H | |
| 591 | CH(CH3)CH2SCH3(S) | H | H | 3-Cl | 2-CH3 | H | C3F7-n | C3F7-n | H | |
| 592 | CH(CH3)CH2SCH3(S) | H | H | 3-Cl | 2-CH3 | H | C4F9-n | H | H | |
| 593 | CH(CH3)CH2SCH3(S) | H | H | 3-Cl | 2-CH3 | H | C4F9-n | C4F9-n | H | |
| 594 | CH(CH3)CH2SCH3(S) | H | H | 3-Cl | 2-CH3 | H | SCF3 | SCF3 | H | |
| 595 | CH(CH3)CH2SCH3(S) | H | H | 3-Cl | 2-CH3 | H | Cl | Cl | H | 83-88 |
| 596 | CH(CH3)CH2SCH3(S) | H | H | 3-Br | 2-CH3 | H | CF3 | CF3 | H | |
| 597 | CH(CH3)CH2SCH3(S) | H | H | 3-Br | 2-CH3 | H | C2F5 | C2F5 | H | |
| 598 | C(CH3)2CH2SCH3 | H | H | 3-I | 2-CH3 | H | CF3 | CF3 | H | |
| 599 | C(CH3)2CH2SCH3 | H | H | 3-I | 2-CH3 | H | C2F5 | C2F5 | H | |
| 600 | CH(CH3)CH2SCH3 | H | H | 3-F | 2-CH3 | H | CF3 | CF3 | H | |
| 601 | CH(CH3)CH2SCH3 | H | H | 3-F | 2-CH3 | H | C2F5 | C2F5 | H | |
| 602 | CH(CH3)CH2SCH3 | H | H | 3-NO2 | 2-CH3 | H | CF3 | CF3 | H | |
| 603 | CH(CH3)CH2SCH3 | H | H | 3-NO2 | 2-CH3 | H | C2F5 | C2F5 | H | |
| 604 | CH(CH3)CH2SCH3 | H | H | 3-MeSO2O | 2-CH3 | H | C2F5 | C2F5 | H | |
| 605 | CH(CH3)CH2SCH3 | H | H | 3-MeS | 2-CH3 | H | C2F5 | C2F5 | H | |
| 606 | CH(CH3)CH2SCH3 | H | H | 3-MeSO | 2-CH3 | H | C2F5 | C2F5 | H | |
| 607 | CH(CH3)CH2SCH3 | H | H | 3-MeSO2 | 2-CH3 | H | C2F5 | C2F5 | H | |
| 608 | CH(CH3)CH2SCH3 | CH3 | H | 3-Cl | 2-CH3 | H | CF3 | CF3 | H | |
| 609 | CH(CH3)CH2SCH3 | CH3 | H | 3-Cl | 2-CH3 | H | C2F5 | C2F5 | H | |
| 610 | CH(CH3)CH2SCH3 | CH3 | H | 3-Br | 2-CH3 | H | CF3 | CF3 | H | |
| 611 | CH(CH3)CH2SCH3 | CH3 | H | 3-Br | 2-CH3 | H | C2F5 | C2F5 | H | |
| 612 | CH(CH3)CH2SCH3 | CH3 | H | 3-I | 2-CH3 | H | C2F5 | C2F5 | H | |
| 613 | CH(CH3)CH2SCH3 | CF3 | H | 3-Cl | 2-CH3 | H | C2F5 | C2F5 | H | |
| 614 | CH(CH3)CH2SO2CH3(S) | CF3 | H | 3-Br | 2-CH3 | H | C2F5 | C2F5 | H | |
| 615 | CH(CH3)CH2SCH3 | CF3 | H | 3-I | 2-CH3 | H | C2F5 | C2F5 | H | |
| 616 | CH(CH3)CH2SCH3 | H | OH | 3-Cl | 2-CH3 | H | C2F5 | C2F5 | H | |
| 617 | CH(CH3)CH2SCH3 | H | OH | 3-Br | 2-CH3 | H | C2F5 | C2F5 | H | |
| 618 | CH(CH3)CH2SCH3 | H | OH | 3-I | 2-CH3 | H | C2F5 | C2F5 | H | |
| 619 | CH(CH3)CH2SCH3 | CF3 | OH | 3-Cl | 2-CH3 | H | CF3 | CF3 | H | |
| 620 | CH(CH$_3$)CH$_2$SCH$_3$ | CF3 | OH | 3-Cl | 2-CH3 | H | C2F5 | C2F5 | H | |
| 621 | CH(CH3)CH2SCH3 | CF3 | OH | 3-I | 2-CH3 | H | C2F5 | C2F5 | H | |
| 622 | CH(CH3)CH2SCH3 | H | H | 3-Cl | 2-Cl | H | C2F5 | C2F5 | H | |

TABLE 4

| | R1 | R2 | R3 | X | Y | Z1 | Z3 | Z4 | Z5 | mp |
|---|---|---|---|---|---|---|---|---|---|---|
| 623 | CH(CH3)CH2SCH3 | H | H | 3-Cl | 2-CH3 | H | CF3 | H | H | |
| 624 | CH(CH3)CH2SOCH3 | H | H | 3-Cl | 2-CH3 | H | CF3 | H | H | |
| 625 | CH(CH3)CH2SO2CH3 | H | H | 3-Cl | 2-CH3 | H | CF3 | H | H | |
| 626 | CH(CH3)CH2SCH3(S) | H | H | 3-Cl | 2-CH3 | H | C2F5 | H | H | |
| 627 | CH(CH3)CH2SOCH3(S) | H | H | 3-Cl | 2-CH3 | H | C2F5 | H | H | |
| 628 | CH(CH3)CH2SO2CH3(S) | H | H | 3-Cl | 2-CH3 | H | C2F5 | H | H | |
| 629 | CH(CH3)CH2SCH3(S) | H | H | 3-Cl | 2-CH3 | H | C2F5 | C2F5 | H | |
| 630 | CH(CH3)CH2SOCH3(S) | H | H | 3-Cl | 2-CH3 | H | C2F5 | C2F5 | H | |
| 631 | CH(CH3)CH2SO2CH3(S) | H | H | 3-Cl | 2-CH3 | H | C2F5 | C2F5 | H | |
| 632 | C(CH3)2CH2SCH3 | H | H | 3-Cl | 2-CH3 | H | C2F5 | C2F5 | H | |
| 633 | C(CH3)2CH2SOCH3 | H | H | 3-Cl | 2-CH3 | H | C2F5 | C2F5 | H | |
| 634 | C(CH3)2CH2SO2CH3 | H | H | 3-Cl | 2-CH3 | H | C2F5 | C2F5 | H | |
| 635 | CH(CH3)CH2SCH3(S) | H | H | 3-Cl | 2-CH3 | H | C3F7-n | H | H | 83-88 |
| 636 | CH(CH3)CH2SOCH3(S) | H | H | 3-Cl | 2-CH3 | H | C3F7-n | H | H | |
| 637 | CH(CH3)CH2SO2CH3(S) | H | H | 3-Cl | 2-CH3 | H | C3F7-n | H | H | |
| 638 | CH(CH3)CH2SCH3 | H | H | 3-Cl | 2-CH3 | H | C4F9-n | H | H | |
| 639 | CH(CH3)CH2SCH3 | H | H | 3-Cl | 2-CH3 | H | SCF3 | H | H | |
| 640 | CH(CH3)CH2SCH3 | H | H | 3-Cl | 2-CH3 | H | SC2F5 | H | H | |
| 641 | CH(CH3)CH2SCH3 | H | H | 3-Br | 2-CH3 | H | C2F5 | C2F5 | H | |
| 642 | CH(CH3)CH2SCH3 | H | H | 3-I | 2-CH3 | H | C2F5 | C2F5 | H | |
| 643 | CH(CH3)CH2SCH3 | H | H | 3-F | 2-CH3 | H | C2F5 | C2F5 | H | |
| 644 | CH(CH3)CH2SCH3 | H | H | 3-NO2 | 2-CH3 | H | C2F5 | C2F5 | H | |
| 645 | CH(CH3)CH2SCH3 | H | H | 3-MeSO2O | 2-CH3 | H | C2F5 | C2F5 | H | |
| 646 | CH(CH3)CH2SCH3 | CH3 | H | 3-Cl | 2-CH3 | H | C2F5 | H | H | |
| 647 | CH(CH3)CH2SCH3 | CH3 | H | 3-Cl | 2-CH3 | H | C2F5 | C2F5 | H | |
| 648 | CH(CH3)CH2SCH3 | CH3 | H | 3-Cl | 2-CH3 | H | C3F7-n | H | H | |
| 649 | CH(CH3)CH2SCH3 | CH3 | H | 3-Br | 2-CH3 | H | C2F5 | C2F5 | H | |
| 650 | CH(CH3)CH2SCH3 | CH3 | H | 3-I | 2-CH3 | H | C2F5 | C2F5 | H | |
| 651 | CH(CH3)CH2SCH3 | CF3 | H | 3-Cl | 2-CH3 | H | C2F5 | C2F5 | H | |
| 652 | CH(CH3)CH2SCH3 | CF3 | H | 3-Br | 2-CH3 | H | C2F5 | C2F5 | H | |
| 653 | CH(CH3)CH2SCH3 | CF3 | H | 3-I | 2-CH3 | H | C2F5 | C2F5 | H | |
| 654 | CH(CH3)CH2SCH3(S) | H | OH | 3-Cl | 2-CH3 | H | C2F5 | C2F5 | H | |
| 655 | CH(CH3)CH2SCH3(S) | CF3 | OH | 3-Cl | 2-CH3 | H | C2F5 | C2F5 | H | |
| 656 | CH(CH3)CH2SCH3(S) | CF3 | OH | 3-I | 2-CH3 | H | C2F5 | C2F5 | H | |
| 657 | CH(CH3)CH2SCH3(S) | H | H | 3-Cl | 2-Cl | H | C2F5 | C2F5 | H | |

TABLE 5

| | R1 | R2 | R3 | X | Y | Z2 | Z3 | Z4 | Z5 | mp |
|---|---|---|---|---|---|---|---|---|---|---|
| 658 | CH(CH3)CH2SCH3 | H | H | 3-Cl | 2-CH3 | CF3 | H | H | H | |
| 659 | CH(CH3)CH2SOCH3 | H | H | 3-Cl | 2-CH3 | CF3 | H | H | H | |
| 660 | CH(CH3)CH2SO2CH3 | H | H | 3-Cl | 2-CH3 | CF3 | H | H | H | |
| 661 | CH(CH3)CH2SCH3(S) | H | H | 3-Cl | 2-CH3 | C2F5 | H | H | H | 73-76 |
| 662 | CH(CH3)CH2SOCH3(S) | H | H | 3-Cl | 2-CH3 | C2F5 | H | H | H | |

TABLE 5-continued

| | R1 | R2 | R3 | X | Y | Z2 | Z3 | Z4 | Z5 | mp |
|---|---|---|---|---|---|---|---|---|---|---|
| 663 | CH(CH3)CH2SO2H3(S) | H | H | 3-Cl | 2-CH3 | C2F5 | H | H | H | |
| 664 | CH(CH3)CH2SCH3(S) | H | H | 3-Cl | 2-CH3 | C2F5 | C2F5 | H | H | |
| 665 | CH(CH3)CH2SCH3(S) | H | H | 3-Cl | 2-CH3 | C3F7-n | H | H | H | |
| 666 | CH(CH3)CH2SCH3(S) | H | H | 3-Cl | 2-CH3 | H | C3F7-i | H | H | |
| 667 | CH(CH3)CH2SCH3(S) | H | H | 3-Cl | 2-CH3 | SCF3 | H | H | H | |
| 668 | CH(CH3)CH2SCH3 | H | H | 3-Cl | 2-CH3 | SC2F5 | H | H | H | |
| 669 | CH(CH3)CH2SCH3(S) | H | H | 3-Br | 2-CH3 | C2F5 | H | H | H | |
| 670 | CH(CH3)CH2SCH3(S) | H | H | 3-Br | 2-CH3 | C3F7-n | H | H | H | |
| 671 | CH(CH3)CH2SCH3(S) | H | H | 3-I | 2-CH3 | C2F5 | H | H | H | |
| 672 | CH(CH3)CH2SCH3(S) | H | H | 3-I | 2-CH3 | C2F5 | C2F5 | H | H | |
| 673 | CH(CH3)CH2SCH3 | H | H | 3-I | 2-CH3 | C3F7-n | H | H | H | |
| 674 | CH(CH3)CH2SCH3 | H | H | 3-I | 2-CH3 | C4F9-n | H | H | H | |
| 675 | CH(CH3)CH2SCH3 | H | H | 3-F | 2-CH3 | C3F7-n | H | H | H | |
| 676 | CH(CH3)CH2SCH3 | H | H | 3-NO2 | 2-CH3 | C3F7-n | H | H | H | |
| 677 | CH(CH3)CH2SCH3 | H | H | 3-MeSO2O | 2-CH3 | C3F7-n | H | H | H | |
| 678 | CH(CH3)CH2SCH3 | CH3 | H | 3-Cl | 2-CH3 | C2F5 | H | H | H | |
| 679 | CH(CH3)CH2SCH3 | CH3 | H | 3-Cl | 2-CH3 | C3F7-n | H | H | H | |
| 680 | CH(CH3)CH2SCH3 | CH3 | H | 3-Cl | 2-CH3 | H | C3F7-i | H | H | |
| 681 | CH(CH3)CH2SCH3 | CH3 | H | 3-Br | 2-CH3 | C2F5 | H | H | H | |
| 682 | CH(CH3)CH2SCH3 | CH3 | H | 3-Br | 2-CH3 | C3F7-n | H | H | H | |
| 683 | CH(CH3)CH2SOCH3(S) | CH3 | H | 3-I | 2-CH3 | C2F5 | H | H | H | |
| 684 | CH(CH3)CH2SCH3(S) | CH3 | H | 3-I | 2-CH3 | C3F7-n | H | H | H | |
| 685 | CH(CH3)CH2SCH3(S) | CF3 | H | 3-Cl | 2-CH3 | C2F5 | H | H | H | |
| 686 | CH(CH3)CH2SCH3(S) | CF3 | H | 3-Cl | 2-CH3 | C3F7-n | H | H | H | |
| 687 | CH(CH3)CH2SCH3(S) | CF3 | H | 3-Cl | 2-CH3 | H | C3F7-i | H | H | |
| 688 | CH(CH3)CH2SO2H3(S) | CF3 | H | 3-Br | 2-CH3 | C2F5 | H | H | H | |
| 689 | CH(CH3)CH2SCH3(S) | CF3 | H | 3-Br | 2-CH3 | C3F7-n | H | H | H | |
| 690 | CH(CH3)CH2SCH3(S) | CF3 | H | 3-I | 2-CH3 | C2F5 | H | H | H | |
| 691 | CH(CH3)CH2SCH3(S) | CF3 | OH | 3-Cl | 2-CH3 | C2F5 | H | H | H | |
| 692 | CH(CH3)CH2SCH3(S) | CF3 | OH | 3-Cl | 2-CH3 | C3F7-n | H | H | H | |
| 693 | CH(CH3)CH2SCH3(S) | H | H | 3-Cl | 2-Cl | C3F7-n | H | H | H | |

TABLE 6

| | R1 | R2 | R3 | X | Y | Z1 | Z2 | Z4 | Z5 | mp |
|---|---|---|---|---|---|---|---|---|---|---|
| 694 | CH(CH3)CH2SCH3(S) | H | H | 3-Cl | 2-CH3 | H | C2F5 | H | H | |
| 695 | CH(CH3)CH2SOCH3(S) | H | H | 3-Cl | 2-CH3 | H | C2F5 | H | H | |
| 696 | CH(CH3)CH2SO2CH3(S) | H | H | 3-Cl | 2-CH3 | H | C2F5 | H | H | |
| 697 | CH(CH3)CH2SCH3 | H | H | 3-Cl | 2-CH3 | H | CF3 | CF3 | H | |
| 698 | CH(CH3)CH2SOCH3 | H | H | 3-Cl | 2-CH3 | H | CF3 | CF3 | H | |
| 699 | CH(CH3)CH2SO2CH3 | H | H | 3-Cl | 2-CH3 | H | CF3 | CF3 | H | |
| 700 | C(CH3)2CH2SCH3 | H | H | 3-Cl | 2-CH3 | H | CF3 | CF3 | H | |
| 701 | C(CH3)2CH2SOCH3 | H | H | 3-Cl | 2-CH3 | H | CF3 | CF3 | H | |
| 702 | C(CH3)2CH2SO2CH3 | H | H | 3-Cl | 2-CH3 | H | CF3 | CF3 | H | |

TABLE 6-continued

| | R1 | R2 | R3 | X | Y | Z1 | Z2 | Z4 | Z5 | mp |
|---|---|---|---|---|---|---|---|---|---|---|
| 703 | iso-Pro | H | H | 3-Cl | 2-CH3 | H | C2F5 | C2F5 | H | |
| 704 | CH(CH3)CH2SCH3(S) | H | H | 3-Cl | 2-CH3 | H | C2F5 | C2F5 | H | |
| 705 | CH(CH3)CH2SOCH3(S) | H | H | 3-Cl | 2-CH3 | H | C2F5 | C2F5 | H | |
| 706 | CH(CH3)CH2SO2CH3(S) | H | H | 3-Cl | 2-CH3 | H | C2F5 | C2F5 | H | |
| 707 | C(CH3)2CH2SCH3 | H | H | 3-Cl | 2-CH3 | H | C2F5 | C2F5 | H | |
| 708 | C(CH3)2CH2SOCH3 | H | H | 3-Cl | 2-CH3 | H | C2F5 | C2F5 | H | |
| 709 | C(CH3)2CH2SO2CH3 | H | H | 3-Cl | 2-CH3 | H | C2F5 | C2F5 | H | |
| 710 | CH(CH3)CH2SCH3(S) | H | H | 3-Cl | 2-CH3 | H | C3F7-n | H | H | |
| 711 | C(CH3)2CH2SCH3 | H | H | 3-Cl | 2-CH3 | H | C3F7-n | H | H | |
| 712 | CH(CH3)CH2SCH3(S) | H | H | 3-Cl | 2-CH3 | H | C3F7-n | C3F7-n | H | |
| 713 | CH(CH3)CH2SCH3(S) | H | H | 3-Cl | 2-CH3 | H | C4F9-n | H | H | |
| 714 | CH(CH3)CH2SCH3(S) | H | H | 3-Cl | 2-CH3 | H | C4F9-n | C4F9-n | H | |
| 715 | CH(CH3)CH2SCH3(S) | H | H | 3-Cl | 2-CH3 | H | SCF3 | SCF3 | H | |
| 716 | CH(CH3)CH2SCH3(S) | H | H | 3-Cl | 2-CH3 | H | Cl | Cl | H | |
| 717 | CH(CH3)CH2SCH3(S) | H | H | 3-Br | 2-CH3 | H | CF3 | CF3 | H | |
| 718 | CH(CH3)CH2SCH3(S) | H | H | 3-Br | 2-CH3 | H | C2F5 | C2F5 | H | |
| 719 | C(CH3)2CH2SCH3 | H | H | 3-I | 2-CH3 | H | CF3 | CF3 | H | |
| 720 | C(CH3)2CH2SCH3 | H | H | 3-I | 2-CH3 | H | C2F5 | C2F5 | H | |
| 721 | CH(CH3)CH2SCH3 | H | H | 3-F | 2-CH3 | H | CF3 | CF3 | H | |
| 722 | CH(CH3)CH2SCH3 | H | H | 3-F | 2-CH3 | H | C2F5 | C2F5 | H | |
| 723 | CH(CH3)CH2SCH3 | H | H | 3-NO2 | 2-CH3 | H | CF3 | CF3 | H | |
| 724 | CH(CH3)CH2SCH3 | H | H | 3-NO2 | 2-CH3 | H | C2F5 | C2F5 | H | |
| 725 | CH(CH3)CH2SCH3 | H | H | 3-MeSO2O | 2-CH3 | H | C2F5 | C2F5 | H | |
| 726 | CH(CH3)CH2SCH3 | H | H | 3-MeS | 2-CH3 | H | C2F5 | C2F5 | H | |
| 727 | CH(CH3)CH2SCH3 | H | H | 3-MeSO | 2-CH3 | H | C2F5 | C2F5 | H | |
| 728 | CH(CH3)CH2SCH3 | H | H | 3-MeSO2 | 2-CH3 | H | C2F5 | C2F5 | H | |
| 729 | CH(CH3)CH2SCH3 | CH3 | H | 3-Cl | 2-CH3 | H | CF3 | CF3 | H | |
| 730 | CH(CH3)CH2SCH3 | CH3 | H | 3-Cl | 2-CH3 | H | C2F5 | C2F5 | H | |
| 731 | CH(CH3)CH2SCH3 | CH3 | H | 3-Br | 2-CH3 | H | CF3 | CF3 | H | |
| 732 | CH(CH3)CH2SCH3 | CH3 | H | 3-Br | 2-CH3 | H | C2F5 | C2F5 | H | |
| 733 | CH(CH3)CH2SCH3 | CH3 | H | 3-I | 2-CH3 | H | C2F5 | C2F5 | H | |
| 734 | CH(CH3)CH2SCH3 | CF3 | H | 3-Cl | 2-CH3 | H | C2F5 | C2F5 | H | |
| 735 | CH(CH3)CH2SO2CH3(S) | CF3 | H | 3-Br | 2-CH3 | H | C2F5 | C2F5 | H | |
| 736 | CH(CH3)CH2SCH3 | CF3 | H | 3-I | 2-CH3 | H | C2F5 | C2F5 | H | |
| 737 | CH(CH3)CH2SCH3 | H | OH | 3-Cl | 2-CH3 | H | C2F5 | C2F5 | H | |
| 738 | CH(CH3)CH2SCH3 | H | OH | 3-Br | 2-CH3 | H | C2F5 | C2F5 | H | |
| 739 | CH(CH3)CH2SCH3 | H | OH | 3-I | 2-CH3 | H | C2F5 | C2F5 | H | |
| 740 | CH(CH3)CH2SCH3 | CF3 | OH | 3-Cl | 2-CH3 | H | CF3 | CF3 | H | |
| 741 | CH(CH3)CH2SCH3 | CF3 | OH | 3-Cl | 2-CH3 | H | C2F5 | C2F5 | H | |
| 742 | CH(CH3)CH2SCH3 | CF3 | OH | 3-I | 2-CH3 | H | C2F5 | C2F5 | H | |
| 743 | CH(CH3)CH2SCH3 | H | H | 3-Cl | 2-Cl | H | C2F5 | C2F5 | H | |

TABLE 7

| | R1 | R2 | R3 | X | Y | Z1 | Z3 | Z4 | Z5 | mp |
|---|---|---|---|---|---|---|---|---|---|---|
| 744 | CH(CH3)CH2SCH3 | H | H | 3-Cl | 2-CH3 | H | CF3 | H | H | |
| 745 | CH(CH3)CH2SOCH3 | H | H | 3-Cl | 2-CH3 | H | CF3 | H | H | |
| 746 | CH(CH3)CH2SO2CH3 | H | H | 3-Cl | 2-CH3 | H | CF3 | H | H | |
| 747 | CH(CH3)CH2SCH3(S) | H | H | 3-Cl | 2-CH3 | H | C2F5 | H | H | |
| 748 | CH(CH3)CH2SOCH3(S) | H | H | 3-Cl | 2-CH3 | H | C2F5 | H | H | |
| 749 | CH(CH3)CH2SO2CH3(S) | H | H | 3-Cl | 2-CH3 | H | C2F5 | H | H | |
| 750 | CH(CH3)CH2SCH3(S) | H | H | 3-Cl | 2-CH3 | H | C2F5 | C2F5 | H | |
| 751 | CH(CH3)CH2SOCH3(S) | H | H | 3-Cl | 2-CH3 | H | C2F5 | C2F5 | H | |
| 752 | CH(CH3)CH2SO2CH3(S) | H | H | 3-Cl | 2-CH3 | H | C2F5 | C2F5 | H | |
| 753 | C(CH3)2CH2SCH3 | H | H | 3-Cl | 2-CH3 | H | C2F5 | C2F5 | H | |
| 754 | C(CH3)2CH2SOCH3 | H | H | 3-Cl | 2-CH3 | H | C2F5 | C2F5 | H | |
| 755 | C(CH3)2CH2SO2CH3 | H | H | 3-Cl | 2-CH3 | H | C2F5 | C2F5 | H | |
| 756 | CH(CH3)CH2SCH3 | H | H | 3-Cl | 2-CH3 | H | C3F7-n | H | H | |
| 757 | CH(CH3)CH2SOCH3(S) | H | H | 3-Cl | 2-CH3 | H | C3F7-n | H | H | |
| 758 | CH(CH3)CH2SO2CH3(S) | H | H | 3-Cl | 2-CH3 | H | C3F7-n | H | H | |
| 759 | CH(CH3)CH2SCH3 | H | H | 3-Cl | 2-CH3 | H | C4F9-n | H | H | |
| 760 | CH(CH3)CH2SCH3 | H | H | 3-Cl | 2-CH3 | H | SCF3 | H | H | |
| 761 | CH(CH3)CH2SCH3 | H | H | 3-Cl | 2-CH3 | H | SC2F5 | H | H | |
| 762 | CH(CH3)CH2SCH3 | H | H | 3-Br | 2-CH3 | H | C2F5 | C2F5 | H | |
| 763 | CH(CH3)CH2SCH3 | H | H | 3-I | 2-CH3 | H | C2F5 | C2F5 | H | |
| 764 | CH(CH3)CH2SCH3 | H | H | 3-F | 2-CH3 | H | C2F5 | C2F5 | H | |
| 765 | CH(CH3)CH2SCH3 | H | H | 3-NO2 | 2-CH3 | H | C2F5 | C2F5 | H | |
| 766 | CH(CH3)CH2SCH3 | H | H | 3-MeSO2O | 2-CH3 | H | C2F5 | C2F5 | H | |
| 767 | CH(CH3)CH2SCH3 | CH3 | H | 3-Cl | 2-CH3 | H | C2F5 | H | H | |
| 768 | CH(CH3)CH2SCH3 | CH3 | H | 3-Cl | 2-CH3 | H | C2F5 | C2F5 | H | |
| 769 | CH(CH3)CH2SCH3 | CH3 | H | 3-Cl | 2-CH3 | H | C3F7-n | H | H | |
| 770 | CH(CH3)CH2SCH3 | CH3 | H | 3-Br | 2-CH3 | H | C2F5 | C2F5 | H | |
| 771 | CH(CH3)CH2SCH3 | CH3 | H | 3-I | 2-CH3 | H | C2F5 | C2F5 | H | |
| 772 | CH(CH3)CH2SCH3 | CF3 | H | 3-Cl | 2-CH3 | H | C2F5 | C2F5 | H | |
| 773 | CH(CH3)CH2SCH3 | CF3 | H | 3-Br | 2-CH3 | H | C2F5 | C2F5 | H | |
| 774 | CH(CH3)CH2SCH3 | CF3 | H | 3-I | 2-CH3 | H | C2F5 | C2F5 | H | |
| 775 | CH(CH3)CH2SCH3(S) | H | OH | 3-Cl | 2-CH3 | H | C2F5 | C2F5 | H | |
| 776 | CH(CH3)CH2SCH3(S) | CF3 | OH | 3-Cl | 2-CH3 | H | C2F5 | C2F5 | H | |
| 777 | CH(CH3)CH2SCH3(S) | CF3 | OH | 3-I | 2-CH3 | H | C2F5 | C2F5 | H | |
| 778 | CH(CH3)CH2SCH3(S) | H | H | 3-Cl | 2-Cl | H | C2F5 | C2F5 | H | |

TABLE 8

| | R1 | R2 | R3 | X | Y | Z2 | Z3 | Z4 | Z5 | mp |
|---|---|---|---|---|---|---|---|---|---|---|
| 779 | CH(CH3)CH2SCH3 | H | H | 3-Cl | 2-CH3 | CF3 | H | H | H | |
| 780 | CH(CH3)CH2SOCH3 | H | H | 3-Cl | 2-CH3 | CF3 | H | H | H | |
| 781 | CH(CH3)CH2SO2CH3 | H | H | 3-Cl | 2-CH3 | CF3 | H | H | H | |
| 782 | CH(CH3)CH2SCH3(S) | H | H | 3-Cl | 2-CH3 | C2F5 | H | H | H | |
| 783 | CH(CH3)CH2SOCH3(S) | H | H | 3-Cl | 2-CH3 | C2F5 | H | H | H | |

TABLE 8-continued

| | R1 | R2 | R3 | X | Y | Z2 | Z3 | Z4 | Z5 | mp |
|---|---|---|---|---|---|---|---|---|---|---|
| 784 | CH(CH3)CH2SO2CH3(S) | H | H | 3-Cl | 2-CH3 | C2F5 | H | H | H | |
| 785 | CH(CH3)CH2SCH3(S) | H | H | 3-Cl | 2-CH3 | C2F5 | C2F5 | H | H | |
| 786 | CH(CH3)CH2SCH3(S) | H | H | 3-Cl | 2-CH3 | C3F7-n | H | H | H | |
| 787 | CH(CH3)CH2SCH3(S) | H | H | 3-Cl | 2-CH3 | H | C3F7-i | H | H | |
| 788 | CH(CH3)CH2SCH3 | H | H | 3-Cl | 2-CH3 | SCF3 | H | H | H | |
| 789 | CH(CH3)CH2SCH3 | H | H | 3-Cl | 2-CH3 | SC2F5 | H | H | H | |
| 790 | CH(CH3)CH2SCH3(S) | H | H | 3-Br | 2-CH3 | C2F5 | H | H | H | |
| 791 | CH(CH3)CH2SCH3(S) | H | H | 3-Br | 2-CH3 | C3F7-n | H | H | H | |
| 792 | CH(CH3)CH2SCH3(S) | H | H | 3-I | 2-CH3 | C2F5 | H | H | H | |
| 793 | CH(CH3)CH2SCH3(S) | H | H | 3-I | 2-CH3 | C2F5 | C2F5 | H | H | |
| 794 | CH(CH3)CH2SCH3 | H | H | 3-I | 2-CH3 | C3F7-n | H | H | H | |
| 795 | CH(CH3)CH2SCH3 | H | H | 3-I | 2-CH3 | C4F9-n | H | H | H | |
| 796 | CH(CH3)CH2SCH3 | H | H | 3-F | 2-CH3 | C3F7-n | H | H | H | |
| 797 | CH(CH3)CH2SCH3 | H | H | 3-NO2 | 2-CH3 | C3F7-n | H | H | H | |
| 798 | CH(CH3)CH2SCH3 | H | H | 3-MeSO2 | 2-CH3 | C3F7-n | H | H | H | |
| 799 | CH(CH3)CH2SCH3 | CH3 | H | 3-Cl | 2-CH3 | C2F5 | H | H | H | |
| 800 | CH(CH3)CH2SCH3 | CH3 | H | 3-Cl | 2-CH3 | C3F7-n | H | H | H | |
| 801 | CH(CH3)CH2SCH3 | CH3 | H | 3-Cl | 2-CH3 | H | C3F7-i | H | H | |
| 802 | CH(CH3)CH2SCH3 | CH3 | H | 3-Br | 2-CH3 | C2F5 | H | H | H | |
| 803 | CH(CH3)CH2SCH3 | CH3 | H | 3-Br | 2-CH3 | C3F7-n | H | H | H | |
| 804 | CH(CH3)CH2SOCH3(S) | CH3 | H | 3-I | 2-CH3 | C2F5 | H | H | H | |
| 805 | CH(CH3)CH2SCH3(S) | CH3 | H | 3-I | 2-CH3 | C3F7-n | H | H | H | |
| 806 | CH(CH3)CH2SCH3(S) | CF3 | H | 3-Cl | 2-CH3 | C2F5 | H | H | H | |
| 807 | CH(CH3)CH2SCH3(S) | CF3 | H | 3-Cl | 2-CH3 | C3F7-n | H | H | H | |
| 808 | CH(CH3)CH2SCH3(S) | CF3 | H | 3-Cl | 2-CH3 | H | C3F7-i | H | H | |
| 809 | CH(CH3)CH2SO2CH3(S) | CF3 | H | 3-Br | 2-CH3 | C2F5 | H | H | H | |
| 810 | CH(CH3)CH2SCH3(S) | CF3 | H | 3-Br | 2-CH3 | C3F7-n | H | H | H | |
| 811 | CH(CH3)CH2SCH3(S) | CF3 | H | 3-I | 2-CH3 | C2F5 | H | H | H | |
| 812 | CH(CH3)CH2SCH3(S) | CF3 | OH | 3-Cl | 2-CH3 | C2F5 | H | H | H | |
| 813 | CH(CH3)CH2SCH3(S) | CF3 | OH | 3-Cl | 2-CH3 | C3F7-n | H | H | H | |
| 814 | CH(CH3)CH2SCH3(S) | H | H | 3-Cl | 2-Cl | C3F7-n | H | H | H | |

Synthesis Example 6 (Intermediate)

4-(3,5-Bis-trifluoromethyl-benzyl)-2-methyl-nitrobenzene

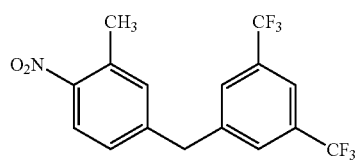

A solution of 3-methyl-4-nitrobenzyl chloride (0.27 g), 3,5-bis-(trifluoromethyl)phenylboronic acid (0.45 g), tetrakis (triphenylphosfine)palladium (0.1 g) and sodium carbonate (0.48 g) in water (2 ml) and 1,2-dimethoxyethane (10 ml) was stirred under an argon atmosphere at 85° C. for 2 hours. After cooling, the reaction solution was diluted with ethyl acetate and further stirred for 10 minutes by adding water thereto. After washing the organic layer with a saturated salt solution, it was dried over anhydrous magnesium sulfate. The solution was distilled off under reduced pressure and the resultant residue was purified by silica gel column chromatography to obtain 4-(3,5-bis-trifluoromethyl-benzyl)-2-methyl-nitrobenzene (0.44 g).

$^1$H-NMR (CDCl$_3$) δ: 2.61 (3H, s), 4.13 (2H, s), 7.14-7.17 (2H, m), 7.62 (2H, s), 7.78 (1H, s), 7.93-7.99 (1H, m)

Synthesis Example 7 (Intermediate)

4-(3,5-Bis-trifluoromethyl-benzyl)-2-methylaniline

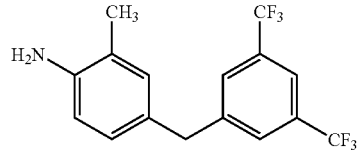

A solution of 20% titanium trichloride (8.4 g) was added to a mixture of 4-(3,5-bis-trifluoromethyl-benzyl)-2-methyl-nitrobenzene (0.44 g), ammonium acetate (9.3 g), acetone (20 ml) and water (10 ml) at room temperature and stirred for 12 hours. After the reaction, the reaction solution was extracted with ethyl acetate and washed with a saturated sodium bicarbonate solution and a saturated salt solution and then dried over anhydrous magnesium sulfate. After distilling the solvent off, the resultant residue was purified by silica gel column chromatography to obtain 4-(3,5-bis-trifluoromethyl-benzyl)-2-methylaniline (0.22 g).

$^1$H-NMR (CDCl$_3$) δ: 2.14 (3H, s), 3.53 (2H, br s), 3.98 (2H, s), 6.52-6.63 (1H, m), 6.81-6.86 (1H, m), 7.61 (2H, s), 7.69 (1H, s)

Synthesis Example 8 (Material)

Methyl 3,5-bis-n-perfluorobutylbenzoate

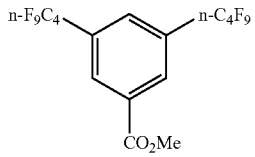

Methyl 3,5-diiodobenzoate (1 g), copper powder (1.6 g), n-perfluorobutyl iodide (2.7 g) and DMSO (10 ml) were heated and stirred at 120° C. for 3 hours. After cooling, ethyl acetate and water were added to the reaction solution and stirred, and after filtering out the insoluble matter with a celite, the organic layer was washed with a saturated salt solution. After drying over anhydrous magnesium sulfate, the solvent was distilled off and the residue was purified by silica gel column chromatography to obtain methyl 3,5-bis-n-perfluorobutylbenzoate (0.9 g).

$^1$H-NMR (CDCl$_3$) δ: 3.99 (3H, s), 7.96 (1H, s), 8.47 (2H, s)

Synthesis Example 9 (Material)

3,5-Bis-n-perfluorobutylbenzylalcohol

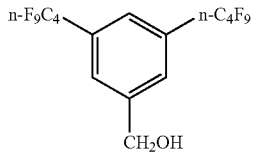

A solution of 5-bis-n-perfluorobutylbenzoate (0.9 g) in THF (5 ml) was slowly added dropwise to a solution of lithium aluminum hydride (0.75 g) in THF (10 ml) in an ice bath. After stirring for 1 hour, the reaction solution was diluted with ethyl ether, to which a saturated salt solution (1 ml) was added slowly and stirred for 30 minutes. After separating and removing the insoluble matter by filtration, the result was dried over anhydrous magnesium sulfate. After distilling off the solvent under reduced pressure, the residue was purified by silica gel column chromatography to obtain 3,5-bis-n-perfluorobutylbenzylalcohol (0.85 g).

$^1$H-NMR (CDCl$_3$) δ: 4.90 (2H, d), 7.72 (1H, s), 7.83 (2H, s)

Synthesis Example 10 (Material)

3,5-Bis-n-perfluorobutylbenzyl bromide

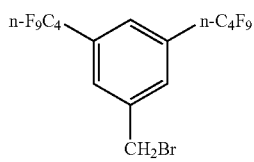

Carbon tetrabromide (0.62 g) and triphenylphosphine (0.49 g) were added to a solution of 3,5-bis-n-perfluorobutylbenzyl alcohol (0.85 g) in methylene chloride (10 ml) and stirred for 10 hours at room temperature. After distilling off the solvent under reduced pressure, the residue was purified by silica gel column chromatography to obtain 3,5-bis-n-perfluorobutylbenzyl bromide (0.4 g).

$^1$H-NMR (CDCl$_3$) δ: 4.56 (2H, s), 7.74 (1H, s), 7.84 (2H, s)

Synthesis Example 11 (Intermediate)

Tert-butyl[2-methyl-4-(4,4,5,5-tetramethyl-1,3,2-dioxaboran-2-yl)-phenyl]-carbamate

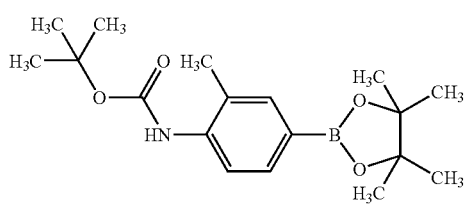

A solution of tert-butyl (4-iodo-2-methylphenyl)carbamate (1.39 g), pinacolborane (0.8 g), triethylamine (1.27 g), 1,1'-bis-(diphenylphosphino)ferrocenepalladium (II) chloride (0.09 g) in dioxane (20 ml) was heated and stirred in an argon atmosphere at 80° C. for 4 hours. After cooling, water was added and stirred followed by extraction with ethyl acetate and washing with a saturated salt solution. After drying over anhydrous magnesium sulfate, the solvent was distilled off under reduced pressure and the residue was purified by silica gel column chromatography to obtain tert-butyl[2-methyl-4-(4,4,5,5-tetramethyl-1,3,2-dioxaboran-2-yl)-phenyl]-carbamate (0.95 g).

$^1$H-NMR (CDCl$_3$) δ: 1.33 (13H, s), 1.55 (9H, s), 2.24 (3H, s), 6.38 (1H, br s), 7.58 (1H, s), 7.64 (1H, d), 7.94 (1H, d).

Synthesis Example 12 (Intermediate)

Tert-butyl[4-(3,5-bis-n-perfluorobutylbenzyl)-2-methylphenyl]-carbamate

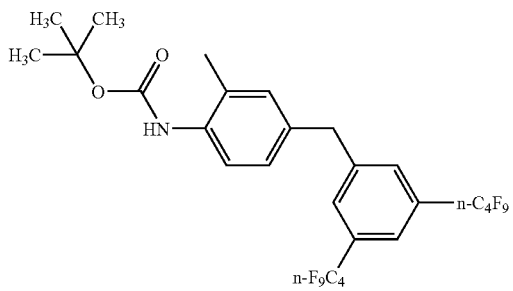

A solution of 3,5-bis-n-perfluorobutylbenzyl bromide (0.40 g), tert-butyl [2-methyl-4-(4,4,5,5-tetramethyl-1,3,2-dioxaboran-2-yl)-phenyl]-carbamate (0.22 g), tetrakis(triphenylphosphine)-palladium (0.05 g) and sodium carbonate (0.22 g) in water (2 ml) and 1,2-dimethoxyethane (10 ml) was heated and stirred under an argon atmosphere at 85° C. for 2 hours. After cooling, the reaction solution was diluted with ethyl acetate and, by adding water, stirred for 10 minutes. The organic layer was dried over anhydrous magnesium sulfate after washing with a saturated salt solution. The solvent was distilled off under reduced pressure and the resultant residue was purified by silica gel column chromatography to obtain tert-butyl[4-(3.5-bis-n-perfluorobutylbenzyl)-2-methylphenyl]-carbamate (0.22 g).

$^1$H-NMR (CDCl$_3$) δ: 1.58 (9H, s), 2.29 (3H, s), 4.02 (2H, s), 6.25 (1H, br s), 6.91 (1H, s), 6.97-7.00 (1H, m), 7.61-7.64 (3H, m), 7.77-7.80 (1H, m)

Synthesis Example 13 (Intermediate)

4-(3,5-Bis-n-perfluorobutylbenzyl)-2-methylaniline

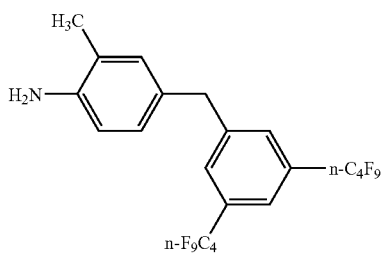

Trifluoroacetic acid (0.5 g) was added to a solution of tert-butyl[4-(3,5-bis-n-perfluorobutylbenzyl)-2-methylphenyl]-carbamate (0.22 g) in methylene chloride (5 ml) and stirred at room temperature for 3 hours. After the reaction, the solvent was distilled off under reduced pressure followed by dissolving the residue into ethyl acetate, and washed with a saturated sodium bicarbonate solution and a saturated salt solution. After the organic layer was dried over anhydrous magnesium sulfate, the solvent was distilled off under reduced pressure to obtain 4-(3,5-bis-n-perfluorobutylbenzyl)-2-methylaniline (0.15 g).

$^1$H-NMR (CDCl$_3$) δ: 2.11 (3H, s), 3.54 (2H, br s), 3.98 (2H, s), 6.59-6.69 (1H, m), 6.77-6.80 (2H, m), 7.58-7.73 (3H, m)

Synthesis Example 14 (Material)

Methyl 3,4-bis-perfluoroethylbenzoate

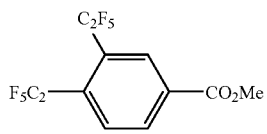

A solution of methyl 3,4-diiodobenzoate (1 g), perfluoroethyltrimethylsilane (1.98 g), cuprous iodide (1.96 g) and potassium fluoride (0.33 g) in DMF (10 ml) was heated and stirred in a sealed tube at 100° C. for 3 hours under an argon atmosphere. After cooling, the reaction mixture was diluted with ethyl acetate, then the insoluble matter was filtered out with a celite and the organic layer was washed with a saturated salt solution. After drying over anhydrous magnesium sulfate, the solvent was distilled off and the residue was purified by silica gel column chromatography to obtain methyl 3,4-bis-perfluoroethylbenzoate (0.55 g).

$^1$H-NMR (CDCl$_3$) δ: 4.01 (3H, s), 7.90 (1H, d), 8.37 (1H, d), 8.46 (1H, s)

Synthesis Example 15 (Material)

Methyl 6-n-perfluoropropylnicotinate

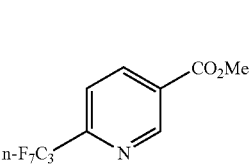

Methyl 6-chloronicotinate (3 g), copper powder (2.2 g), n-perfluoropropyl iodide (9.0 g) and DMSO (10 ml) were heated and stirred at 120° C. for 3 hours. After cooling, the reaction solution was stirred by adding ethyl acetate and water, then the insoluble matter was separated by filtration with a celite and the organic layer was washed with a saturated salt solution. After drying over anhydrous magnesium sulfate, the solvent was distilled off and the residue was purified by silica gel column chromatography to obtain methyl 6-n-perfluoropropylnicotinate (4.2 g).

$^1$H-NMR (CDCl$_3$) δ: 3.94-4.06 (3H, m), 7.80 (1H, d), 8.50 (1H, d), 9.34 (1H, d)

Synthesis Example 16 (Intermediate)

3',5'-Bis-trifluoromethyl-3-methyl-4-nitrobenzophenone

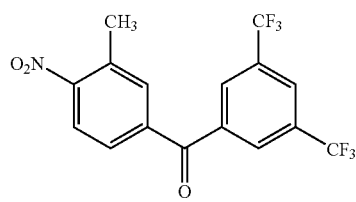

Chromic oxide (IV) (0.41 g) was added to a solution of 4-(3,5-bis-trifluoromethyl-benzyl)-2-methylnitrobenzene (0.3 g) in acetic acid (10 ml) and stirred at room temperature for 1 hour. After the reaction, the reaction solution was extracted with ethyl acetate and washed with water, a saturated sodium bicarbonate solution and a saturated salt solution. After drying over anhydrous magnesium sulfate, the solvent was distilled off and the residue was purified by silica gel column chromatography to obtain 3',5'-bis-trifluoromethyl-3-methyl-4-nitrobenzophenone (0.3 g).

$^1$H-NMR (CDCl$_3$) δ: 2.68 (3H, s), 7.68-7.71 (1H, m), 7.76-7.80 (1H, m), 8.08 (1H, d), 8.15 (1H, s), 8.23 (2H, s)

Synthesis Example 17 (Intermediate)

(3,5-Bis-trifluoromethylphenyl)(3-methyl-4-nitrophenyl)methanol

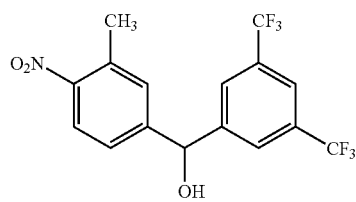

Sodium borohydride (0.12 g) was added to a solution of 3',5'-bis-trifluoromethyl-3-methyl-4-nitrobenzophenone (2.2 g) in methanol (10 ml) in an ice bath. After stirring at room temperature for 1 hour, and diluting with ethyl acetate, it was washed with water and a saturated salt solution. After drying over anhydrous magnesium sulfate, the solvent was distilled off and the residue was purified by silica gel column chromatography to obtain (3,5-bis-trifluoromethylphenyl)(3-methyl-4-nitrophenyl)methanol (1.6 g).

$^1$H-NMR (CDCl$_3$) δ: 2.60 (3H, s), 5.98 (1H, s), 7.34-7.37 (2H, m), 7.83-7.84 (3H, m), 7.99 (1H, d)

Synthesis Example 18 (Intermediate)

1-(3,5-Bis-trifluoromethylphenyl)-2,2,2-trifluoro-1-(3-methyl-4-nitrophenyl)ethanol

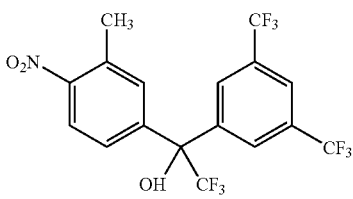

A solution of 1M tetrabutylammonium fluoride in tetrahydrofuran (0.2 ml) was added to a solution of 3',5'-bis-trifluoromethyl-3-methyl-4-nitrobenzophenone (1.4 g) and trifluoromethyltrimethyl-silane (1.0 g) in tetrahydrofuran (20 ml) in an ice bath and stirred at room temperature for 8 hours. The reaction solution was diluted with ethyl acetate and washed with water and a saturated salt solution. After drying over anhydrous magnesium sulfate, the solvent was distilled off. The residue was dissolved in tetrahydrofuran (20 ml) and, by adding 2N hydrochloric acid (2 ml), stirred at room temperature for 30 minutes. After diluting with ethyl acetate and washing with water and a saturated salt solution and after drying over anhydrous magnesium sulfate, the solvent was distilled off. Then the residue was purified by silica gel column chromatography to obtain 1-(3,5-bis-trifluoromethylphenyl)-2,2,2-trifluoro-1-(3-methyl-4-nitrophenyl)ethanol (0.8 g).

$^1$H-NMR (CDCl$_3$) δ: 2.66 (3H, s), 7.68-7.71 (1H, m), 7.78-7.79 (1H, m), 8.08 (1H, d), 8.14 (1H, s), 8.23 (2H, s)

Synthesis Example 19 (Intermediate)

1-(3,5-Bis-trifluororomethylphenyl)-2,2,2-trifluoro-1-(3-methyl-4-nitrophenyl)ethyl methanesulfonate

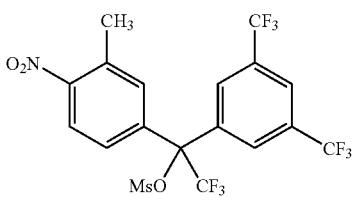

Methanesulfonyl chloride (0.11 g) was added dropwise to a solution of 1-(3,5-bis-trifluoromethylphenyl)-2,2,2-trifluoro-1-(3-methyl-4-nitrophenyl)ethanol (0.4 g) and triethylamine (0.11 g) in methylene chloride (10 ml) in an ice bath and stirred at room temperature for 1 hour. After the reaction and washing with water, a dilute hydrochloric acid and a saturated salt solution, the organic layer was dried over anhydrous magnesium sulfate. Under reduced pressure, the solvent was distilled off and the residue was purified by silica gel column chromatography to obtain 1-(3,5-bis-trifluroromethylphenyl)-2,2,2-trifluoro-1-(3-methyl-4-nitrophenyl)ethyl methanesulfonate (0.46 g).

$^1$H-NMR (CDCl$_3$) δ: 2.62 (3H, s), 3.19 (3H, s), 3.73 (1H, s), 7.42-7.46 (2H, m), 7.88 (2H, s), 8.00-8.03 (2H, m)

Synthesis Example 20 (Intermediate)

1-(3,5-Bis-trifluoromethylphenyl)-2,2,2-trifluoro-1-(3-methyl-4-nitrophenyl)ethane

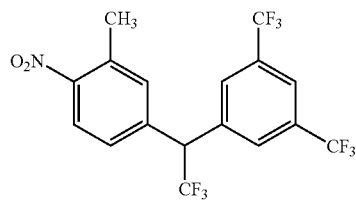

A solution of 1-(3,5-bis-trifluoromethylphenyl)-2,2,2-trifluoro-1-(3-methyl-4-nitrophenyl)ethyl methanesulfonate (0.5 g) in tetrahydrofuran (5 ml) was slowly added dropwise to a solution of lithium aluminium hydride (0.04 g) in tetrahydrofuran (10 ml) in an ice bath. After stirring for 30 minutes, the reaction solution was diluted with ethyl ether, and then stirred for 30 minutes by slowly adding a saturated salt solution (1 ml). After the insoluble matter was separated by filtration, the solution was dried over anhydrous magnesium sulfate. The solvent was distilled off under reduced pressure and the residue was purified by silica gel column chromatography to obtain 1-(3,5-bis-trifluoromethylphenyl)-2,2,2-trifluoro-1-(3-methyl-4-nitrophenyl)ethane (0.11 g).

$^1$H-NMR (CDCl$_3$) δ: 2.61 (3H, s), 4.89 (1H, q), 7.34-7.36 (2H, m), 7.80 (2H, s), 7.90 (1H, s), 8.02 (1H, d)

Biological Test Example 1

*Spodoptera litura* Larva

Preparation of Test Solution:
Solvent: 3 parts by weight of dimethylformamide
Emulsifier: 1 part by weight of polyoxyethylene alkylphenyl ether To prepare a suitable formulation of the active compound, 1 part by weight of the active compound was mixed with the above solvent containing the above emulsifier, and the mixture was diluted with water to a predetermined concentration.

Test Method:
Sweet potato leaves were dipped in the test solution which was water-diluted to the predetermined concentration, then air-dried and put in a Petri dish of 9 cm in diameter, in which ten 3rd instar larvae of *Spodoptera litura* were released, then kept at a constant 25° C. Additional sweet potato leaves were added 2 and 4 days later, and the mortality was determined by counting the number of dead insects 7 days later.

The present test looked at the average results of 2 Petri dishes per group.

Biological Test Example 2

*Cnaphalocrocis medinalis* Larva

Test Method:
A test solution, water-diluted to the predetermined concentration of the active compound, prepared in the same manner as in Biological Test Example 1 above was applied to pot transplanted rice (Tamanishiki variety) at the rate of 50 ml per pot. After air-drying the treated rice, the foliage was cut in lengths of 4-5 cm and put in a Petri dish of 9 cm in diameter filled with 2 ml of water on a filter paper. Five 2nd instar larvae of *Cnaphalocrocis medinalis* were released in the dish and kept at a constant 25° C. The remaining similarly cut rice foliage (⅓ each) was added thereto 2 and 4 days later, and the mortality was determined by counting the number of dead insects 7 days later. The present test looked at the average results of 2 Petri dishes per group.

Test ResultS:
In the above Biological Test Examples 1 and 2, at the concentration of 20 ppm, the insect mortality was 100% with Compound Nos. 19, 20, 21, 56, 57, 58, 65, 66, 67, 88, 89, 90, 98, 112, 149, 212, 345, 583, 584 and 635 as representative examples of the compounds according to the present invention.

Biological Test Example 3

*Myzus persicae* Resistant to Organophosphorous and Carbamate Insecticides

Test Method:
About 30 captive bred organophosphorous- and carbamate-resistant *Myzus persicae* per seedling were inoculated to eggplant seedlings planted in vinyl pots of 6 cm in diameter, to which the active compound solution prepared as above and water-diluted to the predetermined concentration was sufficiently applied using a spray gun one day after the inoculation, and left at 28° C. in a greenhouse. The insect mortality was determined 7 days after the application. The test was repeated twice.

Test Results:
At the concentration of 100 ppm, the insect mortality was 100% with Compound Nos. 19, 152 and 635 as representative examples of the compounds according to the present invention.

Formulation Example 1 (Granule)

The granular formulation was prepared by adding 25 parts by weight of water to the mixture of 10 parts by weight of Compound No. 19 of the present invention, 30 parts by weight of bentonite (montmorillonite), 58 parts by weight of talc and 2 parts by weight of lignosulfonate, and sufficiently kneaded followed by granulating into 10-40 mesh granules using an extruding granulator, and drying at 40-50° C.

Formulation Example 2 (Granule)

95 Parts by weight of clay mineral particles having a particle size distribution of 0.2-2 mm were placed in a revolving blender, which were then sprayed with 5 parts by weight of Compound No. 20 of the present invention together with a liquid diluent during the rotation for uniform moistening followed by drying at 40-50° C. to give the granular formulation.

Formulation Example 3 (Emulsifiable Concentrate)

30 Parts by weight of Compound No. 56 of the present invention, 55 parts by weight of xylene, 8 parts by weight of polyoxyethylenealkylphenylether and 7 parts by weight of calcium alkylbenzenesulfonic acid were mixed and stirred to give the emulsifiable concentrate.

Formulation Example 4 (Wettable Powder)

15 Parts by weight of Compound No. 65 of the present invention, 80 parts by weight of the mixture of white carbon (hydroscopic amorphous silicon oxide fine powder) and clay powder (1:5), 2 parts of sodium alkylbenzenesulfonic acid and 3 parts by weight of sodium alkylnaphthalenesulfonic acid formalin condensate were ground and mixed to give the wettable powder.

Formulation Example 5 (Wettable Granule)

To prepare the wettable granule formulation, 20 parts by weight of Compound No. 112 of the present invention, 30 parts by weight of sodium lignosulfonate, 15 parts by weight of bentonite and 35 parts by weight of calcined diatomaceous earth powder were mixed well, and then water was added thereto followed by the extrusion using a 0.3 mm mesh screen and drying the result.

INDUSTRIAL APPLICABILITY

As shown in the Examples above, the novel benzanilides of the present invention have superior insecticidal activity as effective insecticides.

The invention claimed is:
1. A benzanilide of the formula:

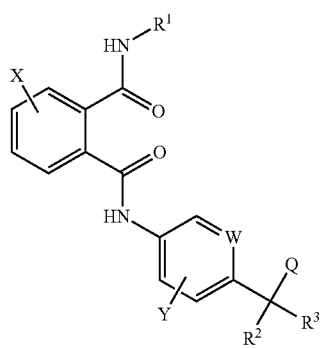

in which
X represents hydrogen, halogen, nitro, $C_{1-6}$ alkylthio, $C_{1-6}$ alkylsulfinyl, $C_{1-6}$ alkylsulfonyl or $C_{1-6}$ alkylsulfonyloxy;
Y represents halogen or $C_{1-6}$ alkyl;
$R^1$ represents $C_{1-6}$ alkyl, $C_{1-6}$ alkylthio-$C_{1-6}$ alkyl, $C_{1-6}$ alkylsulfinyl-$C_{1-6}$ alkyl or $C_{1-6}$ alkylsulfonyl-$C_{1-6}$ alkyl;
$R^2$ represents hydrogen, $C_{1-6}$ alkyl or $C_{1-6}$ haloalkyl;
$R^3$ represents hydrogen;
W represents CH or N; and
Q represents substituted phenyl or substituted pyridyl wherein the substituent is at least one $C_{1-6}$ haloalkyl.
2. A compound according to claim 1 in which
X is halogen, nitro, $C_{1-4}$ alkylthio, $C_{1-4}$ alkylsulfinyl, $C_{1-4}$ alkylsulfonyl, or $C_{1-4}$ alkylsulfonyloxy;
Y is halogen or $C_{1-4}$ alkyl;
$R^1$ is $C_{1-4}$ alkyl, $C_{1-4}$ alkylthio-$C_{1-4}$ alkyl, $C_{1-4}$ alkylsulfinyl-$C_{1-4}$ alkyl or $C_{1-4}$ alkylsulfonyl-$C_{1-4}$ alkyl;
$R^2$ is hydrogen, $C_{1-4}$ alkyl or $C_{1-4}$ haloalkyl;
$R^3$ is hydrogen;
W is CH or N; and
Q is substituted phenyl or substituted pyridyl wherein the substituent is at least one $C_{1-4}$ haloalkyl.
3. Method for the preparation of compounds of the formula (I) according to claim 1, comprising at least one of the following reaction schemes:

(a) reacting at least one compound of formula (II):

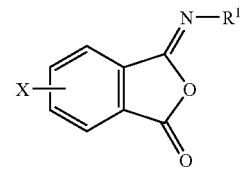

with at least one compound of formula (III):

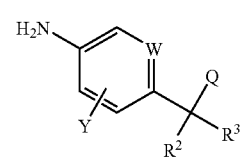

in the presence of at least one inert solvent, and if appropriate, in the presence of an acid catalyst;

(b) reacting at least one compound compounds of formula (IV):

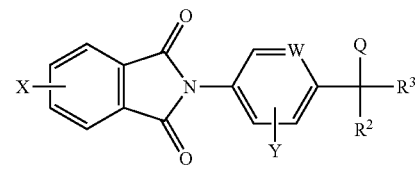

with at least one compound of formula (V):

$$R^1-NH_2 \quad (V)$$

in the presence of at least one inert solvent, and if appropriate, in the presence of an acid catalyst;

(c) reacting at least one compound of formula (VI):

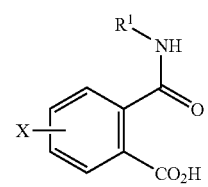

with at least one compound said formula (III), in the presence of at least one inert solvent, and if appropriate, in the presence of an acid catalyst;

(d) reacting at least one compound of formula (VII):

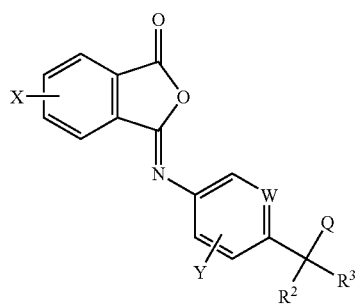

with at least one compound of said formula (V),
in the presence of at least one inert solvent, and if appropriate, in the presence of an acid catalyst;
(e) reacting at least one compound of formula (VIII):

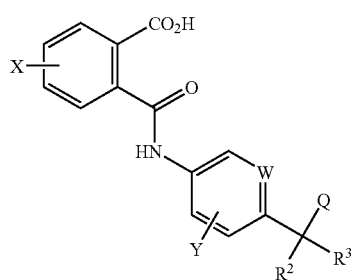

with at least one compound of said formula (V),
in the presence of at least one inert solvent, and if appropriate, in the presence of an acid catalyst;
(f) In this reaction scheme f, $R^1$ is $C_{1-6}$ alkylsulfinyl-$C_{1-6}$ alkyl or $C_{1-6}$ alkylsulfonyl-$C_{1-6}$ alkyl, and said reaction scheme f comprises reacting compounds of formula (If):

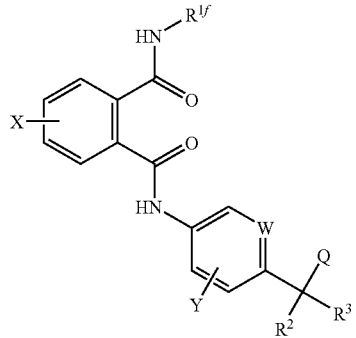

wherein $R^{1f}$ represents $C_{1-6}$ alkylthio-$C_{1-6}$ alkyl,
with an oxidant in the presence of at least one inert solvent.

4. An Insecticidal composition comprising, at least one benzanilide of claim 1.

5. A method for combatting harmful insects comprising allowing at least one benzanilide of claim 1 to act on harmful insects and/or on a habitat thereof and/or on propagation material thereof.

6. A process for the preparation of an insecticidal composition, comprising mixing at least one benzanilide of claim 1 with at least one extender and/or at least one surface active agent.

7. A composition for treating seeds comprising a compound according to claim 1.

8. A composition for treating transgenic plants comprising a compound of claim 1.

9. A composition for treating seeds of transgenic plants comprising a compound of claim 1.

10. Method for treating seeds comprising treating the seeds with a composition according to claim 4.

11. Method for treating transgenic plants comprising applying a composition according to claim 4.

12. Method for treating the seeds of transgenic plants comprising treating the seeds of transgenic plants with a composition according to claim 4.

13. Seeds treated with a composition according to claim 4.

14. A compound according to claim 1 in which
X is Cl or I;
Y is methyl;
$R^1$ is $CH(CH_3)CH_2SCH_3$, $CH(CH_3)CH_2SOCH_3$, or $CH(CH_3)CH_2SO_2CH_3$;
$R^2$ is H or $CF_3$;
$R^3$ is H;
W is CH; and
Q is substituted phenyl wherein the substituent is at least one $CF_3$, $C_2F_5$, $C_3F_7$, or $C_4F_9$.

15. An insecticidal composition of claim 4, wherein the benzanilide is at a concentration of at least 20 ppm.

16. An insecticidal composition of claim 4, wherein the benzanilide is at a concentration of not more than 20 ppm.

* * * * *